US012698504B2

(12) United States Patent
Church et al.

(10) Patent No.: US 12,698,504 B2
(45) Date of Patent: Aug. 4, 2026

(54) METHODS FOR MAKING AND USING GENOMICALLY RECODED CELLS

(71) Applicant: President and Fellows of Harvard College, Cambridge, MA (US)

(72) Inventors: George M. Church, Brookline, MA (US); Akos Nyerges, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 18/255,160

(22) PCT Filed: Dec. 7, 2021

(86) PCT No.: PCT/US2021/062177
§ 371 (c)(1),
(2) Date: May 31, 2023

(87) PCT Pub. No.: WO2022/125531
PCT Pub. Date: Jun. 16, 2022

(65) Prior Publication Data
US 2024/0002865 A1        Jan. 4, 2024

Related U.S. Application Data

(60) Provisional application No. 63/122,426, filed on Dec. 7, 2020.

(51) Int. Cl.
*C12N 15/70*        (2006.01)

(52) U.S. Cl.
CPC ................................... *C12N 15/70* (2013.01)

(58) Field of Classification Search
None
See application file for complete search history.

(56) References Cited

U.S. PATENT DOCUMENTS

| | | |
|---|---|---|
| 2002/0156042 A1 | 10/2002 | Panchal et al. |
| 2011/0189195 A1 | 8/2011 | Kim et al. |
| 2014/0081007 A1 | 3/2014 | Rothschild et al. |
| 2021/0123064 A1* | 4/2021 | Isaacs ................... C12N 15/70 |

OTHER PUBLICATIONS

Genetic Code. https://en.wikipedia.org/wiki/Genetic_code, [retrieved Jul. 3, 2024] (Year: 2024).*
Kano et al., Unassigned or nonsense codons in Micrococcus luteus. J. Mol. Biol. (1993), 230: 51-56 (Year: 1993).*
Liebl et al., Plasmid-borne macrolide resistance in Micrococcus luteus. Microbiology (2002), 148: 2479-2487 (Year: 2002).*
GenBank: KC005723.1, Micrococcus luteus strain MAW843 plasmid pMEC2, complete sequence. https://www.ncbi.nlm.nih.gov/nuccore/ KC005723, [retrieved Jul. 3, 2024] (Year: 2020).*
Lajoie et al., Genomically Recoded Organisms Expand Biological Functions. Science (2013), 342: 357-360 (Year: 2013).*
GenBank: M62654.1, Aequorea victoria green-fluorescent protein mRNA, complete cds, https://www.ncbi.nlm.nih.gov/nuccore/ 155662, [retrieved Jul. 3, 2024] (Year: 1993).*
Clark, M. A. (2018). Chapter 15: Genes and Proteins. In Biology 2e. Houston, Texas: OpenStax. (Year: 2018).*
Rosano et al., New tools for recombinant protein production in *Escherichia coli*: A 5-year update. Protein Science (2019), 28: 1412-1422 (Year: 2019).*
Castineiras et al., *E. coli* strain engineering for the production of advanced biopharmaceutical products. FEMS Microbiology Letters (2018), 365(15), 1-10 (Year: 2018).*
McElwain et al., Current trends in biopharmaceuticals production in *Escherichia coli*. Biotehcnol Lett (2022) 44: 917-931 (Year: 2022).*
Mar. 24, 2022—(WO) International Search Report & Written Opinion—App. No. PCT/US2021/062177.
Zhang et al., "The biological process of lysine-tRNA charging is therapeutically targetable in liver cancer," Liver International, vol. 41, No. 1, pp. 206-219 (Oct. 20, 2020).

* cited by examiner

*Primary Examiner* — Catherine Konopka
(74) *Attorney, Agent, or Firm* — Banner & Witcoff, Ltd.

(57) ABSTRACT

Methods making and using genomically recoded cells or organisms are provided including genomically recoded cells or organisms that lack the ability to translate a foreign nucleic acid sequence into a polypeptide that may be toxic to the genomically recoded cell or organism.

16 Claims, 4 Drawing Sheets

Specification includes a Sequence Listing.

METHODS FOR MAKING AND USING GENOMICALLY RECODED CELLS

RELATED APPLICATIONS

This application is a National Stage Application under 35 U.S.C. 371 of PCT application PCT/US2021/062177 designating the United States and filed Dec. 7, 2021; which claims the benefit of U.S. provisional application No. 63/122,426 filed on Dec. 7, 2020 each of which are hereby incorporated by reference in their entireties.

STATEMENT OF GOVERNMENT INTERESTS

This invention was made with government support under DE-FG02-02ER63445 awarded by the U.S. Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on May 23, 2024, is named "Sequence_Listing_010498_01544_ST25" and is 56,670 bytes in size.

FIELD

The present invention generally relates to methods for making and using genomically recoded cells or organisms.

BACKGROUND

Industrially synthesized or constructed DNA sequences, regardless of their source or application, are most frequently maintained and manipulated in microbial host cells, e.g., in *Escherichia coli (E. coli)*. Yet a significant fraction of DNA sequences is toxic or pose high metabolic burden to the microbial host cells and thus, unclonable or unstable in microbial host cells. Based on prior studies, 2.6% of all tested microbial genes, approximately 106 genes in an average microbial genome, are toxic in *E. coli*. A list of 41,821 toxic genes from prokaryotic and eukaryotic genomes is provided in Kimelman A, Levy A, Sberro H, Kidron S, Leavitt A, Amitai G, Yoder-Himes D R, Wurtzel O, Zhu Y, Rubin E M, Sorek R (2012) A vast collection of microbial genes that are toxic to bacteria. *Genome Research,* 22(4):802-809 hereby incorporated by reference in its entirety. DNA constructs, methods of producing proteins and methods to make DNA vaccines are known. See Selas Castiñeiras T, Williams S G, Hitchcock A G, Smith D C (2018) *E. coli* strain engineering for the production of advanced biopharmaceutical products. *FEMS Microbiology Letters,* 365(15); Chakiath C S, Esposito D (2007) Improved recombinational stability of lentiviral expression vectors using reduced-genome *Escherichia coli. BioTechniques,* 43(4):466-470; Pósfai G, Plunkett G, Fehér T, Frisch D, Keil G M, Umenhoffer K, Kolisnychenko V, Stahl B, Sharma S S, De Arruda M (2006) Emergent properties of reduced-genome *Escherichia coli. Science,* 312(5776):1044-1046; Umenhoffer K, Fehér T, Balikó G, Ayaydin F, Pósfai J, Blattner F R, Pósfai G (2010) Reduced evolvability of *Escherichia coli* MDS42, an IS-less cellular chassis for molecular and synthetic biology applications. *Microbial cell factories,* 9; Campbell J W, Blattner F R, Plunkett G, Posfai G (2012) Reduced genome *E. coli*. U.S. Pat. No. 8,178,339 and Cottingham M G, Carroll F, Morris S J, Turner A V, Vaughan A M, Kapulu M C, Colloca S, Siani L, Gilbert S C, Hill A V S (2012) Preventing spontaneous genetic rearrangements in the transgene cassettes of adenovirus vectors. *Biotechnology and Bioengineering,* 109(3):719-728 each of which are hereby incorporated by reference in its entirety.

Furthermore, instability issues frequently prevent vaccine and viral vector construction (Umenhoffer K, Fehér T, Balikó G, Ayaydin F, Pósfai J, Blattner F R, Pósfai G (2010) Reduced evolvability of *Escherichia coli* MDS42, an IS-less cellular chassis for molecular and synthetic biology applications. *Microbial cell factories,* 9 and Cottingham M G, Carroll F, Morris S J, Turner A V, Vaughan A M, Kapulu M C, Colloca S, Siani L, Gilbert S C, Hill A V S (2012) Preventing spontaneous genetic rearrangements in the transgene cassettes of adenovirus vectors. *Biotechnology and Bioengineering,* 109(3):719-728) and the rapid analysis of pathogenic viruses, including Flaviviridae, Zika, and SARS-CoV-2. Viral reverse genetics has been an indispensable tool to reconstruct viruses purely from sequence data and to aid rapid vaccine development. However, viral genomes are especially cumbersome to clone and to manipulate in bacterial hosts due to instability issue. This instability of eukaryotic or viral sequences is driven by the presence of cryptic bacterial promoters and thus, the expression of toxic proteins or peptides.

Multiple solutions have been proposed to increase stability for difficult-to-clone DNA sequences in microbial host cells. However, these methods suffer from limitations such as high metabolic burden imposed on hosts due to undesired expression from cryptic internal host promoters.

SUMMARY

Aspects of the present disclosure are directed to method of making genomically recoded cells or organisms. Cells may be genomically recoded as is known in the art by creating unassigned codons. Unassigned codons do not have a cognate tRNA associated with the codon. A codon may be unassigned when the cell is modified to prevent production of the tRNA cognate to the codon. A codon may be unassigned by altering the three nucleotide sequence for the codon. In either example, the cell does not produce a tRNA that recognizes the codon, and so the codon is "unassigned." Materials and methods useful in the practice of the present disclosure in making and using genomically recoded cells or organisms are provided in WO2017/218727 hereby incorporated by reference in its entirety.

Aspects of the present disclosure are directed to a method for altering a cell, wherein the cell lacks (1) one or more native genes operative to encode one or more tRNA cognate to one or more canonical codons thereby rendering the one or more canonical codons unassigned in the cell or (2) one or more native genes operative to encode one or more release factors. The method provides introducing into the cell a foreign nucleic acid sequence of canonical codons encoding a polypeptide, wherein lack of the cell to produce (1) the one or more tRNA cognate to the one or more canonical codons or (2) the one or more release factors prevents expression of the foreign nucleic acid sequence into the polypeptide.

Aspects of the present disclosure are directed to a method for altering a cell including providing a cell with a foreign nucleic acid sequence of canonical codons encoding a polypeptide, wherein one or more canonical codon sequences within the foreign nucleic acid sequence are altered to produce one or more unassigned codons within the cell, wherein presence of the unassigned codon reduces or prevents expression of the foreign nucleic acid sequence into the polypeptide, wherein the unassigned codon is optionally located upstream of the nucleic acid sequence encoding the protein, wherein the unassigned codon is optionally located in a promoter cognate to the foreign nucleic acid sequence, or wherein the unassigned codon is optionally located within the open reading frame of the foreign nucleic acid sequence.

Aspects of the present disclosure are directed to a method for expressing a foreign nucleic acid sequence to produce a polypeptide in a cell, wherein the cell lacks (1) one or more native genes operative to encode one or more tRNA cognate to one or more canonical codons within the foreign nucleic acid sequence or (2) one or more native genes operative to encode one or more release factors. The method includes providing the cell with the foreign nucleic acid sequence, optionally providing the cell with an expression plasmid or vector that is expressed (1) to provide the one or more tRNA cognate to the one or more canonical codons within the foreign nucleic acid sequence or (2) the one or more release factors, wherein the cell translates the foreign nucleic acid sequence to produce the polypeptide, or optionally, wherein the cell is genetically modified to encode one or more tRNA cognate to one or more canonical codons within the foreign nucleic acid sequence under the influence of an inducible promoter and inducing the inducible promoter to begin translation of the foreign nucleic acid sequence to produce the polypeptide.

In one embodiment, the foreign nucleic acid sequence encodes a protein or peptide or polypeptide or oligopeptide which when expressed is toxic to the cell. In one embodiment, a codon has been eliminated and replaced genome-wide in the genomically recoded organism. The eliminated/replaced codon is termed a forbidden codon or unassigned codon. The forbidden or unassigned codon can be reassigned to incorporate a desired amino acid into a protein or peptide under suitable conditions. In other embodiments, multiple codons can be eliminated and replaced genome-wide in the genomically recoded organism. In one embodiment, tRNAs cognate for the eliminated/replaced forbidden/unassigned codons as well as the associated release factor are eliminated from the genomically recoded organism. In one embodiment, the foreign nucleic acid sequence contains the forbidden/unassigned codon in the open reading frame encoding the protein or peptide. In other embodiments, the foreign nucleic acid sequence contains multiple forbidden/unassigned codons in the open reading frame encoding the protein or peptide. The presence of the forbidden/unassigned codon(s) in the open reading frame encoding the protein or peptide within the foreign nucleic acid sequence prevents translation or proper translation of the protein or peptide. In one embodiment, the improperly translated protein or peptide is degraded in the host cell. In one embodiment, the corresponding cognate tRNAs and associated release factor are provided to the host exogenously to allow proper translation of the protein or peptide. In one embodiment, the corresponding cognate tRNAs and associated release factor are supplied from exogenous expression vectors in an inducible manner which restores translation and the expression for the protein or peptide of interest. Methods according to the present disclosure allows for uncoupling of foreign nucleic acid sequence propagation from its encoded polypeptide expression, which leads to a stable in vivo propagation of the foreign nucleic acid sequence and subsequent high-yield protein production, for example from otherwise toxic genetic elements.

Further features and advantages of certain embodiments of the present disclosure will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1 illustrates an example graph of the CTX-VP60 chimeric construct containing many forbidden codons in orf238.

FIG. 2 illustrates an example graph of the sequence of the CTX-VP60 chimeric construct, with UUG and UUA leucine codons marked as "Forbidden Codon" in orf238 in accordance with one or more exemplary embodiments. (SEQ ID Nos:18-19)

DETAILED DESCRIPTION

Figure 3:
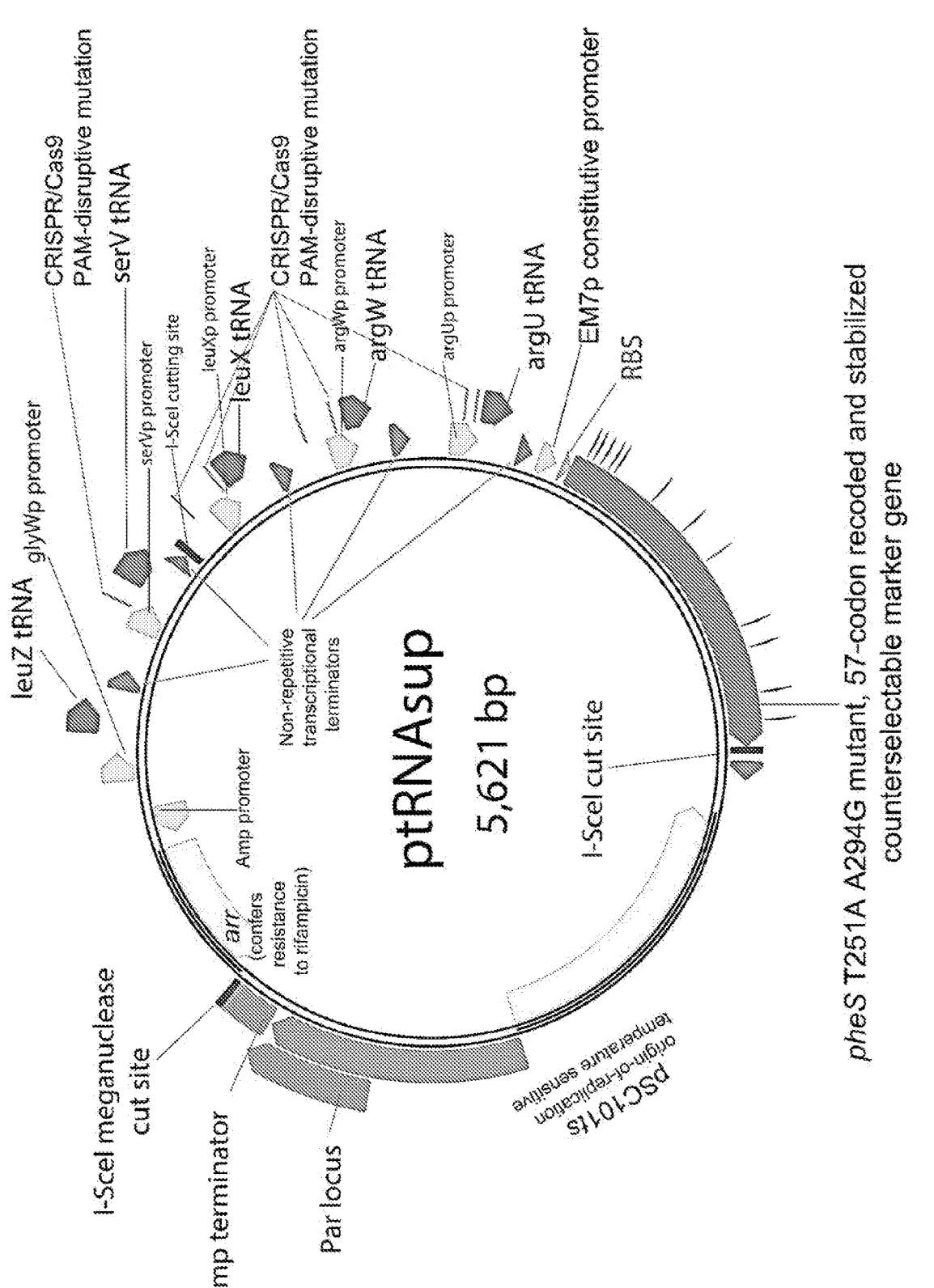
FIG. 3 illustrate a schematic structure of the ptRNAsup plasmid in accordance with an exemplary embodiment.

According to certain aspects, the present disclosure provides methods and compositions for maintenance and expression of foreign nucleic acid sequences, such as those encoding polypeptides toxic to the host cell in a genomically recoded organism (GRO). In certain embodiments, in a genomically recoded organism as that term is well understood to those of skill in the art (see Ma N J, Moonan D W, Isaacs F J (2014) Precise manipulation of bacterial chromosomes by conjugative assembly genome engineering. *Nature Protocols,* 9(10):2285-2300 and Lajoie M J, Rovner A J, Goodman D B, Aerni H-R, Haimovich A D, Kuznetsov G, Mercer J A, Wang H H, Carr P A, Mosberg J A, Rohland N, Schultz P G, Jacobson J M, Rinehart J, Church G M, Isaacs F J (2013) Genomically Recoded Organisms Expand Biological Functions. *Science,* 342(6156):357-360 each of which is hereby incorporated by reference in its entirety for making and using genomically recoded organisms), single or multiple canonical genetic codons are eliminated genome-wide and their cognate tRNA(s) and/or release factor (i.e., RF1, prfA) are deleted from the GRO genome. In one embodiment, the foreign nucleic acid sequence contains the eliminated genetic codon(s), such as in the open reading frame of the genetic-elements-of-interest. As a result, an otherwise toxic genetic-element-of-interest can be maintained in the genomically recoded organism. This is because in the absence of the cognate tRNA and/or release factor, the otherwise toxic genetic elements become improperly translated at codons that lack the corresponding tRNA and/or release factor (see Ostrov N, Landon M, Guell M, Kuznetsov G, Teramoto J, Cervantes N, Zhou M, Singh K, Napolitano M G, Moosburner M, Shrock E, Pruitt B W, Conway N, Goodman D B, Gardner C L, Tyree G, Gonzales A, Wanner B L, Norville J E, Lajoie M J, Church G M (2016) Design, synthesis, and testing toward a 57-codon genome. *Science,* 353(6301):819-822; and Ma N J, Isaacs F J (2016) Genomic Recoding Broadly Obstructs the Propagation of Horizontally Transferred Genetic Elements. *Cell Systems,* 3(2):199-207 each of which are hereby incorporated by reference in its entirety. Consequently, cloning and propagating of the foreign nucleic acid sequence in GROs removes the associated fitness cost for genetic-elements-of-interest, for example, where whose (cryptic) expression would be otherwise toxic in organisms that are carrying the canonical genetic code.

According to certain other aspects of the present disclosure, when expression from the genetic-elements-of-interest is desired (e.g., in the production stage of fed-batch fermentation), the cognate tRNAs and/or release factor 1 (e.g., PrfA) are supplied from an exogenous expression vector, for example in an inducible manner, which in turn restores translation and expression for the genetic-elements-of-interest after induction. Therefore, the disclosed methods allow for the stable in vivo propagation and then, high-yield protein production, for example from otherwise toxic or unstable genetic elements.

Vectors according to the present disclosure include those known in the art as being useful in delivering genetic material into a host organism or cell and would include regulators, promoters, nuclear localization signals (NLS), start codons, stop codons, a transgene etc., and any other genetic elements useful for maintenance and expression, as are known to those of skill in the art.

The first reported GRO is of prokaryotic origin, i.e., a bacterium, a strain of *E. coli*. See Lajoie M J, Rovner A J, Goodman D B, Aerni H-R, Haimovich A D, Kuznetsov G, Mercer J A, Wang H H, Carr P A, Mosberg J A, Rohland N, Schultz P G, Jacobson J M, Rinehart J, Church G M, Isaacs F J (2013) Genomically Recoded Organisms Expand Biological Functions. *Science,* 342(6156):357-360 hereby incorporated by reference in its entirety. Cells of GRO according to the present disclosure include any cell into which foreign nucleic acids can be introduced and expressed as described herein. It is to be understood that the basic concepts of the present disclosure described herein are not limited by cell type for GROs. According to one aspect, the cell is a eukaryotic cell or a prokaryotic cell. According to one aspect, the cell is a yeast cell, bacterial cell, fungal cell, a plant cell or an animal cell. According to one aspect, the cell is a mammalian cell. According to one aspect, the cell is a human cell.

Embodiments of the present disclosure include GROs allowing for the presence of unassigned genetic codons in the genetic code. Exemplary GROs according to the present disclosure include strain *E. coli* C321.ΔA in which the stop codon UAG is eliminated/replace with UAA genome-wide. The unassigned UAG codon is thus available to be reassigned to encode a desired amino acid. As another example, GROs according to the present disclosure include strain rE.coli-57, in which the AGA, AGG, AGC, AGU, UUA, UUG, and UAG canonical codons in rE.coli-57 are replaced with their respective synonymous codons. See Ostrov N, Landon M, Guell M, Kuznetsov G, Teramoto J, Cervantes N, Zhou M, Singh K, Napolitano M G, Moosburner M, Shrock E, Pruitt B W, Conway N, Goodman D B, Gardner C L, Tyree G, Gonzales A, Wanner B L, Norville J E, Lajoie M J, Church G M (2016) Design, synthesis, and testing toward a 57-codon genome. *Science,* 353(6301):819-822 for the description of rE.coli-57 each of which is hereby incorporated by reference in its entirety. In addition, tRNAs for ΔargU ΔargW ΔserV ΔleuX ΔleuZ and release factor ΔprfA are deleted from the genome of the strain rE.coli-57. In another example, *E. coli* Syn61 the UCG, UCA, and UAG canonical codons in rE.coli-57 are replaced with their respective synonymous alternatives and ΔserU and ΔserT, and release factor ΔprfA are deleted from the genome. See also Wang K, Fredens J, Brunner S F, Kim S H, Chia T, Chin J W (2016) Defining synonymous codon compression schemes by genome recoding. *Nature,* 539(7627):59-64 for the description of *E. coli* Syn61. In yet another example, GROs according to the present disclosure include strain *Saccharomyces cerevisiae* Sc2.0 in which the stop codon UAG is eliminated/replace with UAA genome-wide. See Lajoie M J, Rovner A J, Goodman D B, Aerni H-R, Haimovich A D, Kuznetsov G, Mercer J A, Wang H H, Carr P A, Mosberg J A, Rohland N, Schultz P G, Jacobson J M, Rinehart J, Church G M, Isaacs F J (2013) Genomically Recoded Organisms Expand Biological Functions. *Science,* 342(6156):357-360 and Ostrov N, Landon M, Guell M, Kuznetsov G, Teramoto J, Cervantes N, Zhou M, Singh K, Napolitano M G, Moosburner M, Shrock E, Pruitt B W, Conway N, Goodman D B, Gardner C L, Tyree G, Gonzales A, Wanner B L, Norville J E, Lajoie M J, Church G M (2016) Design, synthesis, and testing toward a 57-codon genome. *Science,* 353(6301):819-822 each of which is hereby incorporated by reference in its entirety.

When a foreign nucleic acid sequence, such as a foreign DNA sequence encoding a polypeptide of interest, containing a forbidden/unassigned codon is introduced into a genomically recoded cell or organism, i.e. which lacks a tRNA for the forbidden/unassigned codon, the foreign DNA sequence is not translated into the polypeptide, as the cell or organism lacks the cellular machinery to do so.

In prokaryotic cells, encountering an unassigned codon during translation leads to ribosomal stalling, and in turn, rescue mechanisms that result in improperly translated proteins with altered C-terminal sequences and/or early termination. In *E. coli* cells, the tmRNA(ssrA)-SmpB system acts as the primary rescue mechanism leading to the addition of a C-terminal degradation tag (-AANDENYALAA) (SEQ ID NO:1) to peptides at the stalled ribosome. As a consequence, the synthesized protein becomes quickly degraded (see Keiler K C (2015) Mechanisms of ribosome rescue in bacteria. *Nature Reviews Microbiology,* 13(5):285-297 hereby incorporated by reference in its entirety. In eukaryotes, RNA quality control mechanisms quickly eliminate mRNAs that are containing the unassigned codons (see Doma M K, Parker R (2007) RNA Quality Control in Eukaryotes. Cell, 131(4):660-668 hereby incorporated by reference in its entirety.)

According to certain aspects of the present disclosure, the maintenance and production of genetic elements, i.e. foreign nucleic acid sequences, where polypeptide or protein expression can be toxic to the cell, can be accomplished in GROs as described herein that where the foreign nucleic acid sequence includes unassigned codons within the cell, i.e. where the cell lacks a cognate tRNA for the unassigned codon.

In some embodiments, a DNA sequence is not part of a cell's natural nucleic acid composition, i.e. is a foreign nucleic acid sequence, and may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources. According to one aspect, a DNA sequence is exogenous/foreign to the cell.

In certain embodiments, genes coding for cognate tRNAs and release factors are deleted from a genomically recoded organism or cell using any method known to those skilled in the art for such deletion. Such deletion creates unassigned codons within the cell as is known to those of skill in the art. In one embodiment, a CRISPR/Cas9 and guide RNA system is used to target the cognate tRNAs and release factors for deletion or editing to render them inoperative. One of skill in the art will readily understand and adapt such methods using readily identifiable literature sources.

The degeneracy of the canonical genetic code allows the same amino acid to be encoded by multiple synonymous codons, as is known in the art. Once a codon is synonymously replaced genome-wide and/or its cognate tRNA and/or associated release factor is eliminated, the genomically recoded organism (GRO) may no longer translate the eliminated codon. The eliminated/replaced codons can be reassigned to desired amino acids. For example in genomically recoded $E.$ $coli$ C321.ΔA, the amber stop codon UAG is replaced genome-wide with the synonymous ochre stop codon UAA. Additional amino acids can be recoded to result in more genomically recoded strains. For example, in rEcoli-57 strain, either one or both of the UUG and UUA Leucine codons can be replaced with the synonymous Leucine codons such as CUU, CUC, CUA or CUG. Codons for Arginine and Serine can be similarly recoded. The replaced codons are also termed forbidden/unassigned codons. Exemplary forbidden/unassigned codons include AGA (Arg), AGG (Arg), AGC (Ser), AGU (Ser), UUG (Leu), UUA (Leu) and UAG (Stop). In addition, the cognate tRNA and/or release factor corresponding to the forbidden/unassigned codons can also be eliminated, i.e. the cell can be altered to prevent expression of the cognate tRNA and/or release factor. Such genomically recoded $E.$ $coli$ can be used to maintain and express DNA sequences that encode for polypeptides or proteins that may be toxic to the cell. For example, when a DNA sequence encodes a protein or peptide that is toxic to the host $E.$ $coli$ stain, it is difficult to propagate the DNA sequence in the host due to toxicity from the expressed protein to the host cells. According to certain aspects, toxicity is determined by a reduction in cell growth rate by at least 1%, 10%, 20%, 30%, 40%, 50%, 60%, 70%, 80%, 90% or 95% compared to growth rate of a corresponding wild type cell. In one embodiment, when the DNA sequence is introduced into the genomically recoded $E.$ $coli$ C321.ΔA strain, if the DNA sequence has the amber stop codon UAG at the end of the open reading frame, the genomically recoded $E.$ $coli$ C321.ΔA would not be able to recognize the stop codon UAG since both the stop codon UAG and/or its cognate tRNA and/or release factor are eliminated in the recoded host $E.$ $coli$ C321.ΔA strain, as is known in the art. The improperly translated protein will be degraded, and as such will not be toxic to the cell. Only when exogenous cognate tRNA for UAG and the associated release factor is provided to the $E.$ $coli$ C321.ΔA stain, will the DNA sequence be properly translated and expressed. In an alternative embodiment, the DNA sequence can have the ochre stop codon UAA at the end of the open reading frame. In such a case, the DNA sequence can be recoded to replace a genetic codon that normally encodes an amino acid in the middle of the open reading frame with the amber stop codon UAG. In this manner, when the recoded DNA sequence is introduced into the genomically recoded $E.$ $coli$ C321.ΔA, the genomically recoded $E.$ $coli$ C321.ΔA would not be able to translate the codon UAG in the middle of the open reading frame since both the codon UAG and its cognate tRNA and/or release factor are eliminated in the recoded host $E.$ $coli$ C321.ΔA strain. Once again, the improperly translated protein will be degraded. When expression of the protein is desired, the codon UAG in the middle of the open reading frame can be reassigned to incorporate the original amino acid in the middle of the open reading frame with exogenously supplied cognate tRNA and release factor to the recoded $E.$ $coli$ C321.ΔA stain. In this manner, the recoded DNA sequence having the codon UAG in the middle of the open reading frame can be properly translated with original amino acid at the UAG codon and expressed. Thus, methods according to the present disclosure allows the maintenance and propagation of the DNA sequence to be separated from its expression so that high-yield protein production can be achieved.

In another embodiment, if the DNA sequence uses e.g. the unassigned codon UUG to encode amino acid Leucine in the middle of the open reading frame, when the DNA sequence is introduced into a genomically recoded $E.$ $coli$ strain having the Leucine codon UUG replaced by its synonymous Leucine codon CUU, the genomically recoded $E.$ $coli$ strain would not be able to translate codon UUG since both the codon UUG and its cognate tRNA and associated release factor are eliminated in the recoded host $E.$ $coli$ strain. The incompletely translated protein will be quickly degraded. Only when exogenous cognate tRNA for UUG recognizing Leucine is provided to the recoded $E.$ $coli$ stain along with the associated release factor, will the DNA sequence be properly translated with Leucine at the UUG codon and expressed. In this manner, the maintenance and propagation of the DNA sequence can be separated from its expression so that high-yield protein production can be achieved.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables and accompanying claims.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art. Other equivalent embodiments will be apparent in view of the present disclosure, figures and accompanying claims.

Example I

Maintenance of Toxic DNA Sequence in a Genomically Recoded Organism

Figure 1:
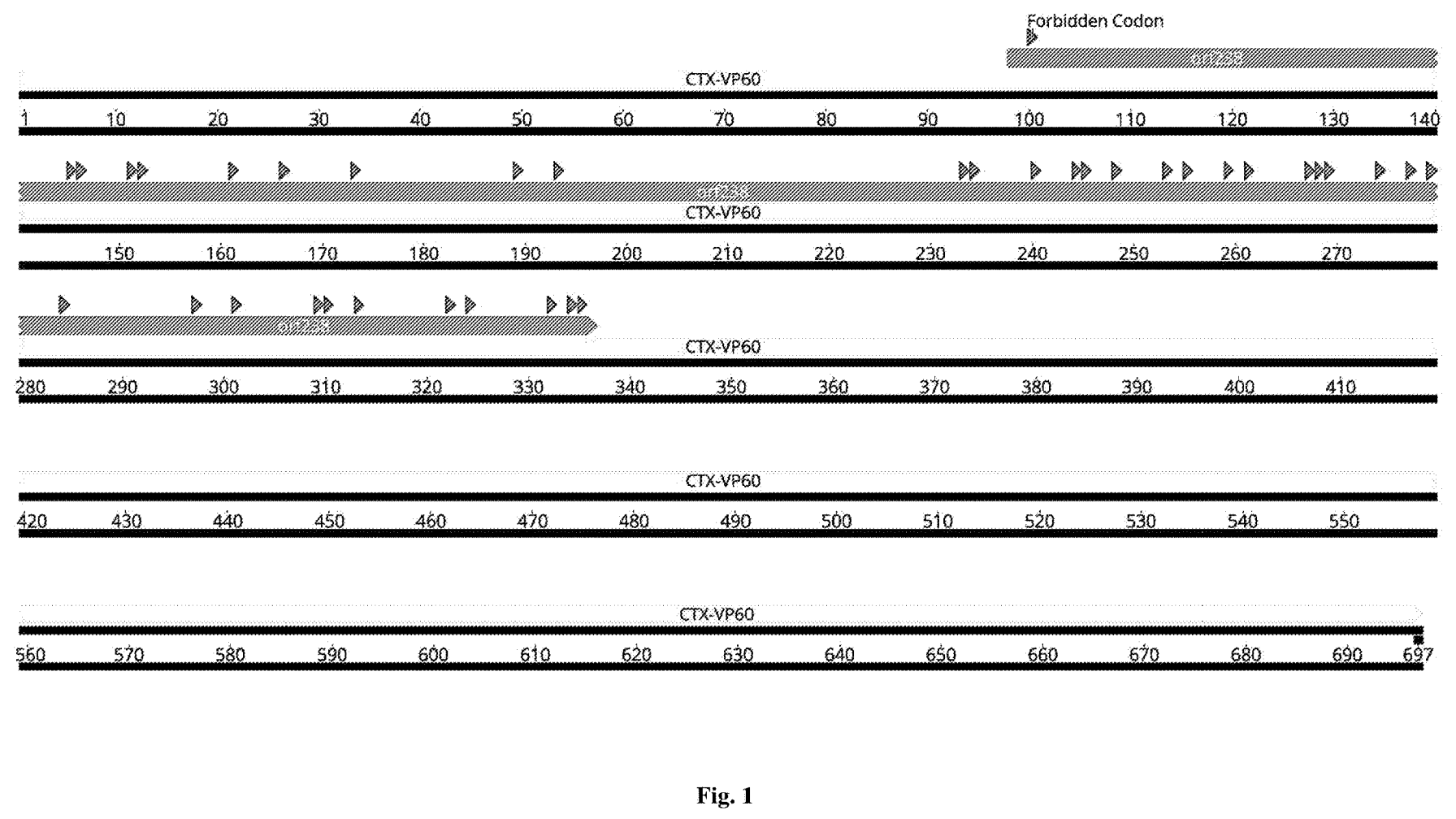

In this example, a chimeric gene CTX-VP60 was used. The chimeric gene CTX-VP60 is composed of a synthetic gene of the structural capsid protein VP60 of rabbit hemorrhagic disease (RHD) virus fused to the B subunit of cholera toxin (CTX). This chimeric gene is extremely unstable in industrial $E.$ $coli$ strains, due to severe toxicity See Pósfai G, Plunkett G, Fehér T, Frisch D, Keil G M, Umenhoffer K, Kolisnychenko V, Stahl B, Sharma S S, De Arruda M (2006) Emergent properties of reduced-genome *Escherichia coli.* *Science,* 312(5776):1044-1046 and Umenhoffer K, Fehér T, Balikó G, Ayaydin F, Pósfai J, Blattner F R, Pósfai G (2010) Reduced evolvability of *Escherichia coli* MDS42, an IS-less cellular chassis for molecular and synthetic biology applications. *Microbial cell factories,* 9 each of which are hereby incorporated by reference in its entirety for the description of CTX-VP60. The severe toxicity of CTX-VP60 is caused by an internal, leucine-rich protein-coding gene, termed orf238. In rE.coli-57 ΔleuX ΔleuZ, the plasmid including the chimeric gene sequence encoding CTX-VP60 can be maintained in the recoded rE.coli-57 ΔleuX ΔleuZ, as compared to wild type *E. coli.* Since orf238 in the chimeric gene CTX-VP60 includes a large number of "forbidden" leucine codons (i.e., UUG and UUA) in its open reading frame (see FIG. 1), proper translation of CTX-VP60 is not possible in the recoded rE.coli-57 ΔleuX ΔleuZ. Further, the LeuX and LeuZ tRNAs responsible for the recognition of mRNA codons UUG and UUA are eliminated from the recoded strain making translation not possible.

Example II

Expression of Toxic Protein from a DNA Sequence in a Genomically Recoded Organism In an exemplary embodiment, expression of toxic protein from a DNA sequence can be achieved in a genomically recoded organism. In this example, a counterselectable expression plasmid (ptRNAsup, and derivatives) that, after delivery into the target expression host lacking cognate tRNA genes and/or Release Factor 1, provides expression for necessary tRNAs for the production of the toxic target protein(s). Counterselection markers are generally described in Miyazaki K (2015) Molecular engineering of a PheS counterselection marker for improved operating efficiency in *Escherichia coli. BioTechniques,* 58(2):86-88 hereby incorporated by reference in its entirety.

In an alternative application, ptRNAsup and derivatives can allow for the CRISPR/Cas9-mediated deletion of endogenous tRNA and release factor genes by supplementing the host-cell with tRNA genes and/or Release Factor during the genome editing process. Then, once the chromosomal copies of these tRNA genes and/or Release Factor(s) are deleted, the ptRNAsup plasmid is selectively eliminable from the host at an elevated temperature and/or by simultaneous counterselection.

The ptRNAsup plasmid includes the following features for selective elimination.

Temperature-sensitive origin-of-replication: The pSC101ts origin of replication allows stable low copy number maintenance and tRNA and/or RF1 expression at 30-34 degrees Celsius but eliminated at elevated temperatures (i.e., >41 degrees Celsius).

Constitutively expressed arr (antibiotic resistance) gene: Provides resistance for the host to rifampicin (Rifampin) at 100-300 μg/mL concentration and thus allows selection for the presence of the ptRNAsup plasmid. Other suitable resistance genes (incl. cat, bla, aph(9)-Ia (Spec-R), Aac3-Ia (Gent-R)) can be used instead of arr, and these genes are widely known to those of skill in the art.

Constitutively expressed pheS T251A+A294G mutant gene: Derivative of the native *E. coli* MG1655 pheS gene, provides stringent counterselection against ptRNAsup in the presence of 4-chloro-phenylalanine (4CP) [27, 28] in *E. coli* and related Enterobacteria.

Other counterselectable markers that can confer similar functions include ccdB, rpsL, tetA, pyrF, sacB, and others that are widely known to those of skill in the art.

Figure 2:
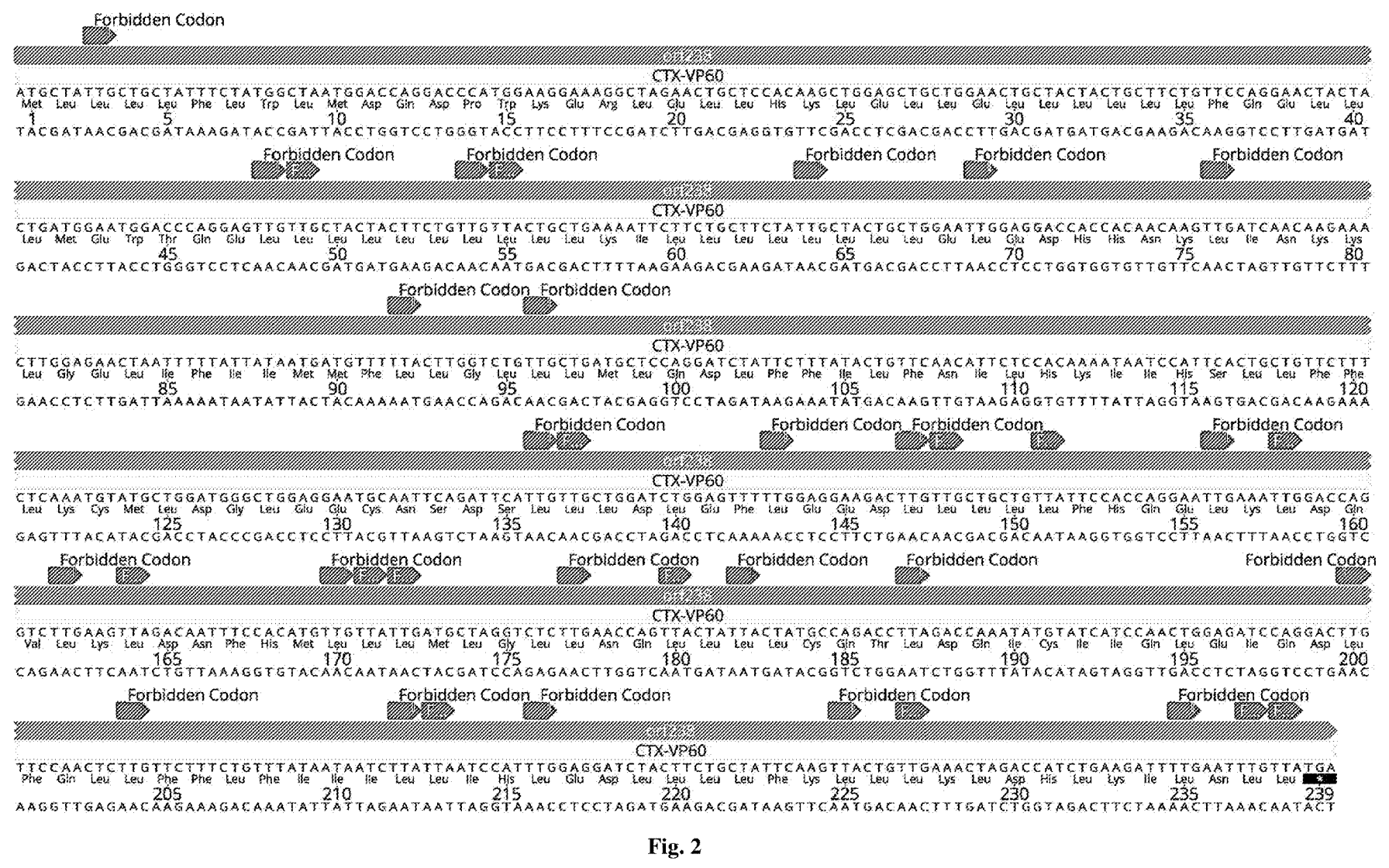

Constitutively or inducibly expressed tRNA genes and/or prfA (Release Factor 1) gene. The ptRNAsup plasmid variant that is displayed on FIG. 2 expresses leuZ, serV, leuX, argW, and argU from their native constitutive promoter. Inducible expression systems that can substitute the native promoter of these genes are available and widely known for people who are skilled in the art. The native constitutive promoters of these genes (leuZ, serV, leuX, argW, and argU) have been modified on a way to disrupt spCas9's PAM (NRG) site thereby allowing for the genomic deletion of the wild-type leuZ, serV, leuX, argW, and argU by Cas9-mediated recombineering or other alternative genome editing technologies.

I-SceI meganuclease cutting sites: Allows the elimination (by cutting) the ptRNAsup plasmid by the inducible expression of the I-SceI meganuclease. I-SceI recognizes and cleaves within an 18-base pair sequence 5'-TAGGGATAACAGGGTAAT (SEQ ID NO:2) that is not represented on bacterial genomes, and therefore it can be specifically directed to cleave ptRNAsup.

In alternative version of ptRNAsup, the tRNA genes can be replaced or extended with any inducible or constitutive promoter driven tRNA gene(s) and or Release Factor gene, i.e., prfA.

Example III

Expression of Toxic Hok Protein from a DNA Sequence in a Genomically Recoded Organism The bacterial Hok protein (SEQ ID NO:14) is the toxic component of a type I toxin-antitoxin (TA) system. When overexpressed, it kills cells within minutes by causing the collapse of the transmembrane potential and arrest of respiration (see Pedersen et al., Multiple hok genes on the chromosome of *Escherichia coli*, Molecular Microbiology, vol. 32, issue 5, pages 1090-1102 (1999; PubMed: 10361310). Due to its toxicity to bacterial cells, including *E. coli*, the high-level production of the Hok protein is exceptionally challenging.

According to one aspect, methods are provided to maintain constitutively expressed Hok production plasmids in *E. coli* cells and produce the functional Hok protein by controlling the availability of an aminoacylated tRNA that suppresses an unassigned codon inside the Hok gene. A Hok expression construct was constructed that contained a TAG unassigned codon at amino acid position 10 (SEQ ID NO: 8 ProC-maxRBS-hok) and cloned into a high-copy-number pUC-derived pJET1.2 plasmid. In wild-type *E. coli* cells, the TAG codon at this position is recognized by the cell's endogenous Release Factor 1 (PrfA) and thus terminates the translation of the otherwise toxic Hok protein. According to one aspect, the TAG-containing Hok expression construct (SEQ ID NO:8 ProC-maxRBS-hok) is stably maintained in common *E. coli* expression hosts, including *E. coli* DH10b and MDS42 cells. The pUC-ProC-maxRBS-hok construct was transformed into C321.ΔA.exp (Addgene strain #49018, Lajoie M J, Rovner A J, Goodman D B, Aerni H-R, Haimovich A D, Kuznetsov G, Mercer J A, Wang H H, Carr P A, Mosberg J A, Rohland N, Schultz P G, Jacobson J M, Rinehart J, Church G M, Isaacs F J (2013) Genomically Recoded Organisms Expand Biological Functions. *Science,* 342(6156):357-360. https://doi.org/10.1126/science.1241459). In C321.ΔA.exp, the RF1 is deleted from the genome, and therefore the TAG codon is unassigned. C321.ΔA.exp cells displayed normal growth in the presence of pUC-ProC-maxRBS-hok. The same pUC-ProC-maxRBS-hok construct was transformed into C321.ΔA.exp cells containing an inducible *Methanocaldococcus janna-schii* TyrRS tyrosine-tRNA ligase and the corresponding Tyr tRNA (SEQ ID NO:9 pEVOL_MJWTyRS-CUA). When induced with 0.2% arabinose in the growth medium, this pEVOL_MJWTyRS-CUA plasmid produces tyrosine-charged tRNAs with CUA anticodon, thus suppressing unassigned TAG codons in the C321.ΔA.exp cells by incorporating tyrosine at TAG codons into polypeptides during ribosomal protein synthesis.

These C321.ΔA.exp+pEVOL_MJWTyRS-CUA+pUC-ProC-maxRBS-hok cells displayed normal growth rate without the inducer and in the presence of 1% glucose that further represses the induction of pEVOL_MJWTyRS-CUA. In the presence of 0.2% arabinose in the growth medium, however, the cells displayed no growth even after 24 hours of incubation. Similarly, restreaking >10^9 bacterial cells to agar plates containing 0.2% arabinose resulted in no growth after 48 hours at 37 degrees Celsius. Control C321.ΔA.exp+pEVOL_MJWTyRS-CUA and C321.ΔA.exp+pUC-ProC-maxRBS-hok cells grew normally in the presence of arabinose inducer.

Figure 4:
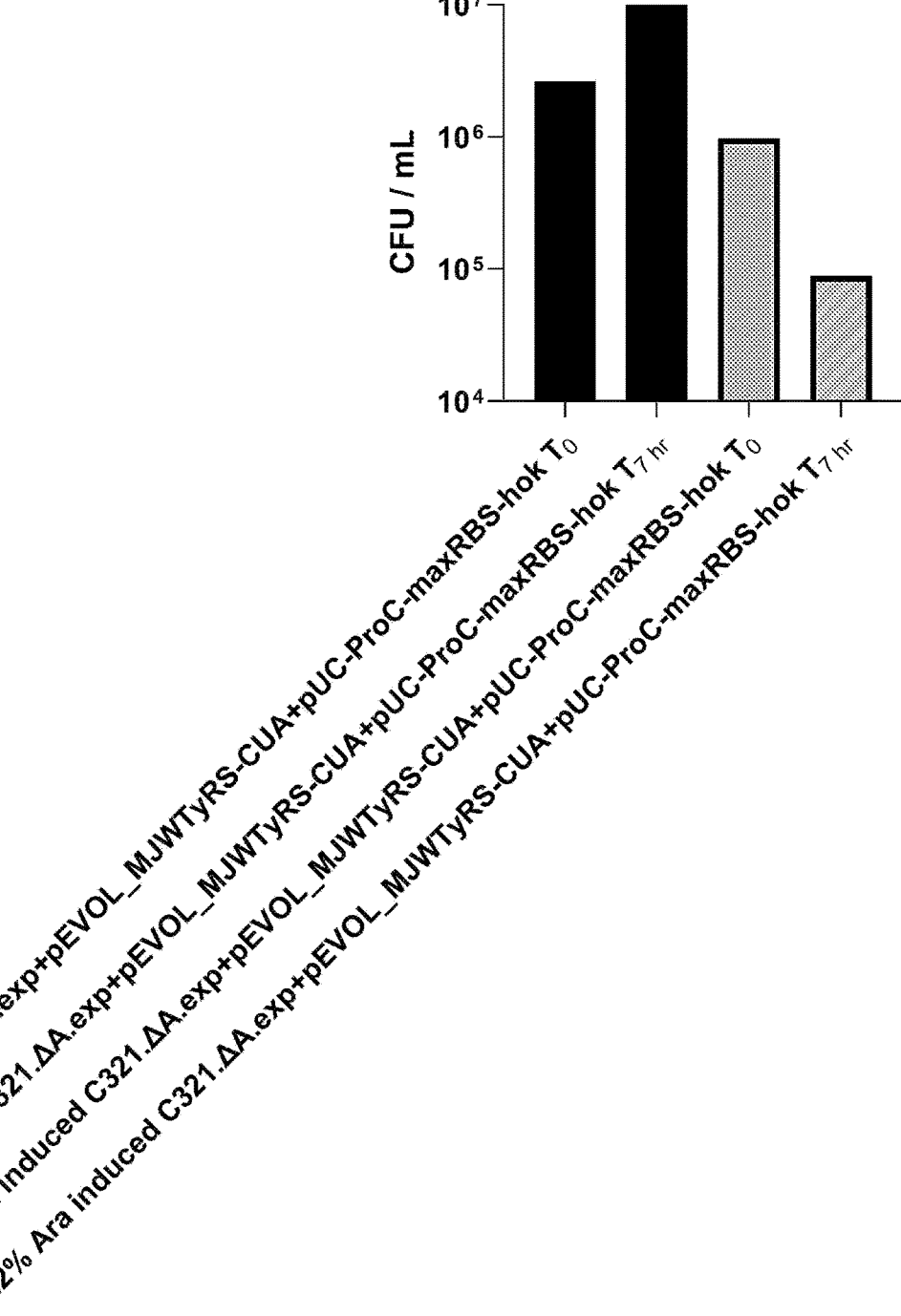
FIG. 4 depicts data from a time-course cell count experiment of the effect of high-level Hok production.

The effect of high-level Hok production was characterized by a time-course cell count experiment (see FIG. 4). In this experiment, an overnight starter culture of C321.ΔA.exp+pEVOL_MJWTyRS-CUA+pUC-ProC-maxRBS-hok cells from 1% glucose-containing medium was inoculated into both selective medium without inducer and separately, into selective medium with 0.2% arabinose inducer and incubated both aerobically at 37 degrees Celsius in a shaking incubator. Next, the viable cell count was assayed under both conditions at the time point of inoculation and after 7 hours of growth by plating cells on nonselective agar plates with 1% glucose. While the uninduced culture grew rapidly, approximately 90% of the arabinose-induced cells died after 7 hours of induction, demonstrating the extreme toxicity of functional Hok production.

Example IV

Additional Toxic Proteins as Targets

The protocol of Example III was carried out to test the expression of additional proteins in the C321.ΔA.exp+pEVOL_MJWTyRS-CUA expression system based on the unassigned TAG codon. The Kid (SEQ ID NO:15), mazF (SEQ ID NO:16), and timP (SEQ ID NO:17) toxic proteins were selected as targets. The Kid protein is the toxin part encoded by the parD operon of plasmid R1 (See Kimelman A, Levy A, Sberro H, Kidron S, Leavitt A, Amitai G, Yoder-Himes D R, Wurtzel O, Zhu Y, Rubin E M, Sorek R (2012) A vast collection of microbial genes that are toxic to bacteria. *Genome Research*, 22(4):802-809 and Hargreaves D, Santos-Sierra S, Giraldo R, Sabariegos-Jareno R, Cueva- Méndez G de la, Boelens R, Diaz-Orejas R, Rafferty J B (2002) Structural and Functional Analysis of the Kid Toxin Protein from *E. coli* Plasmid R1. *Structure,* 10(10):1425-1433). MazF is an mRNA interferase protein, which, upon expression, cleaves bacterial mRNAs in a sequence-specific manner, resulting in cellular growth arrest and cell death (see Kamada K, Hanaoka F, Burley S K (2003) Crystal Structure of the MazE/MazF Complex: Molecular Bases of Antidote-Toxin Recognition. *Molecular Cell,* 11(4):875-884 and Simanshu D K, Yamaguchi Y, Park J-H, Inouye M, Patel D J (2013) Structural Basis of mRNA Recognition and Cleavage by Toxin MazF and Its Regulation by Antitoxin MazE in *Bacillus subtilis. Molecular Cell,* 52(3):447-458.) The timP protein is a small, recently discovered bacterial toxin that results in rapid cell death upon induction (see Andresen L, Martinez-Burgo Y, Zangelin J N, Rizvanovic A, Holmqvist E (2020) The Small Toxic *Salmonella* Protein TimP Targets the Cytoplasmic Membrane and Is Repressed by the Small RNA TimR. mBio, 11(6) https://doi.org/10.1128/mBio.01659-20).

High-copy-number expression plasmids containing a strong constitutive bacterial promoter and strong ribosome binding site in front of the Kid, mazF, and timP genes containing two instances of the unassigned TAG codon were constructed. These plasmids are SEQ ID NO:10 pUC57-Kan-Kid, SEQ ID NO: 11 pUC57-Kan-mazF, and SEQ ID NO:12 pUC57-Kan-timP, respectively.

Next, the pUC57-Kan-Kid, pUC57-Kan-mazF, and pUC57-Kan-timP were transformed into C321.ΔA.exp cells containing an inducible *Methanocaldococcus jannaschii* TyrRS tyrosine-tRNA ligase and the corresponding Tyr tRNA (SEQ ID NO:9 pEVOL_MJWTyRS-CUA). When induced with 0.6% arabinose in the growth medium, this pEVOL_MJWTyRS-CUA plasmid produces tyrosine-charged tRNAs with CUA anticodon, thus suppressing unassigned TAG codons in the C321.ΔA.exp cells.

These C321.ΔA.exp+pEVOL_MJWTyRS-CUA+pUC57-Kan-Kid or +pUC57-Kan-mazF, or +pUC57-Kan-timP containing cells displayed only slightly reduced growth rate without the inducer and in the presence of 1% glucose that further represses the induction of pEVOL_MJWTyRS-CUA. In the presence of 0.6% arabinose inducer in the growth medium, the cells displayed no or minimal growth due to the high-level production of the toxic protein. The growth was measured as the optical density of the culture ($OD_{600}$), after 24 hours of incubation at 32 degrees Celsius (see Table 1). These experiments demonstrate the tight regulation of toxic protein expression based on the inducible supply of charged tRNAs suppressing an unassigned codon in genomically recoded organisms.

Table 1 below includes data of the maintenance of constitutively expressed, toxic Kid, mazF, and timP expression constructs in *E. coli* C321.ΔA cells and these proteins' inducible expression and subsequent toxicity by suppressing the unassigned TAG codon.

| Strain | Induction | Replicate | $OD_{600}$ |
|---|---|---|---|
| C321.ΔA.exp + pEVOL_MJWTyRS-CUA + pUC57-Kan-Kid | Uninduced | 1 | 1.66 |
| C321.ΔA.exp + pEVOL_MJWTyRS-CUA + pUC57-Kan-Kid | Uninduced | 2 | 1.63 |
| C321.ΔA.exp + pEVOL_MJWTyRS-CUA + pUC57-Kan-Kid | Uninduced | 3 | 1.81 |
| C321.ΔA.exp + pEVOL_MJWTyRS-CUA + pUC57-Kan-mazF | Uninduced | 1 | 1.98 |
| C321.ΔA.exp + pEVOL_MJWTyRS-CUA + pUC57-Kan-mazF | Uninduced | 2 | 1.82 |
| C321.ΔA.exp + pEVOL_MJWTyRS-CUA + pUC57-Kan-mazF | Uninduced | 3 | 1.69 |
| C321.ΔA.exp + pEVOL_MJWTyRS-CUA + pUC57-Kan-timP | Uninduced | 1 | 1.62 |
| C321.ΔA.exp + pEVOL_MJWTyRS-CUA + pUC57-Kan-timP | Uninduced | 2 | 1.63 |

-continued

| Strain | Induction | Replicate | OD$_{600}$ |
|---|---|---|---|
| C321.ΔA.exp + pEVOL_MJWTyRS-CUA + pUC57-Kan-timP | Uninduced | 3 | 1.58 |
| C321.ΔA.exp + pEVOL_MJWTyRS-CUA + pUC57-Kan-Kid | Induced with Arabinose | 1 | 0 |
| C321.ΔA.exp + pEVOL_MJWTyRS-CUA + pUC57-Kan-Kid | Induced with Arabinose | 2 | 0 |
| C321.ΔA.exp + pEVOL_MJWTyRS-CUA + pUC57-Kan-Kid | Induced with Arabinose | 3 | 0.62 |
| C321.ΔA.exp + pEVOL_MJWTyRS-CUA + pUC57-Kan-mazF | Induced with Arabinose | 1 | 0.01 |
| C321.ΔA.exp + pEVOL_MJWTyRS-CUA + pUC57-Kan-mazF | Induced with Arabinose | 2 | 0.05 |
| C321.ΔA.exp + pEVOL_MJWTyRS-CUA + pUC57-Kan-mazF | Induced with Arabinose | 3 | 0 |
| C321.ΔA.exp + pEVOL_MJWTyRS-CUA + pUC57-Kan-timP | Induced with Arabinose | 1 | 0 |
| C321.ΔA.exp + pEVOL_MJWTyRS-CUA + pUC57-Kan-timP | Induced with Arabinose | 2 | 0 |
| C321.ΔA.exp + pEVOL_MJWTyRS-CUA + pUC57-Kan-timP | Induced with Arabinose | 3 | 0 |

Example V

Human Growth Hormone Receptor as a Toxic Gene

The gene encoding the human growth hormone receptor (hGHR, SEQ ID NO:6 hGHR_wt) displays a high level of instability and is extremely toxic to *E. coli* bacterial expression hosts. See Bieth E, Cahoreau C, Cholin S, Molinas C, Cerutti M, Rochiccioli P, Devauchelle G, Tauber M (1997) Human growth hormone receptor: cloning and expression of the full-length complementary DNA after site-directed inactivation of a cryptic bacterial promoter. *Gene,* 194(1):97-105. Instability is believed to result from a cryptic bacterial promoter inside the wild-type sequence of hGHR that provides a high level of expression for an unknown downstream protein sequence.

The toxicity of SEQ ID NO:6 hGHR_wt was characterized by cloning the sequence into a high-copy-number, pUC-57 derived plasmid. The cloning of hGHR_wt was carried out in an *E. coli* host (Lucigen CopyCutter™ EPI400™ cells) that reduces the copy number of the pUC-hGHR_wt plasmid to medium-copy-number, thus reducing the expression level of the toxic protein by an order of magnitude (see Haskins, D. (2004) *Epicentre Forum* 11(5), 6.).

The pUC-hGHR_wt plasmid was transformed into various *E. coli* cloning and industrial strains, including *E. coli* TOP10 and MDS42. The high toxicity of pUC-hGHR_wt to *E. coli* cells, is described in Bieth E, Cahoreau C, Cholin S, Molinas C, Cerutti M, Rochiccioli P, Devauchelle G, Tauber M (1997) Human growth hormone receptor: cloning and expression of the full-length complementary DNA after site-directed inactivation of a cryptic bacterial promoter. *Gene,* 194(1):97-105 prevents obtaining transformants containing intact copies of pUC-hGHR_wt.

Recoded plasmid-borne versions of hGHR_wt, termed pUC-hGHR_wt-RC55 and p15A-hGHR_wt-RC55 containing the wild-type non-recoded hGHR sequence and a recoded antibiotic resistance marker, together with a high-copy-number pUC or a medium copy-number p15A bacterial origin-of-plasmid-replication, respectively were synthesized. These sequences are provided as SEQ ID NO:7 pUC-hGHR_wt-RC55 and SEQ ID NO:13 p15A-hGHR_wt-RC55.

Next, pUC-hGHR_wt-RC55 and p15A-hGHR_wt-RC55 were transformed into *E. coli* Syn61 and *E. coli* Syn61Δ3 (ev5). The recoded *E. coli* Syn61Δ3(ev5) lacks the serU and serT tRNA genes that encode serine tRNAs with CGA and UGA anticodons and recognize serine codons TCG and TCA. Furthermore, *E. coli* Syn61Δ3(ev5) also lacks the gene encoding Release Factor 1, prfA. Consequently, in *E. coli* Syn61Δ3(ev5), codons TCG, TCA, and TAG are unassigned and coding sequences having these codons are not expressed in this host. *E. coli* Syn61 and Syn61Δ3(ev5) are described in Fredens J, Wang K, Torre D de la, Funke L F H, Robertson W E, Christova Y, Chia T, Schmied W H, Dunkelmann D L, Beránek V, Uttamapinant C, Llamazares A G, Elliott T S, Chin J W (2019) Total synthesis of *Escherichia coli* with a recoded genome. *Nature:* 1. https://doi.org/10.1038/s41586-019-1192-5 and Robertson W E, Funke L F H, Torre D de la, Fredens J, Elliott T S, Spinck M, Christova Y, Cervettini D, Böge F L, Liu K C, Buse S, Maslen S, Salmond G P C, Chin J W (2021) Sense codon reassignment enables viral resistance and encoded polymer synthesis. *Science,* 372(6546):1057-1062. The whole genome sequence of Syn61Δ3(ev5) is available at NCBI Genbank as CP071799.1.

Colonies of Syn61Δ3(ev5) transformed with pUC-hGHR_wt-RC55 and p15A-hGHR_wt-RC55 display normal growth rate on selective medium. Syn61 transformed with p15A-hGHR_wt-RC55 displays abnormal, slow growth. Repeated transformation of pUC-hGHR_wt-RC55 into Syn61 yields no colonies containing the intact plasmid.

Example VI

EMBODIMENTS

The present disclosure provides a method for altering a cell, wherein the cell lacks expression of one or more tRNA cognate to one or more canonical codons or lacks expression of one or more release factors or otherwise lacks (1) one or more native genes operative to encode one or more tRNA cognate to one or more canonical codons thereby rendering the one or more canonical codons unassigned in the cell or (2) one or more native genes operative to encode one or more release factors The method includes introducing into the cell a foreign nucleic acid sequence of canonical codons encoding a polypeptide, wherein lack of the cell to produce (1) the one or more tRNA cognate to the one or more canonical codons or (2) the one or more release factors prevents expression of the foreign nucleic acid sequence into the polypeptide. According to one aspect, the cell is a eukaryotic cell. According to one aspect, the cell is a microbial cell. According to one aspect, the cell is a bacterial cell. According to one aspect, the cell is a yeast cell, a plant cell or a mammalian cell. According to one aspect, the cell is a human cell. According to one aspect, the polypeptide is a protein. According to one aspect, the polypeptide is toxic to the cell. According to one aspect, the polypeptide is toxic to the cell, wherein toxicity is determined by a reduction in cell growth rate by at least 1%, 10%, 50%, or 90% compared to growth rate of a corresponding wild type cell. According to one aspect, the polypeptide is a protein that is toxic to the cell. According to one aspect, the polypeptide is a protein that is toxic to the cell and wherein lack of the cell to produce (1) the one or more tRNA cognate to the one or more canonical codons or (2) the one or more release factors prevents expression of the foreign nucleic acid sequence into the polypeptide, thereby reducing toxicity to the cell of the polypeptide compared to a non-recoded cell of the same strain. According to one aspect, the cell is grown to produce a population of cells including the foreign nucleic acid sequence. According to one aspect, one or more tRNA cognate to the one or more unassigned codons are provided within the cell, and wherein the cell expresses the foreign nucleic acid sequence into the polypeptide.

The present disclosure provides a method for altering a cell including providing a cell with a foreign nucleic acid sequence of canonical codons encoding a polypeptide, wherein one or more canonical codon sequences within the foreign nucleic acid sequence are altered to produce one or more unassigned codons within the cell, wherein presence of the unassigned codon reduces or prevents expression of the foreign nucleic acid sequence into the polypeptide, wherein the unassigned codon is optionally located upstream of the nucleic acid sequence encoding the protein, wherein the unassigned codon is optionally located in a promoter cognate to the foreign nucleic acid sequence, or wherein the unassigned codon is optionally located within the open reading frame of the foreign nucleic acid sequence. According to one aspect, the cell is a eukaryotic cell. According to one aspect, the cell is a microbial cell. According to one aspect, the cell is a bacterial cell. According to one aspect, the cell is a yeast cell, a plant cell or a mammalian cell. According to one aspect, the cell is a human cell. According to one aspect, the polypeptide is a protein. According to one aspect, the polypeptide is toxic to the cell. According to one aspect, the polypeptide is toxic to the cell, wherein toxicity is determined by a reduction in cell growth rate by at least 1%, 10%, 50%, or 90% compared to growth rate of a corresponding wild type cell. According to one aspect, the polypeptide is a protein that is toxic to the cell. According to one aspect, the polypeptide is a protein that is toxic to the cell and wherein lack of the cell to produce (1) one or more tRNA cognate to the one or more unassigned codons or (2) the one or more release factors prevents expression of the foreign nucleic acid sequence into the polypeptide, thereby reducing toxicity to the cell of the polypeptide compared to a non-recoded cell of the same strain. According to one aspect, one or more tRNA cognate to the one or more unassigned codons are provided within the cell, and wherein the cell expresses the foreign nucleic acid sequence into the polypeptide. According to one aspect, the microbial cell is grown to produce a population of microbial cells including the foreign nucleic acid sequence.

The present disclosure provides a method for expressing a foreign nucleic acid sequence to produce a polypeptide in a cell, wherein the cell lacks expression of one or more tRNA cognate to one or more canonical codons or lacks expression of one or more release factors or otherwise lacks (1) one or more native genes operative to encode one or more tRNA cognate to one or more canonical codons within the foreign nucleic acid sequence or (2) one or more native genes operative to encode one or more release factors The method includes providing the cell with the foreign nucleic acid sequence, optionally providing the cell with an expression plasmid or vector that is expressed (1) to provide the one or more tRNA cognate to the one or more canonical codons within the foreign nucleic acid sequence or (2) the one or more release factors, wherein the cell translates the foreign nucleic acid sequence to produce the polypeptide, or optionally, wherein the cell is genetically modified to encode one or more tRNA cognate to one or more canonical codons within the foreign nucleic acid sequence under the influence of an inducible promoter and inducing the inducible promoter to begin translation of the foreign nucleic acid sequence to produce the polypeptide. According to one aspect, the (1) one or more genes encoding one or more tRNA cognate to one or more canonical codons within the foreign nucleic acid sequence or (2) one or more genes encoding one or more release factors are under the influence of a constitutive promoter. According to one aspect, the (1) one or more genes encoding one or more tRNA cognate to one or more canonical codons within the foreign nucleic acid sequence or (2) one or more genes encoding one or more release factors are under the influence of an inducible promoter. According to one aspect, the expression plasmid expresses (1) the one or more tRNA cognate to the one or more canonical codons within the foreign nucleic acid sequence or (2) the one or more release factors at a first temperature but does not express (1) the one or more tRNA cognate to the one or more canonical codons within the foreign nucleic acid sequence or (2) the one or more release factors at a second temperature that is higher than the first temperature. According to one aspect, the expression plasmid includes a resistance gene allowing selection of cells including the expression plasmid. According to one aspect, the expression plasmid includes a counterselectable gene allowing counterselection of cells including the expression plasmid. According to one aspect, the expression plasmid includes a nuclease cutting site. According to one aspect, (1) one or more native genes encoding one or more tRNA cognate to one or more canonical codons within the foreign nucleic acid sequence or (2) one or more native genes encoding one or more release factors are rendered inoperative by CRISPR-Cas9 mediated genome editing or removal of the (1) one or more native genes encoding one or more tRNA cognate to one or more canonical codons within the foreign nucleic acid sequence or (2) one or more native genes encoding one or more release factors. According to one aspect, the cell is grown to produce a population of cells including the foreign nucleic acid sequence. According to one aspect, the cell is a eukaryotic cell. According to one aspect, the cell is a microbial cell. According to one aspect, the cell is a bacterial cell. According to one aspect, the cell is a yeast cell, a plant cell or a mammalian cell. According to one aspect, the cell is a human cell. According to one aspect, the polypeptide is a protein. According to one aspect, the polypeptide is toxic to the cell. According to one aspect, the polypeptide is toxic to the cell, wherein toxicity is determined by a reduction in cell growth rate by at least 1%, 10%, 50%, or 90% compared to growth rate of a corresponding wild type cell. According to one aspect, the polypeptide is a protein that is toxic to the cell. According to one aspect, the polypeptide is a protein that is toxic to the cell and wherein lack of the cell to produce (1) one or more tRNA cognate to the one or more unassigned codons or (2) the one or more release factors prevents expression of the foreign nucleic acid sequence into the polypeptide, thereby reducing toxicity to the cell of the polypeptide compared to a non-recoded cell of the same strain.

The present disclosure provides an altered cell lacking expression of one or more tRNA cognate to one or more canonical codons or lacking expression of one or more release factors or otherwise lacking (1) one or more native genes operative to encode one or more tRNA cognate to one or more canonical codons or (2) one or more native genes operative to encode one or more release factors and including a foreign nucleic acid sequence of canonical codons encoding a polypeptide. According to one aspect, the cell is a eukaryotic cell. According to one aspect, the cell is a microbial cell. According to one aspect, the cell is a bacterial cell. According to one aspect, the cell is a yeast cell, a plant cell or a mammalian cell. According to one aspect, the cell is a human cell. According to one aspect, the polypeptide is a protein. According to one aspect, the polypeptide is toxic to the cell. According to one aspect, the polypeptide is toxic to the cell, wherein toxicity is determined by a reduction in cell growth rate by at least 1%, 10%, 50%, or 90% compared to growth rate of a corresponding wild type cell. According to one aspect, the polypeptide is a protein that is toxic to the cell. According to one aspect, the polypeptide is a protein that is toxic to the cell and wherein lack of the cell to produce (1) one or more tRNA cognate to the one or more unassigned codons or (2) the one or more release factors prevents expression of the foreign nucleic acid sequence into the polypeptide, thereby reducing toxicity to the cell of the polypeptide compared to a non-recoded cell of the same strain.

The present disclosure provides an altered cell including a foreign nucleic acid sequence of canonical codons encoding a polypeptide, wherein the foreign nucleic acid sequence is recoded to include one or more unassigned codons replacing one or more target canonical codons, wherein the unassigned codon is optionally located upstream of the foreign nucleic acid sequence encoding the protein, wherein the unassigned codon is optionally located in a promoter cognate to the foreign nucleic acid sequence, or wherein the unassigned codon is optionally located within the open reading frame of the foreign nucleic acid sequence. According to one aspect, the cell is a eukaryotic cell. According to one aspect, the cell is a microbial cell. According to one aspect, the cell is a bacterial cell. According to one aspect, the cell is a yeast cell, a plant cell or a mammalian cell. According to one aspect, the cell is a human cell. According to one aspect, the polypeptide is a protein. According to one aspect, the polypeptide is toxic to the cell. According to one aspect, the polypeptide is toxic to the cell, wherein toxicity is determined by a reduction in cell growth rate by at least 1%, 10%, 50%, or 90% compared to growth rate of a corresponding wild type cell. According to one aspect, the polypeptide is a protein that is toxic to the cell. According to one aspect, the polypeptide is a protein that is toxic to the cell and wherein lack of the cell to produce (1) one or more tRNA cognate to the one or more unassigned codons or (2) the one or more release factors prevents expression of the foreign nucleic acid sequence into the polypeptide, thereby reducing toxicity to the cell of the polypeptide compared to a non-recoded cell of the same strain.

The present disclosure provides an altered cell lacking expression of one or more tRNA cognate to one or more canonical codons or lacking expression of one or more release factors or otherwise lacking (1) one or more native genes operative to encode one or more tRNA cognate to one or more canonical codons within a foreign nucleic acid sequence encoding a polypeptide or (2) one or more native genes operative to encode one or more release factors and including the foreign nucleic acid sequence, an expression plasmid or vector encoding the one or more tRNA cognate to the one or more canonical codons within the foreign nucleic acid sequence or (2) the one or more release factors. According to one aspect, the cell is a eukaryotic cell. According to one aspect, the cell is a microbial cell. According to one aspect, the cell is a bacterial cell. According to one aspect, the cell is a yeast cell, a plant cell or a mammalian cell. According to one aspect, the cell is a human cell. According to one aspect, the polypeptide is a protein. According to one aspect, the polypeptide is toxic to the cell. According to one aspect, the polypeptide is toxic to the cell, wherein toxicity is determined by a reduction in cell growth rate by at least 1%, 10%, 50%, or 90% compared to growth rate of a corresponding wild type cell. According to one aspect, the polypeptide is a protein that is toxic to the cell. According to one aspect, the polypeptide is a protein that is toxic to the cell and wherein lack of the cell to produce (1) one or more tRNA cognate to the one or more unassigned codons or (2) the one or more release factors prevents expression of the foreign nucleic acid sequence into the polypeptide, thereby reducing toxicity to the cell of the polypeptide compared to a non-recoded cell of the same strain.

Sequence Listings:

```
pCTXVP60 (SEQ ID NO: 3)
GAATTCCGGATGAGCATTCATCAGGCGGGCAAGAATGTGAATAAAGGCCGGATAA
AACTTGTGCTTATTTTTCTTTACGGTCTTTAAAAAGGCCGTAATATCCAGCTGAACG
GTCTGGTTATAGGTACATTGAGCAACTGACTGAAATGCCTCAAAATGTTCTTTACGA
TGCCATTGGGATATATCAACGGTGGTATATCCAGTGATTTTTTTCTCCATTTTAGCTT
CCTTAGCTCCTGAAAATCTCGATAACTCAAAAAATACGCCCGGTAGTGATCTTATTT
CATTATGGTGAAAGTTGGAACCTCTTACGTGCCGATCAACGTCTCATTTTCGCCAAA
AGTTGGCCCAGGGCTTCCCGGTATCAACAGGGACACCAGGATTTATTTATTCTGCG
AAGTGATCTTCCGTCACAGGTATTTATTCGGCGCAAAGTGCGTCGGGTGATGCTGC
CAACTTACTGATTTAGTGTATGATGGTGTTTTTGAGGTGCTCCAGTGGCTTCTGTTTC
TATCAGCTGTCCCTCCTGTTCAGCTACTGACGGGGTGGTGCGTAACGGCAAAAGCA
CCGCCGGACATCAGCGCTAGCGGAGTGTATACTGGCTTACTATGTTGGCACTGATG
AGGGTGTCAGTGAAGTGCTTCATGTGGCAGGAGAAAAAAGGCTGCACCGGTGCGT
CAGCAGAATATGTGATACAGGATATATTCCGCTTCCTCGCTCACTGACTCGCTACGC
TCGGTCGTTCGACTGCGGCGAGCGGAAATGGCTTACGAACGGGGCGGAGATTTCCT
GGAAGATGCCAGGAAGATACTTAACAGGGAAGTGAGAGGGCCGCGGCAAAGCCGT
TTTTCCATAGGCTCCGCCCCCCTGACAAGCATCACGAAATCTGACGCTCAAATCAGT
GGTGGCGAAACCCGACAGGACTATAAAGATACCAGGCGTTTCCCCCTGGCGGCTCC
CTCGTGCGCTCTCCTGTTCCTGCCTTTCGGTTTACCGGTGTCATTCCGCTGTTATGGC
CGCGTTTGTCTCATTCCACGCCTGACACTCAGTTCCGGGTAGGCAGTTCGCTCCAAG
CTGGACTGTATGCACGAACCCCCCGTTCAGTCCGACCGCTGCGCCTTATCCGGTAAC
TATCGTCTTGAGTCCAACCCGGAAAGACATGCAAAAGCACCACTGGCAGCAGCCAC
TGGTAATTGATTTAGAGGAGTTAGTCTTGAAGTCATGCGCCGGTTAAGGCTAAACT
GAAAGGACAAGTTTTGGTGACTGCGCTCCTCCAAGCCAGTTACCTCGGTTCAAAGA
GTTGGTAGCTCAGAGAACCTTCGAAAAACCGCCCTGCAAGGCGGTTTTTTCGTTTTC
AGAGCAAGAGATTACGCGCAGACCAAAACGATCTCAAGAAGATCATCTTATTAGG
```

<div style="text-align:center">Sequence Listings:</div>

```
ATCTATTAATACGACTCACTATAGGGATCCCGGGCGCGCCGTCGACTTTAAAGTTC
ATCCTTTTCAGAAACATATGAAAATCCATTAGCAGTTCCTCCAAGATTAAAAACAA
GAGTAGACTTAGATGGTCTTGGTCCAACTGGTCTAACATCAATAAGTTCAGTAAGA
TCAATAAGAGTAGTAGAAGCTCCAGTTCCAGCATAAAAATATCCATCAACAGAAAG
TCCAATTTCCATGAATCCAGAAGCAAAAGTAAGTTGCCAAACAAAAAATTGTCCTG
GCATAAGAGCAGAAGAATAATTATTAAGAGAAAGTCCAATAGTAACTGGAAGTGG
TTGAGATCCAGTTCCATATTGAGTTCCATTAGCAGATCCAGCAGTAGCATTAACATC
TCCAGTTCTTCTAACAACAGAAGCAAACATAATTGGAGTATTCTTTCCAACTGGAG
CTGCAGCTGGAGTTCCTGGAGTAGTAACAATTCTATCTGGTTGTGGAGTATAAGTA
ATAGCATTAGCAGATGGAGTAGAAATAACTCCAGAAGCCATAACAAAAAGTCCAG
CTGGATTTTGAGCAGTTCCAGTAACAACAGCATAGATAGACTTAGCAACAGTTTGA
GATCCAGAAGTATTAGTAGTTGGTTGAAGATTTCCTGGAGCTCCAGTAGCAAATCC
AAGTTCATAAGCTTGAACAGTAGTAACATTTGGAGCTCCAGAATTAGAGTTCCAA
TAGCTCCAAATCCAACCCATCCAGCAGCTGGAATACCTGGTCCATTGAATGGAACA
AAAGACATATCTGGAAATCCATCTGGAGCAACTTGAGAAATTGGATTATCAATAGC
AGATCCAGCATTAGCATACCAAAATTGAAGAACATTAGTAGCATTAGATCCTGGAT
AAGAAGCAGATCCTCTTCTATGATCGATATCAGCAAATCTTGGAGAAGACCATCCA
TAAGTAGATCCATTAAGATTCCAATGTCTATTACAAGTAGAAAATCCTCCTGGAAC
TGGTTGAAGTCCAACAATTTGTCCATTCCATCTATTATCATTTCCAACTCCAGTAAG
AACTGGAGTAGTAAGAAGTCCAGCTGGATAGATAGAATCAACAGTCTTAGAAGAT
GGAGTTCTAATCATAACAAATTCAAAATCTTCAGATGGTCTAGTTTCAACAGTAACT
TGAATAGCAGAAGTAGATCCTCCAAATGGATTAATAAGATTATTATAAACAGAAAG
AACAAGAGTTGGAACAAGTCCTGGATCTCCAGTTGGATGATACATATTTGGTCTAA
GGTCTGGCATAGTAATAGTAACTGGTTCAAGAGACCTAGCATCAATAACAACATGT
GGAAATTGTCTAACTTCAAGACCTGGTCCAATTTCAATTCCTGGTGGAATAACAGC
AGCAACAAGTCTTCCTCCAAAAACTCCAGATCCAGCAACAATGAATCTGAATTGCA
TTCCTCCAGCCCATCCAGCATACATTTGAGAAAGAACAGCAGTGAATGGATTATTT
TGTGGAGAATGTTGAACAGTATAAAGAATAGATCCTGGAGCATCAGCAACAGACC
AAGTAAAAACATCATTATAATAAAAATTAGTTCTCCAAGTTTCTTGTTGATCAACTT
GTTGTGGTGGTCCTCCAATTCCAGCAGTAGCAATAGAAGCAGAAGAATTTTCAGCA
GTAACAACAGAAGTAGTAGCAACAACTCCTGGGTCCATTCCATCAGTAGTAGTTCC
TGGAACAGAAGCAGTAGTAGCAGTTCCAGCAGCTCCAGCTTGTGGAGCAGTTCTAG
CCTTTCCTTCCATGGGTCCTGGTCCATTAGCCATAGAAATAGCAGCAATAGCATGTG
GAGTCTTATTATTCCAAACACACAACTTTTCAACCTTAGCTTCAGTAAGATAAGCAA
TTCTAAGAGTATCCTTCATTCTTTCAATAGCCTTCTTTTGAGAATCAATATGTTGAG
ATCCTGGAACTTCAACTTGAAAAGTAGCTCCATTCTTAAAAGTAATAATAGCCATTT
CTCTCTTTCCAGCAAGAGATTCAGTATAAGAAAAAATCTTATCATTAAGAGTATGA
ATTTGAGTATTATGATATTCAGCACAAAGATCAGTAATATTTTGTGGAGTGGAGGA
AGCCATTGTCCCGGGCGGCCGCTTCTATAGTGTCACCTAAATCGGGTCGAATTTGCT
TTCGAATTTCTGCCATTCATCCGCTTATTATCACTTATTCAGGCGTACAACCAGGCG
TTTAAGGGCACCAATAACTGCCTTAAAAAAATTACGCCCCGCCCTGCCACTCATCG
CAGTACTGTTGTAATTCATTAAGCATTCTGCCGCACATGGAAGCCATCACAAACGGC
ATGATGAACCTGAATCGCCAGCGGCATCAGCACCTTGTCGCCTTGCGTATAATATTT
GCCCATAGTGAAAACGGGGGCGAAGAAGTTGTCCATATTGGCCACGTTTAAATCAA
AACTGGTGAAACTCACCCAGGGATTGGCTGAGACGAAAAACATATTCTCAATAAAC
CCTTTAGGGAAATAGGCCAGGTTTTCACCGTAACACGCCACATCTTGCGAATATAT
GTGTAGAAACTGCCGGAAATCGTCGTGGTATTCACTCCAGAGCGATGAAAACGTTT
CAGTTTGCTCATGGAAAACGGTGTAACAAGGGTGAACACTATCCCATATCACCAGC
TCACCGTCTTTCATTGCCATACG ptRNAsup (SEQ ID NO: 4)
TCATTAGTCTTCAATGACGTGTAAACCACGGCGCTTTAAGTCCTCTAACGAATCCAA
CATTCCCCTTATTAATTCAACAGGATGCCCCTCCCAGTCTTCAACAACGCCAACAAT
TCTCAAGGGTTCGCAGGTTCTATAGGACTGTGTTGGATTACCGGGAAATTTTTTGTT
CGTAAGATTCGGATCGTCTTCGAACGGTCCTGTTGGCTCAACTATGTATATGTAGCC
GCGACCCTCGAGGCCAGACAGTGACATAGCAAGTTCAGCTCCCCAAACTGCTGGCT
CCATCAAGGCTGAAAAGTAGATGTGCTTAAGAATACGACCGTCCTCGAAATGAGAG
ATGAACCCTGTGGTTAGCAAGTCACCAATCGCCAAATTGGCTTTGGTTCCATGATA
GAACGGTCCTTGCACCTGCTTGTAATTATCATGAGAGATGGGAATCCAATCTTTTAC
CATATAACGAACCTCCTCTTGCTTATTACAGCAACGCCGCGTCTGAATTATTTCTAG
AGAAGCATTTATCAGGGTTATTGTCTCATGAGCGGATACATATTTGAATGTATTTAG
AAAAATAAACAAATAGGGGTTCCGCGCACATTTCCCCGAAAAGTGCGAGTATTTAC
AACGAAGACGCAATCACTTTCTTGATCAGTGATCGTTTCGGCGTAATTTTCAGCAAA
CGATCAAAAGTGGTGAAAAATATCGTTGACTCATCGCGCCAGGTAAGTAGAATGCA
ACGCATCGAACGGCGGCACTGATTGCCAGACGATAATAAAATCAAGTGATTAACTG
ATTGCTTGATGAATCTTTCTTCCCGAGCCCGATGGTGGAATCGGTAGCACAAGG
GATTTAAAATCCCTCGGCGTTCGCGCTGTGCGGGTTCAAGTCCCGCTCCGGGTACCA
TGGGAAGATAAGAATAAAATCAAAGCAATAAGCAGTGTCCTCGGTACCAAATTTT
CGAAAAAAGACGCTGAAAAGCGTCTTTTTTCGTTTTGGTCCTTACAATCAGCAGTCA
GAACTTTTACGAAGAATAGTGGTCGCTCAACCTTTTCTGTTGATAAAACACTCTTTT
TGACGTTTTTACAGACTAATTGAACGTGAAGTGTGCAAACGATAAAAGTGTAGGAA
AAATTGTTTGACTTATAAGTCTCAGAAAGTAATATGTGCGCGACGCAGCGACGATG
AGCGATAAACAAGTTCTTCGAAGCACTCGTAAGAGGCGTGTGGTGAGGTGGCCGA
GAGGCTGAAGGCGCTCCCCTGCTAAGGGAGTATGCGGTCAAAAGCTGCATCCGGG
GTTCGAATCCCCGCCTCACCGCCATTTGCATCTAAAAAAAAACCCCGCCCCTGACA
GGGCGGGGTTTTTTTTTTAATTATAGGGATAACAGGGTAATATATTCACTTCCCTCA
CAGATTCGTTCAGAGATAAAAGCGTTGGTAACAGTTGCCTGGAGTGTGACAAAGCG
```

-continued

---

Sequence Listings:

---

TTACACATCGCTGTATGCAATGCTGAAAATTTCAGCACTTAGCGAGGTGCGAGCAA
GCTGGCGCTTGCATGGTGGCGTGCGACAGGTATAATCCACAACGTTTTCGCGCATA
CCTCTTCAGTGCCGAAGTGGCGAAATCGGTAGACGCAGTTGATTCAAAATCAACCG
TAGAAATACGTGCCGGTTCGAGTCCGGCCTTCGGCACCAAAAGTATGTAAATAGAC
CTCAACTGAGGTCTTTTTTTATGCCAATTATTGAAGGCCGCTAACGCGGCCTTTTTTT
GTTTCTGGTCTCCCTGCGGATAAAGTTGATACCCTTACCTGAGTTCTTCTGAAAATA
ACGGACTAAAAAGCAGAACGTGCGCGAAAACATTAAGAAAAATTATAAAAACCCG
GCATAAATGGCGAGGGTTTAAGCAATCGAGCGGCAGCGTACTTACCCCGCACTCGA
TTAGCGGGTATACTCATGCCGCATTGTCCTCTTAGTTAAATGGATATAACGAGCCCC
TCCTAAGGGCTAATTGCAGGTTCGATTCCTGCAGGGGACACCATTTATCAGTTCGCT
CCCATCCGTACCAGTCCGCAAAATCCAACGCATGAGAAAGCCCCCGGAAGATCACC
TTCCGGGGGCTTTTTTATTGCGCTGAAAAGCAATCCCTCGTGAAGTAACTCAATAGT
GTTCTCTGGTATCGTAGTGTGCGTTTGTTTGCCGCTATAGCGAAATAAATCAGAAAA
TCAGACGCGGTCGTTCACTTGTTCAGCAACCAGATCAAAAGCCATTGACTCAGCAA
GCGTTGACCGTATAATTCACGCGATTACACGCGCATTGCGGTATCAACGCGCCCTT
AGCTCAGTTGGATAGAGCAACGACCTTCTAAGTCGTGGGCCGCAGGTTCGAATCCT
GCAGGGCGCGCCATTACAATTCAATCAGTTACGCCTTCTTTATATCCTCCATAAGAA
AAAAGCCCGCACCTGACAGTGCGGGCTTTTTTTTTCGATCACTTCTGGAAGCTTGAG
CACGTGTTGACAATTAATCATCGGCATAGTATATCGGCATAGTATAATACGACAAG
GTGAGGAACTAAACCCCTATAACCCACTAAGAAGAATTTATGTCACATCTCGCAGA
ACTGGTTGCCTCAGCGAAGGCGGCCATTTCACAGGCGTCAGATGTTGCCGCGCTTG
ATAATGTGCGCGTCGAATATCTAGGTAAAAAAGGGCACCTAACCCTTCAGATGACG
ACCCTGCGTGAGCTGCCGCCAGAAGAGCGTCCGGCAGCTGGTGCGGTTATCAACGA
AGCGAAAGAGCAGGTTCAGCAGGCGCTGAATGCGCGTAAAGCGGAACTGGAATCC
GCTGCACTGAATGCGCGTCTGGCGGCGGAAACGATTGATGTCTCTCTGCCAGGTCG
TCGCATTGAAAACGGCGGTCTGCATCCGGTTACCCGTACCATCGACCGTATCGAAT
CATTCTTCGGTGAGCTTGGCTTTACCGTGGCAACCGGGCCGGAAATCGAAGACGAT
TATCATAACTTCGATGCTCTGAACATTCCTGGTCACCACCCGGCGCGAGCTGACCAC
GACACTTTCTGGTTTGACACTACCCGCCTGCTGCGTACCCAGACCTCTGGCGTACAG
ATCCGCACCATGAAAGCCCAGCAGCCACCGATTCGTATCATCGCGCCTGGCCGTGT
TTATCGTAACGACTACGACCAGACTCACACGCCGATGTTCCATCAGATGGAAGGTC
TGATTGTTGATACCAACATCTCCTTTACCAACCTGAAAGGCACGTGCACGACTTCC
TGCGTAACTTCTTTGAGGAAGATCTCCAGATTCGCTTCCGTCCTTCCTACTTCCCGTT
TGCCGAACCTTCTGCAGAAGTGGACGTCATGGGTAAAAACGGTAAATGGCTGGAA
GTGCTGGGCTGCGGGATGGTGCATCCGAACGTGCTTCGTAACGTTGGCATCGACCC
GGAAGTTTACTCTGGTTTCGGCTTCGGGATGGGGATGGAGCGTCTGACTATGCTAC
GTTACGGCGTCACCGACCTGCGTTCATTCTTCGAAAACGATCTGCGTTTCCTCAAAC
AGTTTAAATAACATTACCCTGTTATCCCTAAATAAGATTTACGGATTACTATCTTTT
CGAAAAAAGGCCTCCCAAATCGGGGGGCCTTTTTTATTGATAACAAAATCCATGGG
TATGGACAGTTTTCCCTTTGATATGTAACGGTGAACAGTTGTTCTACTTTTGTTTGTT
AGTCTTGATGCTTCACTGATAGATACAAGAGCCATAAGAACCTCAGATCCTTCCGT
ATTTAGCCAGTATGTTCTCTAGTGTGGTTCGTTGTTTTTGCGTGAGCCATGAGAACG
AACCATTGAGATCATACTTACTTTGCATGTCACTCAAAAATTTTGCCTCAAAACTGG
TGAGCTGAATTTTTGCAGTTAAAGCATCGTGTAGTGTTTTTCTTAGTCCGTTACGTA
GGTAGGAATCTGATGTAATGGTTGTTGGTATTTTGTCACCATTCATTTTTATCTGGTT
GTTCTCAAGTTCGGTTACGAGATCCATTTGTCTATCTAGTTCAACTTGGAAAATCAA
CGTATCAGTCGGGCGGCCTCGCTTATCAACCACCAATTTCATATTGCTGTAAGTGTT
TAAATCTTTACTTATTGGTTTCAAAACCCATTGGTTAAGCCTTTTAAACTCATGGTA
GTTATTTTCAAGCATTAACATGAACTTAAATTCATCAAGGCTAATCTCTATATTTGC
CTTGTGAGTTTTCTTTTGTGTTAGTTCTTTTAATAACCACTCATAAATCCTCATAGAG
TATTTGTTTTCAAAAGACTTAACATGTTCCAGATTATATTTTATGAATTTTTTTTAACT
GGAAAAGATAAGGCAATATCTCTTCACTAAAAACTAATTCTAATTTTTCGCTTGAG
AACTTGGCATAGTTTGTCCACTGGAAAATCTCAAAGCCTTTAACCAAAGGATTCCT
GATTTCCACAGTTCTCGTCATCAGCTCTCTGGTTGCTTTAGCTAATACACCATAAGC
ATTTTCCCTACTGATGTTCATCATCTGAGCGTATTGGTTATAAGTGAACGATACCGT
CCGTTCTTTCCTTGTAGGGTTTTCAATCGTGGGGTTGAGTAGTGCCACACAGCATAA
AATTAGCTTGGTTTCATGCTCCGTTAAGTCATAGCGACTAATCGCTAGTTCATTTGC
TTTGAAAACAACTAATTCAGACATACATCTCAATTGGTCTAGGTGATTTTAATCACT
ATACCAATTGAGATGGGCTAGTCAATGATAATTACTAGTCCTTTTCCTTTGAGTTGT
GGGTATCTGTAAATTCTGCTAGACCTTTGCTGGAAAACTTGTAAATTCTGCTAGACC
CTCTGTAAATTCCGCTAGACCTTTGTGTGTTTTTTTTGTTTATATTCAAGTGGTTATA
ATTTATAGAATAAAGAAAGAATAAAAAAAGATAAAAAGAATAGATCCCAGCCCTG
TGTATAACTCACTACTTTAGTCAGTTCCGCAGTATTACAAAAGGATGTCGCAAACG
CTGTTTGCTCCTCTACAAAACAGACCTTAAAACCCTAAAGGCTTAAGTAGCACCCTC
GCAAGCTCGGTTGCGGCCGCAATCGGGCAAATCGCTGAATATTCCTTTTGTCTCCGA
CCATCAGGCACCTGAGTCGCTGTCTTTTTCGTGACATTCAGTTCGCTGCGCTCACGG
CTCTGGCAGTGAATGGGGGTAAATGGCACTACAGGCGCCTTTTATGGATTCATGCA
AGGAAACTACCCATAATACAAGAAAAGCCCGTCACGGGCTTCTCAGGGCGTTTTAT
GGCGGGTCTGCTATGTGGTGCTATCTGACTTTTTGCTGTTCAGCAGTTCCTGCCCTCT
GATTTTCCAGTCTGACCACTTCGGATTATCCCGTGACAGGTCATTCAGACTGGCTAA
TGCACCCAGTAAGGCAGCGGTATCATCAACGGGGTCTGACGCTCAGTGGAACGAA
AACTCACGTTAAGGGATTTTGGTCATGAGATTATCAAAAAGGATCTTCACCTAGAT
CCTTTTAAATTAAAAATGAAGTTTTAAATCAATCTAAAGTATATATGAGTAAACTTG
GTCTGACTAGGGATAACAGGGTAAT

CTXVP60_-_orf238 (SEQ ID NO: 5)
ATGCTATTGCTGCTATTTCTATGGCTAATGGACCAGGACCCATGGAAGGAAAGGCT Sequence Listings:

```
AGAACTGCTCCACAAGCTGGAGCTGCTGGAACTGCTACTACTGCTTCTGTTCCAGG
AACTACTACTGATGGAATGGACCCAGGAGTTGTTGCTACTACTTCTGTTGTTACTGC
TGAAAATTCTTCTGCTTCTATTGCTACTGCTGGAATTGGAGGACCACCACAACAAGT
TGATCAACAAGAAACTTGGAGAACTAATTTTTATTATAATGATGTTTTTACTTGGTC
TGTTGCTGATGCTCCAGGATCTATTCTTTATACTGTTCAACATTCTCCACAAAATAA
TCCATTCACTGCTGTTCTTTCTCAAATGTATGCTGGATGGGCTGGAGGAATGCAATT
CAGATTCATTGTTGCTGGATCTGGAGTTTTTGGAGGAAGACTTGTTGCTGCTGTTAT
TCCACCAGGAATTGAAATTGGACCAGGTCTTGAAGTTAGACAATTTCCACATGTTG
TTATTGATGCTAGGTCTCTTGAACCAGTTACTATTACTATGCCAGACCTTAGACCAA
ATATGTATCATCCAACTGGAGATCCAGGACTTGTTCCAACTCTTGTTCTTTCTGTTTA
TAATAATCTTATTAATCCATTTGGAGGATCTACTTCTGCTATTCAAGTTACTGTTGA
AACTAGACCATCTGAAGATTTTGAATTTGTTATGA
``` hGHR_wt (SEQ ID NO: 6)

```
ATGGATCTCTGGCAGCTGCTGTTGACCTTGGCACTGGCAGGATCAAGTGATGCTTTT
TCTGGAAGTGAGGCCACAGCAGCTATCCTTAGCAGAGCACCCTGGAGTCTGCAAAG
TGTTAATCCAGGCCTAAAGACAAATTCTTCTAAGGAGCCTAAATTCACCAAGTGCC
GTTCACCTGAGCGAGAGACTTTTTCATGCCACTGGACAGATGAGGTTCATCATGGT
ACAAAGAACCTAGGACCCATACAGCTGTTCTATACCAGAAGGAACACTCAAGAAT
GGACTCAAGAATGGAAAGAATGCCCTGATTATGTTTCTGCTGGGGAAAACAGCTGT
TACTTTAATTCATCGTTTACCTCCATCTGGATACCTTATTGTATCAAGCTAACTAGC
AATGGTGGTACAGTGGATGAAAGTGTTTCTCTGTTGATGAAATAGTGCAACCAGA
TCCACCCATTGCCCTCAACTGGACTTTACTGAACGTCAGTTTAACTGGGATTCATGC
AGATATCCAAGTGAGATGGGAAGCACCACGCAATGCAGATATTCAGAAAGGATGG
ATGGTTCTGGAGTATGAACTTCAATACAAAGAAGTAAATGAAACTAAATGGAAAT
GATGGACCCTATATTGACAACATCAGTTCCAGTGTACTCATTGAAAGTGGATAAGG
AATATGAAGTGCGTGTGAGATCCAAACAACGAAACTCTGGAAATTATGGCGAGTTC
AGTGAGGTGCTCTATGTAACACTTCCTCAGATGAGCCAATTTACATGTGAAGAAGA
TTTCTACTTTCCATGGCTCTTAATTATTATCTTTGGAATATTTGGGCTAACAGTGATG
CTATTTGTATTCTTATTTTCTAAACAGCAAAGGATTAAAATGCTGATTCTGCCCCCA
GTTCCAGTTCCAAAGATTAAAGGAATCGATCCAGATCTCCTCAAGGAAGGAAAATT
AGAGGAGGTGAACACAATCTTAGCCATTCATGATAGCTATAAACCCGAATTCCACA
GTGATGACTCTTGGGTTGAATTTATTGAGCTAGATATTGATGAGCCAGATGAAAAG
ACTGAGGAATCAGACACAGACAGACTTCTAAGCAGTGACCATGAGAAATCACATA
GTAACCTAGGGGTGAAGGATGGCGACTCTGGACGTACCAGCTGTTGTGAACCTGAC
ATTCTGGAGACTGATTTCAATGCCAATGACATACATGAGGGTACCTCAGAGGTTGC
TCAGCCACAGAGGTTAAAAGGGGAAGCAGATCTCTTATGCCTTGACCAGAAGAATC
AAAATAACTCACCTTATCATGATGCTTGCCCTGCTACTCAGCAGCCCAGTGTTATCC
AAGCAGAGAAAAACAAACCACAACCACTTCCTACTGAAGGAGCTGAGTCAACTCA
CCAAGCTGCCCATATTCAGCTAAGCAATCCAAGTTCACTGTCAAACATCGACTTTTA
TGCCCAGGTGAGCGACATTACACCAGCAGGTAGTGTGGTCCTTTCCCCGGGCCAAA
AGAATAAGGCAGGGATGTCCCAATGTGACATGCACCCGGAAATGGTCTCACTCTGC
CAAGAAAACTTCCTTATGGACAATGCCTACTTCTGTGAGGCAGATGCCAAAAGTG
CATCCCTGTGGCTCCTCACATCAAGGTTGAATCACACATACAGCCAAGCTTAAACC
AAGAGGACATTTACATCACCACAGAAAGCCTTACCACTGCTGCTGGGAGGCCTGGG
ACAGGAGAACATGTTCCAGGTTCTGAGATGCCTGTCCCAGACTATACCTCCATTCAT
ATAGTACAGTCCCCACAGGGCCTCATACTCAATGCGACTGCCTTGCCCTTGCCTGAC
AAAGAGTTTCTCTCATCATGTGGCTATGTGAGCACAGACCAACTGAACAAAATCAT
GCCTTAG
``` pUC-hGHR_wt-RC55 (SEQ ID NO: 7)

```
TTATATTATTTTTGCCAAATAATTTTTAACAAAAGCTCTGAAGTCTTCTTCATTTAAA
TTCTTAGATGATACTTCATCTGGAAAATTGTCCCAATTAGTAGCATCACGCTGTGAG
TAAGTTCTAAACCATTTTTTTATTGTTGTATTATCTCTAATCTTACTACTCGATGAGT
TTTCGGTATTATCTCTATTTTTAACTTGGAGCAGGTTCCATTCATTGTTTTTTTTCATC
ATAGTGAATAAAATCAACTGCTTTAACACTTGTGCCTGAACACCATATCCATCCGG
CGTAATACGACTCACTATAGGGAGAGCGGCCGCCAGATCTTCCGGATGGCTCGAGT
TTTTCAGCAAGATATGGATCTCTGGCAGCTGCTGTTGACCTTGGCACTGGCAGGATC
AAGTGATGCTTTTTCTGGAAGTGAGGCCACAGCAGCTATCCTTAGCAGAGCACCCT
GGAGTCTGCAAAGTGTTAATCCAGGCCTAAAGACAAATTCTTCTAAGGAGCCTAAA
TTCACCAAGTGCCGTTCACCTGAGCGAGAGACTTTTTCATGCCACTGGACAGATGA
GGTTCATCATGGTACAAAGAACCTAGGACCCATACAGCTGTTCTATACCAGAAGGA
ACACTCAAGAATGGACTCAAGAATGGAAAGAATGCCCTGATTATGTTTCTGCTGGG
GAAAACAGCTGTTACTTTAATTCATCGTTTACCTCCATCTGGATACCTTATTGTATC
AAGCTAACTAGCAATGGTGGTACAGTGGATGAAAGTGTTTCTCTGTTGATGAAAT
AGTGCAACCAGATCCACCCATTGCCCTCAACTGGACTTTACTGAACGTCAGTTTAAC
TGGGATTCATGCAGATATCCAAGTGAGATGGGAAGCACCACGCAATGCAGATATTC
AGAAAGGATGGATGGTTCTGGAGTATGAACTTCAATACAAAGAAGTAAATGAAAC
TAAATGGAAAATGATGGACCCTATATTGACAACATCAGTTCCAGTGTACTCATTGA
AAGTGGATAAGGAATATGAAGTGCGTGTGAGATCCAAACAACGAAACTCTGGAAA
TTATGGCGAGTTCAGTGAGGTGCTCTATGTAACACTTCCTCAGATGAGCCAATTTAC
ATGTGAAGAAGATTTCTACTTTCCATGGCTCTTAATTATTATCTTTGGAATATTTGG
GCTAACAGTGATGCTATTTGTATTCTTATTTTCTAAACAGCAAAGGATTAAAATGCT
GATTCTGCCCCCAGTTCCAGTTCCAAAGATTAAAGGAATCGATCCAGATCTCCTCA
AGGAAGGAAAATTAGAGGAGGTGAACACAATCTTAGCCATTCATGATAGCTATAA
ACCCGAATTCCACAGTGATGACTCTTGGGTTGAATTTATTGAGCTAGATATTGATGA
GCCAGATGAAAAGACTGAGGAATCAGACACAGACAGACTTCTAAGCAGTGACCAT
```

-continued

---

Sequence Listings:

---

```
GAGAAATCACATAGTAACCTAGGGGTGAAGGATGGCGACTCTGGACGTACCAGCT
GTTGTGAACCTGACATTCTGGAGACTGATTTCAATGCCAATGACATACATGAGGGT
ACCTCAGAGGTTGCTCAGCCACAGAGGTTAAAAGGGGAAGCAGATCTCTTATGCCT
TGACCAGAAGAATCAAAATAACTCACCTTATCATGATGCTTGCCCTGCTACTCAGC
AGCCCAGTGTTATCCAAGCAGAGAAAAACAAACCACAACCACTTCCTACTGAAGG
AGCTGAGTCAACTCACCAAGCTGCCCATATTCAGCTAAGCAATCCAAGTTCACTGT
CAAACATCGACTTTTATGCCCAGGTGAGCGACATTACACCAGCAGGTAGTGTGGTC
CTTTCCCCGGGCCAAAAGAATAAGGCAGGGATGTCCCAATGTGACATGCACCCGGA
AATGGTCTCACTCTGCCAAGAAAACTTCCTTATGGACAATGCCTACTTCTGTGAGGC
AGATGCCAAAAAGTGCATCCCTGTGGCTCCTCACATCAAGGTTGAATCACACATAC
AGCCAAGCTTAAACCAAGAGGACATTTACATCACCACAGAAAGCCTTACCACTGCT
GCTGGGAGGCCTGGGACAGGAGAACATGTTCCAGGTTCTGAGATGCCTGTCCCAGA
CTATACCTCCATTCATATAGTACAGTCCCCACAGGGCCTCATACTCAATGCGACTGC
CTTGCCCTTGCCTGACAAAGAGTTTCTCTCATCATGTGGCTATGTGAGCACAGACCA
ACTGAACAAAATCATGCCTTAGATCTTTCTAGAAGATCTCCTACAATATTCTCAGCT
GCCATGGAAAATCGATGTTCTTCTTTTATTCTCTCAAGATTTTCAGGCTGTATATTA
AAACTTATATTAAGAACTATGCTAACCACCTCATCAGGAACCGTTGTAGGTGGCGT
GGGTTTTCTTGGCAATCGACTCTCATGAAAACTACGAGCTAAATATTCAATATGTTC
CTCTTGACCAACTTTATTCTGCATTTTTTTTGAACGAGGTTTAGAGCAAGCTTCAGG
AAACTGAGACAGGAATTTTATTAAAAATTTAAATTTTGAAGAAAGTTCAGGGTTAA
TAGCATCCATTTTTTGCTTTGCAAGTTCCTCAGCATTCTTAACAAAAGACGTCTCTTT
TGACATGTTTAAAGTTTAAACCTCCTGTGTGAAATTGTTATCCGCTCACAATTCCAC
ACATTATACGAGCCGGAAGCATAAAGTGTAAAGCCTGGGGTGCCTAATGAGTGAG
CTAACTCACATTAATTGCGTTGCGCTCACTGCCAATTGCTTTCCAGTCGGGAAACCT
GTCGTGCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAGAAGATCC
TTTGATCTTTTCTACGGGGTCTGACGCTCAGTGGAACGAAAACTCACGTTAAGGGA
TTTTGGTCATGAGATTATCAAAAAGGATCTTCACCTAGATCCTTTTAAATTAAAAAT
GAAGTTTTAAATCAATCTAAAGTATATATGAGTAAACTTGGTCTGACAGTTACCAA
TGCTTAATCAGAGAGGCACCTATCTCAGCGATCTGGCGATTTCGTTCATCCATAGTT
GCCTGGGACCCCGTCGTGTAGATAACTACGATACGGGAGGGCTTACCATCTGGCCC
CAGTGCTGCAATGATACCGCGAGACCCACGCTCACCGGCTCCAGATTTATCAGCAA
TAAACCAGCCAGCCGGAAGGGCGGAGCGCAGAAGTGGTCCTGCAACTTTATCCGCC
TCCATCCAGTCTATCAGTTGTTGCCGGGAAGCTAGAGTAAGTAGTTCGCCAGTTAGT
AGTTTGCGCAGCGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCC
ATGTTGTGCAGAAAAGCGGTTAGCTCCTTCGGTCCTCCGATCGTTGTCAGAAGCAG
GTTGGCCGCAGTGTTATCAGACATGGTTATGGCAGCAGAGCACAGTTCGCGTACTG
TCATGCCATCCGTAAGATGCTTTTCTGTGACTGGGGAGTACTCAACGAGGTCATTCT
GAGAATAGTGTATGCGGCGACCGAGTTGCTCTTGCCCGGCGTCAATACGGGACAGT
ACCGCGCCACATAGCAGAACTTTAAAAGTGGACATCATTGGAAAACGTTCTTCGGG
GCGAAAGGACTCAAGGATCTTACCAGAGTTGAGATCCAGTTCGATGTAACCCACTC
GTGCACCTAGCTGATCTTCAGCATCTTTTACTTTCACCAGCGTTTCTGGGTGAGCAA
AAACAGGAAGGCAAAATGCCGCAAAAAAGGGAATAAGGGCGACACGGAAATGTT
GAATGGACATCGTAGGGTAACCTGAATATTATTGAAGCATTTATCAGGGTTATTGT
CTCATGAGCGGATACATATTTGAATGTATTTAGAAAAATAAACAAATAGGGGTTCC
GCGCACATTTCCCCGAAAAGTGCCACCT
``` p15A-hGHR_wt-RC55 (SEQ ID NO: 13)
```
CCAATTATTGAAGGCCGCTAACGCGGCCTTTTTTTGTTTCTGGTCTCCCTCTATCAGC
TGTCCCTCCTGTTCAGCTACTGACGGGGTGGTGCGTAACGGCAAAAGCACCGCCGG
ACATCAGCGCTAGCGGAGTGTATACTGGCTTACTATGTTGGCACTGATGAGGGTGT
CAGTGAAGTGCTTCATGTGGCAGGAGAAAAAAGGCTGCACCGGTGCGTCAGCAGA
ATATGTGATACAGGATATATTCCGCTTCCTCGCTCACTGACTCGCTACGCTCGGTCG
TTCGACTGCGGCGAGCGGAAATGGCTTACGAACGGGGCGGAGATTTCCTGGAAGAT
GCCAGGAAGATACTTAACAGGGAAGTGAGAGGGCCGCGGCAAAGCCGTTTTTCCA
TAGGCTCCGCCCCCCTGACAAGCATCACGAAATCTGACGCTCAAATCAGTGGTGGC
GAAACCCGACAGGACTATAAAGATACCAGGCGTTTCCCCTGGCGGCTCCCTCGTG
CGCTCTCCTGTTCCTGCCTTTCGGTTTACCGGTGTCATTCCGCTGTTATGGCCGCGTT
TGTCTCATTCCACGCCTGACACTCAGTTCCGGGTAGGCAGTTCGCTCCAAGCTGGAC
TGTATGCACGAACCCCCCGTTCAGTCCGACCGCTGCGCCTTATCCGGTAACTATCGT
CTTGAGTCCAACCCGGAAAGACATGCAAAAGCACCACTGGCAGCAGCCACTGGTA
ATTGATTTAGAGGAGTTAGTCTTGAAGTCATGCGCCGGTTAAGGCTAAACTGAAAG
GACAAGTTTTGGTGACTGCGCTCCTCCAAGCCAGTTACCTCGGTTCAAAGAGTTGGT
```

-continued

Sequence Listings:

```
AGCTCAGAGAACCTTCGAAAAACCGCCCTGCAAGGCGGTTTTTTCGTTTTCAGAGC
AAGAGATTACGCGCAGACCAAAACGATCTCAAGAAGATCATCTTATTAATCAGATA
AAATATTTCTAGATTTCAGTGCAATTTATCTCTTCAAATGTAGCACCTGAAGTCAGC
CCCATACGATATAAGTTGTACCACCGTCAAAAAAAACGGCGCTTTTTAGCGCCGTT
TTTATTTTTCAACCTTTTAGGACAGCTTGACGGCTACATCATTCACTTTTTCTTCACA
ACCGGCACGGAACTCGGACGGAGAGGCCCCGGTGCATTTTTTAAATACCCGAGAGA
AATAGAGTTGATCGTCAAAACCAACATTGCGACCGACGGTGGCGATAGGCATCCGG
GTGGTGGACAGAAGCAGCTTCGCCTGAGAGATACGTTGGTCCTCGCGCCAGGACAG
GACAGAAATCCCGAGCTGCTGGCGGAAAAGATGAGACAGACGAGACGGAGAGAG
GCAAACATGCTGTGCGACAGAGGCGATATCAAAATTAGAGTCTGCCAGGTGATCAG
AGATGTACTGACAAGCCTCGCGTACCCGATTATCCATCGGTGGATGGAGGGACTCG
TTAATCGCTTCCATGCGCCGCAGAAGTAGTTGCTCAAGCAGATTTATCGCCAGCAG
CTCAGAATAGCGCCCTTCCCCTTGCCCGGCGTTAATGATTTGCCCAAACAGGTCGG
AGAAATGCGGCTGGTGCGCTTCATCCGGGCGAAAGAACCCCGTATTGGCAAATATA
GACGGCCAGTTAAGCCATTCATGCCAGTAGGCGCGCGGACGAAAGTAAACCCACT
GGTGATACCATTCGCGAGCCTCCGGATGACGACCGTAGTGATGAATCTCTCCTGGC
GGGAACAGAAGAATATCACCCGGTCGGCAAACAAATTCTCGTCCCTGATTTTTCAC
CACCCCCTGACCGCGAATGGTGAGATTGAGAATATAACCTTTCATTCCCAGCGGTC
GGTCGATAAAAAAATCGAGATAACCGTTGGCCTCAATCGGCGTAAGACCCGCCACC
AGATGGGCATTAAAAGAGTATCCCGGCAGCAGGGGATCATTTTGCGCTTCAGCCAT
ACTTTTCATACTCCCGCCATTCAGAGAAGAAACCAATTGTCCATATTGCATCAGACA
TTGCCGTCACTGCGTCTTTTACTGGCTCTTCTCGCTAACCAAACCGGTAACCCCGCT
TATTAAAAGCATTCTGTAACAAAGCGGGACCAAAGCCATGACAAAAACGCGTAAC
AAAAGTGTCTATAATCACGGCAGAAAAGTCCACATTGATTATTTGCACGGCGTCAC
ACTTTGCTATGCCATAGCATTTTTATCCATAAGATTAGCGGATCCTACCTGACGCTT
TTTATCGCAACTCTCTACTGTTTCTCCATACCCATGGATCTCTGGCAGCTGCTGTTGA
CCTTGGCACTGGCAGGATCAAGTGATGCTTTTTCTGGAAGTGAGGCCACAGCAGCT
ATCCTTAGCAGAGCACCCTGGAGTCTGCAAAGTGTTAATCCAGGCCTAAAGACAAA
TTCTTCTAAGGAGCCTAAATTCACCAAGTGCCGTTCACCTGAGCGAGAGACTTTTTC
ATGCCACTGGACAGATGAGGTTCATCATGGTACAAAGAACCTAGGACCCATACAGC
TGTTCTATACCAGAAGGAACACTCAAGAATGGACTCAAGAATGGAAAGAATGCCCT
GATTATGTTTCTGCTGGGGAAAACAGCTGTTACTTTAATTCATCGTTTACCTCCATC
TGGATACCTTATTGTATCAAGCTAACTAGCAATGGTGGTACAGTGGATGAAAAGTG
TTTCTCTGTTGATGAAATAGTGCAACCAGATCCACCCATTGCCCTCAACTGGACTTT
ACTGAACGTCAGTTTAACTGGGATTCATGCAGATATCCAAGTGAGATGGGAAGCAC
CACGCAATGCAGATATTCAGAAAGGATGGATGGTTCTGGAGTATGAACTTCAATAC
AAAGAAGTAAATGAAACTAAATGGAAAATGATGGACCCTATATTGACAACATCAG
TTCCAGTGTACTCATTGAAAGTGGATAAGGAATATGAAGTGCGTGTGAGATCCAAA
CAACGAAACTCTGGAAATTATGGCGAGTTCAGTGAGGTGCTCTATGTAACACTTCC
TCAGATGAGCCAATTTACATGTGAAGAAGATTTCTACTTTCCATGGCTCTTAATTAT
TATCTTTGGAATATTTGGGCTAACAGTGATGCTATTTGTATTCTTATTTTCTAAACAG
CAAAGGATTAAAATGCTGATTCTGCCCCCAGTTCCAGTTCCAAAGATTAAAGGAAT
CGATCCAGATCTCCTCAAGGAAGGAAAATTAGAGGAGGTGAACACAATCTTAGCC
ATTCATGATAGCTATAAACCCGAATTCCACAGTGATGACTCTTGGGTTGAATTTATT
GAGCTAGATATTGATGAGCCAGATGAAAAGACTGAGGAATCAGCACAGACAGAC
TTCTAAGCAGTGACCATGAGAAATCACATAGTAACCTAGGGGTGAAGGATGGCGA
CTCTGGACGTACCAGCTGTTGTGAACCTGACATTCTGGAGACTGATTTCAATGCCAA
TGACATACATGAGGGTACCTCAGAGGTTGCTCAGCCACAGAGGTTAAAAGGGGGAA
GCAGATCTCTTATGCCTTGACCAGAAGAATCAAAATAACTCACCTTATCATGATGCT
TGCCCTGCTACTCAGCAGCCCAGTGTTATCCAAGCAGAGAAAAACAAACCACAACC
ACTTCCTACTGAAGGAGCTGAGTCAACTCACCAAGCTGCCCATATTCAGCTAAGCA
ATCCAAGTTCACTGTCAAACATCGACTTTTATGCCCAGGTGAGCGACATTACACCA
GCAGGTAGTGTGGTCCTTTCCCCGGGCCAAAAGAATAAGGCAGGGATGTCCCAATG
TGACATGCACCCGGAAATGGTCTCACTCTGCCAAGAAAACTTCCTTATGGACAATG
CCTACTTCTGTGAGGCAGATGCCAAAAAGTGCATCCCTGTGGCTCCTCACATCAAG
GTTGAATCACACATACAGCCAAGCTTAAACCAAGAGGACATTTACATCACCACAGA
AAGCCTTACCACTGCTGCTGGGAGGCCTGGGACAGGAGAACATGTTCCAGGTTCTG
AGATGCCTGTCCCAGACTATACCTCCATTCATATAGTACAGTCCCCACAGGGCCTCA
TACTCAATGCGACTGCCTTGCCCTTGCCTGACAAAGAGTTTCTCTCATCATGTGGCT
ATGTGAGCACAGACCAACTGAACAAAATCATGCCTTAGAGTCAAAAGCCTCCGACC
GGAGGCTTTTGACTCCTGTTGATACCGGGAAGCCCTGGGCCAACTTTTGGCGAAAA
TGAGACGTTGATCGGCACGTAAGAGGTTCCAACTTTCACCATAATGAAATAAGATC
ACTACCGGGCGTATTTTTTGAGTTATCGAGATTTTCAGGAGCTAAGGAAGCTAAAA
TGGAGAAAAAATCACTGGATATACCACCGTTGATATATCCCAATGGCATCGTAAA
GAACATTTTGAGGCATTTCAGTCCGTTGCTCAATGTACCTATAACCAGACCGTTCAG
CTGGATATTACGGCCTTTCTGAAGACCGTAAAGAAAAATAAGCACAAGTTTTATCC
GGCCTTTATTCACATTCTTGCCCGCCTGATGAATGCTCATCCGGAATTTCGTATGGC
AATGAAAGACGGTGAGCTGGTGATATGGGATTCTGTTCACCCTTGTTACACCGTTTT
CCATGAGCAAACTGAAACGTTTTCCTCTCTCTGGTCCGAATACCACGACGATTTCCG
GCAGTTTCTACACATATATTCCCAAGATGTGGCGTGTTACGGTGAAAACCTGGCCT
ATTTCCCTAAAGGGTTTATTGAGAATATGTTTTTCGTCTCCGCCAATCCCTGGGTGT
CCTTCACCTCCTTTGATCTCAACGTGGCCAATATGGACAACTTCTTCGCCCCCGTTTT
CACCATGGGCAAATATTATACGCAAGGCGACAAGGTGCTGATGCCGCTGGCGATTC
AGGTTCATCATGCCGTTTGTGATGGCTTCCATGTCGGCCGCATGCTTAATGAACTGC
AACAGTACTGCGATGAGTGGCAGGGGGGGGGCGTAA
```

-continued

Sequence Listings:

ProC-maxRBS-hok (SEQ ID NO: 8)
CACAGCTAACACCACGTCGTCCCTATCTGCTGCCCTAGGTCTATGAGTGGTTGCTGG
ATAACTTTACGGGCATGCATAAGGCTCGTATGATATATTCAGGGAGACCACAACGG
TTTCCCTCTACAAATAATTTTGTTTAACTTTCGGGTATCCCGATTAAGGAGGTTTCGT
TATGAAATTACCCAGGTCAAGTCTAGTATAGTGCGTTCTGATCGTGTGCTTGACCTT
GCTGATCTTCACCTATCTGACGCGTAAGTCCCTGTGTGAAATTCGTTACCGCGACGG
CCACCGTGAGGTCGCTGCGTTTATGGCATACGAGAGCGGTAAATAACAGAAAAAA
GCCCGCACCTGACAGTGCGGGCTTTTTTTTTCGA pEVOL_MJWTyRS-CUA (SEQ ID NO: 9)
ATGCCATAGCATTTTTATCCATAAGATTAGCGGATCCTACCTGACGCTTTTTATCGC
AACTCTCTACTGTTTCTCCATACCCGTTTTTTTGGGCTAACAGGAGGAATTAGATCT
ATGGATGAATTCGAAATGATCAAGCGCAATACGTCGGAGATCATCTCTGAAGAAGA
ATTACGTGAGGTTTTAAAAAAAGACGAAAAATCGGCCTATATTGGCTTTGAACCAT
CAGGAAAAATCCACCTTGGTCACTACCTTCAGATTAAGAAAATGATTGACCTGCAA
AATGCAGGTTTCGACATTATTATCCTGCTGGCCGACCTGCATGCGTATCTTAATCAA
AAAGGCGAATTGGATGAGATCCGCAAGATCGGAGATTATAACAAGAAAGTATTCG
AGGCTATGGGTCTGAAAGCAAAGTATGTGTATGGGTCGGAGTTCCAGCTTGACAAG
GACTATACCCTTAACGTCTACCGTCTTGCTTTGAAAACCACCTTAAAGCGTGCGCGT
CGCAGCATGGAGCTGATCGCTCGTGAGGACGAGAACCCGAAAGTCGCTGAGGTAA
TCTATCCCATTATGCAAGTCAATGACATTCACTACCTTGGGGTGGATGTCGCAGTGG
GCGGGATGGAACAACGTAAGATTCACATGCTGGCACGCGAACTGCTTCCCAAGAA
GGTCGTGTGCATCCACAATCCGGTATTGACTGGCCTTGACGGGGAGGGAAAAATGT
CCAGCTCGAAGGGAAATTTATCGCAGTTGATGACTCCCCTGAGGAGATTCGTGCT
AAAATCAAGAAGGCGTATTGTCCAGCAGGCGTAGTTGAGGGCAATCCCATCATGGA
AATTGCGAAATATTTTCTTGAATACCCCCTTACGATTAAGCGTCCAGAGAAGTTTGG
TGGCGATCTGACGGTCAACTCTTACGAGGAGCTGGAATCCTTATTTAAGAATAAGG
AACTGCACCCAATGGACCTTAAAAACGCGGTTGCGGAAGAGTTGATTAAAATCTTA
GAGCCCATCCGTAAGCGTCTTTAACTGCAGTTTCAAACGCTAAATTGCCTGATCGC
TACGCTTATCAGGCCTACATGATCTCTGCAATATATTGAGTTTGCGTGCTTTTGTAG
GCCGGATAAGGCGTTCACGCCGCATCCGGCAAGAAACAGCAAACAATCCAAAACG
CCGCGTTCAGCGGCGTTTTTTTCTGCTTTTCTTCGCGAATTAATTCCGCTTCGCAACAT
GTGAGCACCGGTTTATTGACTACCGGAAGCAGTGTGACCGTGTGCTTCTCAAATGC
CTGAGGCCAGTTTGCTCAGGCTCTCCCCGTGGAGGTAATAATTGACGATATGATCA
GTGCACGGCTAACTAAGCGGCCTGCTGACTTTCTCGCCGATCAAAAGGCATTTTGCT
ATTAAGGGATTGACGAGGGCGTATCTGCGCAGTAAGATGCGCCCCGCATTCCGGCG
GTAGTTCAGCAGGGCAGAACGGCGGACTCTAAATCCGCATGGCAGGGGTTCAAATC
CCCTCCGCCGGACCAAATTCGAAAAGCCTGCTCAACGAGCAGGCTTTTTTGCATGC
TCGAGCAGCTCAGGGTCGAATTTGCTTTCGAATTTCTGCCATTCATCCGCTTATTAT
CACTTATTCAGGCGTAGCACCAGGCGTTTAAGGGCACCAATAACTGCCTTAAAAAA
ATTACGCCCCGCCCTGCCACTCATCGCAGTACTGTTGTAATTCATTAAGCATTCTGC
CGACATGGAAGCCATCACAGACGGCATGATGAACCTGAATCGCCAGCGGCATCAG
CACCTTGTCGCCTTGCGTATAATATTTGCCCATGGTGAAAACGGGGGCGAAGAAGT
TGTCCATATTGGCCACGTTTAAATCAAAACTGGTGAAACTCACCCAGGGATTGGCT
GAGACGAAAAACATATTCTCAATAAACCCTTTAGGGAAATAGGCCAGGTTTTCACC
GTAACACGCCACATCTTGCGAATATATGTGTAGAAACTGCCGGAAATCGTCGTGGT
ATTCACTCCAGAGCGATGAAAACGTTTCAGTTTGCTCATGGAAAACGGTGTAACAA
GGGTGAACACTATCCCATATCACCAGCTCACCGTCTTTCATTGCCATACGGAATTCC
GGATGAGCATTCATCAGGCGGGCAAGAATGTGAATAAAGGCCGGATAAAACTTGT
GCTTATTTTTCTTTACGGTCTTTAAAAAGGCCGTAATATCCAGCTGAACGGTCTGGT
TATAGGTACATTGAGCAACTGACTGAAATGCCTCAAAATGTTCTTTACGATGCCATT
GGGATATATCAACGGTGGTATATCCAGTGATTTTTTTCTCCATTTTAGCTTCCTTAGC
TCCTGAAAATCTCGATAACTCAAAAAATACGCCCGGTAGTGATCTTATTTCATTATG
GTGAAAGTTGGAACCTCTTACGTGCCGATCAACGTCTCATTTTCGCCAAAAGTTGGC
CCAGGGCTTCCCGGTATCAACAGGGACACCAGGATTTATTTATTCTGCGAAGTGAT
CTTCCGTCACAGGTATTTATTCGGCGCAAAGTGCGTCGGGTGATGCTGCCAACTTAC
TGATTTAGTGTATGATGGTGTTTTTGAGGTGCTCCAGTGGCTTCTGTTTCTATCAGCT
GTCCCTCCTGTTCAGCTACTGACGGGGTGGTGCGTAACGGCAAAAGCACCGCCGGA
CATCAGCGCTAGCGGAGTGTATACTGGCTTACTATGTTGGCACTGATGAGGGTGTC
AGTGAAGTGCTTCATGTGGCAGGAGAAAAAAGGCTGCACCGGTGCGTCAGCAGAA
TATGTGATACAGGATATATTCCGCTTCCTCGCTCACTGACTCGCTACGCTCGGTCGT
TCGACTGCGGCGAGCGGAAATGGCTTACGAACGGGGCGGAGATTTCCTGGAAGAT
GCCAGGAAGATACTTAACAGGGAAGTGAGAGGGCCGCGGCAAAGCCGTTTTTCCA
TAGGCTCCGCCCCCCTGACAAGCATCACGAAATCTGACGCTCAAATCAGTGGTGGC
GAAACCCGACAGGACTATAAAGATACCAGGCGTTTCCCCCTGGCGGCTCCCTCGTG
CGCTCTCCTGTTCCTGCCTTTCGGTTTACCGGTGTCATTCCGCTGTTATGGCCGCGTT
TGTCTCATTCCACGCCTGACACTCAGTTCCGGGTAGGCAGTTCGCTCCAAGCTGGAC
TGTATGCACGAACCCCCCGTTCAGTCCGACCGCTGCGCCTTATCCGGTAACTATCGT
CTTGAGTCCAACCCGGAAAGACATGCAAAAGCACCACTGGCAGCAGCCACTGGTA
ATTGATTTAGAGGAGTTAGTCTTGAAGTCATGCGCCGGTTAAGGCTAAACTGAAAG
GACAAGTTTTGGTGACTGCGCTCCTCCAAGCCAGTTACCTCGGTTCAAAGAGTTGGT
AGCTCAGAGAACCTTCGAAAAACCGCCCTGCAAGGCGGTTTTTTCGTTTTCAGAGC
AAGAGATTACGCGCAGACCAAAACGATCTCAAGAAGATCATCTTATTAATCAGATA
AAATATTTCTAGATTTCAGTGCAATTTATCTCTTCAAATGTAGCACCTGAAGTCAGC
CCCATACGATATAAGTTGTAATTCTCATGTTTGACAGCTTATCATCGATAAGCTTGG
TACCCAATTATGACAACTTGACGGCTACATCATTCACTTTTTCTTCACAACCGGCAC -continued Sequence Listings:

```
GGAACTCGCTCGGGCTGGCCCCGGTGCATTTTTTAAATACCCGCGAGAAATAGAGT
TGATCGTCAAAACCAACATTGCGACCGACGGTGGCGATAGGCATCCGGGTGGTGCT
CAAAAGCAGCTTCGCCTGGCTGATACGTTGGTCCTCGCGCCAGCTTAAGACGCTAA
TCCCTAACTGCTGGCGGAAAAGATGTGACAGACGCGACGGCGACAAGCAAACATG
CTGTGCGACGCTGGCGATATCAAAATTGCTGTCTGCCAGGTGATCGCTGATGTACT
GACAAGCCTCGCGTACCCGATTATCCATCGGTGGATGGAGCGACTCGTTAATCGCT
TCCATCGCCGCAGTAACAATTGCTCAAGCAGATTTATCGCCAGCAGCTCCGAATA
GCGCCCTTCCCCTTGCCCGGCGTTAATGATTTGCCCAAACAGGTCGCTGAAATGCG
GCTGGTGCGCTTCATCCGGGCGAAAGAACCCCGTATTGGCAAATATTGACGGCCAG
TTAAGCCATTCATGCCAGTAGGCGCGCGGACGAAAGTAAACCCACTGGTGATACCA
TTCGCGAGCCTCCGGATGACGACCGTAGTGATGAATCTCTCCTGGCGGGAACAGCA
AAATATCACTCGGTCGGCAAACAAATTCTCGTCCCTGATTTTTCACCACCCCCTGAC
CGCGAATGGTGAGATTGAGAATATAACCTTTCATTCCCAGCGGTCGGTCGATAAAA
AAATCGAGATAACCGTTGGCCTCAATCGGCGTTAAACCCGCCACCAGATGGGCATT
AAACGAGTATCCCGGCAGCAGGGGATCATTTTGCGCTTCAGCCATACTTTTCATACT
CCCGCCATTCAGAGAAGAAACCAATTGTCCATATTGCATCAGACATTGCCGTCACT
GCGTCTTTTACTGGCTCTTCTCGCTAACCAAACCGGTAACCCCGCTTATTAAAAGCA
TTCTGTAACAAAGCGGGACCAAAGCCATGACAAAAACGCGTAACAAAAGTGTCTA
TAATCACGGCAGAAAAGTCCACATTGATTATTTGCACGGCGTCACACTTTGCT
``` pUC57-Kan-Kid (SEQ ID NO: 10)
```
TGCAGCTCTGGCCCGTGTCTCAAAATCTCTGATGTTACATTGCACAAGATAAAAAT
ATATCATCATGAACAATAAAACTGTCTGCTTACATAAACAGTAATACAAGGGGTGT
TATGAGCCATATTCAACGGGAAACGTCGAGGCCGCGATTAAATTCCAACATGGATG
CTGATTTATATGGGTATAAATGGGCTCGCGATAATGTCGGGCAATCAGGTGCGACA
ATCTATCGCTTGTATGGGAAGCCCGATGCGCCAGAGTTGTTTCTGAAACATGGCAA
AGGTAGCGTTGCCAATGATGTTACAGATGAGATGGTCAGACTAAACTGGCTGACGG
AATTTATGCCTCTTCCGACCATCAAGCATTTTATCCGTACTCCTGATGATGCATGGT
TACTCACCACTGCGATCCCCGGAAAAACAGCATTCCAGGTATTAGAAGAATATCCT
GATTCAGGTGAAAATATTGTTGATGCGCTGGCAGTGTTCCTGCGCCGGTTGCATTCG
ATTCCTGTTTGTAATTGTCCTTTTAACAGCGATCGCGTATTTCGTCTCGCTCAGGCGC
AATCACGAATGAATAACGGTTTGGTTGATGCGAGTGATTTTGATGACGAGCGTAAT
GGCTGGCCTGTTGAACAAGTCTGGAAAGAAATGCATAAACTTTTGCCATTCTCACC
GGATTCAGTCGTCACTCATGGTGATTTCTCACTTGATAACCTTATTTTTGACGAGGG
GAAATTAATAGGTTGTATTGATGTTGGACGAGTCGGAATCGCAGACCGATACCAGG
ATCTTGCCATCCTATGGAACTGCCTCGGTGAGTTTTCTCCTTCATTACAGAAACGGC
TTTTTCAAAAATATGGTATTGATAATCCTGATATGAATAAAATTGCAGTTTCATTTGA
TGCTCGATGAGTTTTTCTAATCAGAATTGGTTAATTGGTTGTAACATTATTCAGATT
GGGCTTGATTTAAAACTTCATTTTTAATTTAAAAGGATCTAGGTGAAGATCCTTTTT
GATAATCTCATGACCAAAATCCCTTAACGTGAGTTTTCGTTCCACTGAGCGTCAGAC
CCCGTAGAAAAGATCAAAGGATCTTCTTGAGATCCTTTTTTTTCTGCGCGTAATCTGC
TGCTTGCAAACAAAAAAACCACCGCTACCAGCGGTGGTTTGTTTGCCGGATCAAGA
GCTACCAACTCTTTTTTCCGAAGGTAACTGGCTTCAGCAGAGCGCAGATACCAAATA
CTGTTCTTCTAGTGTAGCCGTAGTTAGGCCACCACTTCAAGAACTCTGTAGCACCGC
CTACATACCTCGCTCTGCTAATCCTGTTACCAGTGGCTGCTGCCAGTGGCGATAAGT
CGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCACGAG
GGAGCTTCCAGGGGGAAACGCCTGGTATCTTTATAGTCCTGTCGGGTTTCGCCACCT
CTGACTTGAGCGTCGATTTTTGTGATGCTCGTCAGGGGGGCGGAGCCTATGGAAAA
ACGCCAGCAACGCGGCCTTTTTACGGTTCCTGGCCTTTTGCTGGCCTTTTGCTCACA
TGTTCTTTCCTGCGTTATCCCCTGATTCTGTGGATAACCGTATTACCGCCTTTGAGTG
AGCTGATACCGCTCGCCGCAGCCGAACGACCGAGCGCAGCGAGTCAGTGAGCGAG
GAAGCGGAAGAGCGCCCAATACGCAAACCGCCTCTCCCCGCGCGTTGGCCGATTCA
TTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTT
CCGGCTCGTATGTTGTGTGGAATTGTGAGCGGATAACAATTTCACACAGGAAACAG
CTATGACCATGATTACGCCAAGCTTGCATGCAGGCCTCTGCAGTCGACGGGCCCGG
GATCCGATCACAGCTAACACCACGTCGTCCCTATCTGCTGCCCTAGGTCTATGAGTG
GTTGCTGGATAACTTTACGGGCATGCATAAGGCTCGTATGATATATTCAGGGAGAC
CACAACGGTTTCCCTCTACAAATAATTTTGTTTAACTTTATAAACACATCTAAGGAG
GTAAAGACCTGTATGTTAAAATAGCAACTAAAGAACGAAAATGGCTGGATGCATC
GTCGCTTGGTGCGTCGTAAAAGCGATATGGAACGTGGCGAAATTTAGCTGGTCTCC
CTGGACCCGACCGCGGGCCACGAGCAGCAGGGCACCCGCCCAGTTTTGATCGTGAC
CCCGGCTGCGTTCAACCGTGTTACCCGTCTGCCGGTCGTGGTGCCGGTGACGAGCG
GTGGTAATTTCGCCAGAACTGCGGGTTTTGCAGTTTCTCTGGACGGCGTTGGTATTC
GTACTACGGGTGTTGTACGCTGCGATCAACCGCGTACCATCGACATGAAAGCTCGT
GGTGGCAAGCGCCTTGAGCGCGTGCCGGAAACCATTATGAACGAGGTTCTGGGTCG
TTTAAGCACCATCCTGACCTAACAGAAAAAAGCCCGCACCTGACAGTGCGGGCTTT
TTTTTTCGAATCTAGATGTATTCGCGAGGTACCGAGCTCGAATTCTCTGGCCGTCGT
TTTACAACGTCGTGACTGGGAAAACCCTGGCGTTACCCAACTTAATCGCCTTGCAG
CACATCCCCCTTTCGCCAGCTGGCGTAATAGCGAAGAGGCCCGCACCGATCGCCCT
TCCCAACAGTTGCGCAGCCTGAATGGCGAATGGCGCCTGATGCGGTATTTTCTCCTT
ACGCATCTGTGCGGTATTTCACACCGCATATGGTGCACTCTCAGTACAATCTGCTCT
GATGCCGCATAGTTAAGCCAGCCCCGACACCCGCCAACACCCGCTGACGCGCCCTG
```

Sequence Listings:

```
ACGGGCTTGTCTGCTCCCGGCATCCGCTTACAGACAAGCTGTGACCGTCTCCGGGA
GCTGCATGTGTCAGAGGTTTTCACCGTCATCACCGAAACGCGCGA
``` pUC57-Kan-mazF (SEQ ID NO: 11)
```
TGCAGCTCTGGCCCGTGTCTCAAAATCTCTGATGTTACATTGCACAAGATAAAAT
ATATCATCATGAACAATAAAACTGTCTGCTTACATAAACAGTAATACAAGGGGTGT
TATGAGCCATATTCAACGGGAAACGTCGAGGCCGCGATTAAATTCCAACATGGATG
CTGATTTATATGGGTATAAATGGGCTCGCGATAATGTCGGGCAATCAGGTGCGACA
ATCTATCGCTTGTATGGGAAGCCCGATGCGCCAGAGTTGTTTCTGAAACATGGCAA
AGGTAGCGTTGCCAATGATGTTACAGATGAGATGGTCAGACTAAACTGGCTGACGG
AATTTATGCCTCTTCCGACCATCAAGCATTTTATCCGTACTCCTGATGATGCATGGT
TACTCACCACTGCGATCCCCGGAAAAACAGCATTCCAGGTATTAGAAGAATATCCT
GATTCAGGTGAAAATATTGTTGATGCGCTGGCAGTGTTCCTGCGCCGGTTGCATTCG
ATTCCTGTTTGTAATTGTCCTTTTAACAGCGATCGCGTATTTCGTCTCGCTCAGGCGC
AATCACGAATGAATAACGGTTTGGTTGATGCGAGTGATTTTGATGACGAGCGTAAT
GGCTGGCCTGTTGAACAAGTCTGGAAAGAAATGCATAAACTTTTGCCATTCTCACC
GGATTCAGTCGTCACTCATGGTGATTTCTCACTTGATAACCTTATTTTTGACGAGGG
GAAATTAATAGGTTGTATTGATGTTGGACGAGTCGGAATCGCAGACCGATACCAGG
ATCTTGCCATCCTATGGAACTGCCTCGGTGAGTTTTCTCCTTCATTACAGAAACGGC
TTTTTCAAAAATATGGTATTGATAATCCTGATATGAATAAATTGCAGTTTCATTTGA
TGCTCGATGAGTTTTTCTAATCAGAATTGGTTAATTGGTTGTAACATTATTCAGATT
GGGCTTGATTTAAAACTTCATTTTTAATTTAAAAGGATCTAGGTGAAGATCCTTTTT
GATAATCTCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGATCAAGA
GCTACCAACTCTTTTTCCGAAGGTAACTGGCTTCAGCAGAGCGCAGATACCAAATA
CTGTTCTTCTAGTGTAGCCGTAGTTAGGCCACCACTTCAAGAACTCTGTAGCACCGC
CTACATACCTCGCTCTGCTAATCCTGTTACCAGTGGCTGCTGCCAGTGGCGATAAGT
CGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCACGAG
GGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAA
ACGCCAGCAACGCGGCCTTTTTACGGTTCCTGGCCTTTTGCTGGCCTTTTGCTCACA
TGTTCTTTCCTGCGTTATCCCCTGATTCTGTGGATAACCGTATTACCGCCTTTGAGTG
AGCTGATACCGCTCGCCGCAGCCGAACGACCGAGCGCAGCGAGTCAGTGAGCGAG
GAAGCGGAAGAGCGCCCAATACGCAAACCGCCTCTCCCCGCGCGTTGGCCGATTCA
TTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTT
CCGGCTCGTATGTTGTGTGGAATTGTGAGCGGATAACAATTTCACACAGGAAACAG
CTATGACCATGATTACACCAAGCTTGCATGCAGGCCTCTGCAGTCGACGGGCCCGG
GATCCGATCACAGCTAACACCACGTCGTCCCTATCTGCTGCCCTAGGTCTATGAGTG
GTTGCTGGATAACTTTACGGGCATGCATAAGGCTCGTATGATATATTCAGGGAGAC
CACAACGGTTTCCCTCTACAAATAATTTTGTTTAACTTTACTACGACGTTACTTTAA
GGAGGATTTTTAATGGTTTCAAGGTATGTACCCGATATGGGAGACCTGATCTGGGT
TGACTTCGACCCGACCAAGGGCAGCGAGCAGGCGGGTCACCGTCCAGCAGTTGTGT
TGTCCCCGTTCATGTAGAATAACAAGACTGGTATGTGCCTGTGCGTTCCGTGTACCA
CGCAGAGCAAAGGCTAGCCGTTTGAAGTGGTGTTGTCTGGTCAAGAGCGCGATGGT
GTAGCCCTGGCGGATCAGGTTAAAAGCATTGCATGGCGTGCGCGTGGCGCTACCAA
GAAAGGAACCGTCGCTCCGGAAGAGCTGCAACTGATCAAAGCGAAGATCAACGTG
TTAATTGGCTAACAGAAAAAAGCCCGCACCTGACAGTGCGGGCTTTTTTTTTTCGAAT
CTAGATGTATTCGCGAGGTACCGAGCTCGAATTCTCTGGCCGTCGTTTTACAACGTC
GTGACTGGGAAAACCCTGGCGTTACCCAACTTAATCGCCTTGCAGCACATCCCCCTT
TCGCCAGCTGGCGTAATAGCGAAGAGGCCCGCACCGATCGCCCTTCCCAACAGTTG
CGCAGCCTGAATGGCGAATGGCGCCTGATGCGGTATTTTCTCCTTACGCATCTGTGC
GGTATTTCACACCGCATATGGTGCACTCTCAGTACAATCTGCTCTGATGCCGCATAG
TTAAGCCAGCCCCGACACCCGCCAACACCCGCTGACGCGCCCTGACGGGCTTGTCT
GCTCCCGGCATCCGCTTACAGACAAGCTGTGACCGTCTCCGGGAGCTGCATGTGTC
AGAGGTTTTCACCGTCATCACCGAAACGCGCGA
``` pUC57-Kan-timP (SEQ ID NO: 12)
```
TGCAGCTCTGGCCCGTGTCTCAAAATCTCTGATGTTACATTGCACAAGATAAAAT
ATATCATCATGAACAATAAAACTGTCTGCTTACATAAACAGTAATACAAGGGGTGT
TATGAGCCATATTCAACGGGAAACGTCGAGGCCGCGATTAAATTCCAACATGGATG
CTGATTTATATGGGTATAAATGGGCTCGCGATAATGTCGGGCAATCAGGTGCGACA
ATCTATCGCTTGTATGGGAAGCCCGATGCGCCAGAGTTGTTTCTGAAACATGGCAA
AGGTAGCGTTGCCAATGATGTTACAGATGAGATGGTCAGACTAAACTGGCTGACGG
AATTTATGCCTCTTCCGACCATCAAGCATTTTATCCGTACTCCTGATGATGCATGGT
TACTCACCACTGCGATCCCCGGAAAAACAGCATTCCAGGTATTAGAAGAATATCCT
GATTCAGGTGAAAATATTGTTGATGCGCTGGCAGTGTTCCTGCGCCGGTTGCATTCG
ATTCCTGTTTGTAATTGTCCTTTTAACAGCGATCGCGTATTTCGTCTCGCTCAGGCGC
AATCACGAATGAATAACGGTTTGGTTGATGCGAGTGATTTTGATGACGAGCGTAAT
GGCTGGCCTGTTGAACAAGTCTGGAAAGAAATGCATAAACTTTTGCCATTCTCACC
GGATTCAGTCGTCACTCATGGTGATTTCTCACTTGATAACCTTATTTTTGACGAGGG
GAAATTAATAGGTTGTATTGATGTTGGACGAGTCGGAATCGCAGACCGATACCAGG
ATCTTGCCATCCTATGGAACTGCCTCGGTGAGTTTTCTCCTTCATTACAGAAACGGC
```

-continued

---

<center>Sequence Listings:</center>

---

```
TTTTTCAAAAATATGGTATTGATAATCCTGATATGAATAAATTGCAGTTTCATTTGA
TGCTCGATGAGTTTTTCTAATCAGAATTGGTTAATTGGTTGTAACATTATTCAGATT
GGGCTTGATTTAAAACTTCATTTTTAATTTAAAAGGATCTAGGTGAAGATCCTTTTT
GATAATCTCATGACCAAAATCCCTTAACGTGAGTTTTCGTTCCACTGAGCGTCAGAC
CCCGTAGAAAAGATCAAAGGATCTTCTTGAGATCCTTTTTTTTCTGCGCGTAATCTGC
TGCTTGCAAACAAAAAAACCACCGCTACCAGCGGTGGTTTGTTTGCCGGATCAAGA
GCTACCAACTCTTTTTCCGAAGGTAACTGGCTTCAGCAGAGCGCAGATACCAAATA
CTGTTCTTCTAGTGTAGCCGTAGTTAGGCCACCACTTCAAGAACTCTGTAGCACCGC
CTACATACCTCGCTCTGCTAATCCTGTTACCAGTGGCTGCTGCCAGTGGCGATAAGT
CGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCACGAG
GGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAA
ACGCCAGCAACGCGGCCTTTTTACGGTTCCTGGCCTTTTGCTGGCCTTTTGCTCACA
TGTTCTTTCCTGCGTTATCCCCTGATTCTGTGGATAACCGTATTACCGCCTTTGAGTG
AGCTGATACCGCTCGCCGCAGCCGAACGACCGAGCGCAGCGAGTCAGTGAGCGAG
GAAGCGGAAGAGCGCCCAATACGCAAACCGCCTCTCCCCGCGCGTTGGCCGATTCA
TTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTT
CCGGCTCGTATGTTGTGTGGAATTGTGAGCGGATAACAATTTCACACAGGAAACAG
CTATGACCATGATTACACCAAGCTTGCATGCAGGCCTCTGCAGTCGACGGGCCCGG
GATCCGATCACAGCTAACACCACGTCGTCCCTATCTGCTGCCCTAGGTCTATGAGTG
GTTGCTGGATAACTTTACGGGCATGCATAAGGCTCGTATGATATATTCAGGGAGAC
CACAACGGTTTCCCTCTACAAATAATTTTGTTTAACTTTATAAAATAATCAAAATAA
GGAGGAGACGTCATGAAAATAAGGTGCTTTTGTATTGTACTAATCGTGAGCGGTGC
GCTGTAGACCGAGGTTAATAACAATCGTAGCTAGTCCGGCGACAACCTGTTGGTTG
TGAACAACCTGCAGTCTAGCAAGTAACAGAAAAAAGCCCGCCACCTGACAGTGCGG
GCTTTTTTTTTCGAATCTAGATGTATTCGCGAGGTACCGAGCTCGAATTCTCTGGCC
GTCGTTTTACAACGTCGTGACTGGGAAAACCCTGGCGTTACCCAACTTAATCGCCTT
GCAGCACATCCCCCTTTCGCCAGCTGGCGTAATAGCGAAGAGGCCCGCACCGATCG
CCCTTCCCAACAGTTGCGCAGCCTGAATGGCGAATGGCGCCTGATGCGGTATTTTCT
CCTTACGCATCTGTGCGGTATTTCACACCGCATATGGTGCACTCTCAGTACAATCTG
CTCTGATGCCGCATAGTTAAGCCAGCCCCGACACCCGCCAACACCCGCTGACGCGC
CCTGACGGGCTTGTCTGCTCCCGGCATCCGCTTACAGACAAGCTGTGACCGTCTCCG
GGAGCTGCATGTGTCAGAGGTTTTCACCGTCATCACCGAAACGCGCGA
```

Hok (SEQ ID NO: 14)
MKLPRSSLVWCVLIVCLTLLIFTYLTRKSLCEIRYRDGHREVAAFMAYESGK

Kid (SEQ ID NO: 15)
MLKYQLKNENGWMHRRLVRRKSDMERGEIWLVSLDPTAGHEQQGTRPVLIVTPAAFN
RVTRLPVVVPVTSGGNFARTAGFAVSLDGVGIRTTGVVRCDQPRTIDMKARGGKRLER
VPETIMNEVLGRLSTILT mazF (SEQ ID NO: 16)
MVSRYVPDMGDLIWVDFDPTKGSEQAGHRPAVVLSPFMYNNKTGMCLCVPCTTQSK
GYPFEVVLSGQERDGVALADQVKSIAWRARGATKKGTVAPEELQLIKAKINVLIG timP (SEQ ID NO: 17)
MKIRCFCIVLIVSGALLTEVNNNRSLSGDNLLVVNNLQSSK

---

<center>SEQUENCE LISTING</center>

<160> NUMBER OF SEQ ID NOS: 19

<210> SEQ ID NO 1
<211> LENGTH: 11
<212> TYPE: PRT
<213> ORGANISM: Artificial
<220> FEATURE:
<223> OTHER INFORMATION: C terminal degradation tag

<400> SEQUENCE: 1

Ala Ala Asn Asp Glu Asn Tyr Ala Leu Ala Ala
1               5                   10

<210> SEQ ID NO 2
<211> LENGTH: 18
<212> TYPE: DNA

-continued

```
<213> ORGANISM: Artificial
<220> FEATURE:
<223> OTHER INFORMATION: I SceI cleaved base pair sequence

<400> SEQUENCE: 2
tagggataac agggtaat                                                     18

<210> SEQ ID NO 3
<211> LENGTH: 4129
<212> TYPE: DNA
<213> ORGANISM: Artificial
<220> FEATURE:
<223> OTHER INFORMATION: pCTXVP60

<400> SEQUENCE: 3
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg cttctgtttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aacccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gtttttcagag caagagatta cgcgcagacc    1380
aaaacgatct caagaagatc atcttattag gatctattaa tacgactcac tatagggatc    1440
ccgggcgcgc cgtcgacttt aaagttcatc cttttcagaa acatatgaaa atccattagc    1500
agttcctcca agattaaaaa caagagtaga cttagatggt cttggtccaa ctggtctaac    1560
atcaataagt tcagtaagat caataagagt agtagaagct ccagttccag cataaaaata    1620
tccatcaaca gaaagtccaa tttccatgaa tccagaagca aaagtaagtt gccaaacaaa    1680
aaattgtcct ggcataagag cagaagaata attattaaga gaaagtccaa tagtaactgg    1740
aagtggttga gatccagttc catattgagt tccattagca gatccagcag tagcattaac    1800
atctccagtt cttctaacaa cagaagcaaa cataattgga gtattctttc caactggagc    1860
```

-continued

```
tgcagctgga gttcctggag tagtaacaat tctatctggt tgtggagtat aagtaatagc       1920
attagcagat ggagtagaaa taactccaga agccataaca aaaagtccag ctggattttg       1980
agcagttcca gtaacaacag catagataga cttagcaaca gtttgagatc cagaagtatt       2040
agtagttggt tgaagatttc ctggagctcc agtagcaaat ccaagttcat aagcttgaac       2100
agtagtaaca tttggagctc cagaattaga gttccaaata gctccaaatc caacccatcc       2160
agcagctgga atacctggtc cattgaatgg aacaaaagac atatctggaa atccatctgg       2220
agcaacttga gaaattggat tatcaatagc agatccagca ttagcatacc aaaattgaag       2280
aacattagta gcattagatc ctggataaga agcagatcct cttctatgat cgatatcagc       2340
aaatcttgga gaagaccatc cataagtaga tccattaaga ttccaatgtc tattacaagt       2400
agaaaatcct cctggaactg gttgaagtcc aacaatttgt ccattccatc tattatcatt       2460
tccaactcca gtaagaactg gagtagtaag aagtccagct ggatagatag aatcaacagt       2520
cttagaagat ggagttctaa tcataacaaa ttcaaaatct tcagatggtc tagttttcaac      2580 agtaacttga atagcagaag tagatcctcc aaatggatta ataagattat tataaacaga       2640
aagaacaaga gttggaacaa gtcctggatc tccagttgga tgatacatat ttggtctaag       2700
gtctggcata gtaatagtaa ctggttcaag agacctagca tcaataacaa catgtggaaa       2760
ttgtctaact tcaagacctg gtccaatttc aattcctggt ggataacag cagcaacaag        2820 tcttcctcca aaaactccag atccagcaac aatgaatctg aattgcattc ctccagccca       2880
tccagcatac atttgagaaa gaacagcagt gaatggatta ttttgtggag aatgttgaac       2940
agtataaaga atagatcctg gagcatcagc aacagaccaa gtaaaaacat cattataata       3000
aaaattagtt ctccaagttt cttgttgatc aacttgttgt ggtggtcctc caattccagc       3060
agtagcaata gaagcagaag aattttcagc agtaacaaca gaagtagtag caacaactcc       3120
tgggtccatt ccatcagtag tagttcctgg aacagaagca gtagtagcag ttccagcagc       3180
tccagcttgt ggagcagttc tagcctttcc ttccatgggt cctggtccat tagccataga       3240
aatagcagca atagcatgtg gagtcttatt attccaaaca cacaactttt caaccttagc       3300
ttcagtaaga taagcaattc taagagtatc cttcattctt tcaatagcct tcttttgaga       3360
atcaatatgt tgagatcctg gaacttcaac ttgaaaagta gctccattct taaaagtaat       3420
aatagccatt tctctctttc cagcaagaga ttcagtataa gaaaaaatct tatcattaag       3480
agtatgaatt tgagtattat gatattcagc acaaagatca gtaatatttt gtggagtgga       3540
ggaagccatt gtcccgggcg ccgcttcta tagtgtcacc taaatcgggt cgaatttgct       3600
ttcgaatttc tgccattcat ccgcttatta tcacttattc aggcgtacaa ccaggcgttt       3660
aagggcacca ataactgcct taaaaaaatt acgccccgcc ctgccactca tcgcagtact       3720
gttgtaattc attaagcatt ctgccgacat ggaagccatc acaaacggca tgatgaacct       3780
gaatcgccag cggcatcagc accttgtcgc cttgcgtata atatttgccc atagtgaaaa       3840 cggggggcgaa gaagttgtcc atattggcca cgtttaaatc aaaactggtg aaactcaccc      3900
agggattggc tgagacgaaa aacatattct caataaaccc tttagggaaa taggccaggt       3960
tttcaccgta acacgccaca tcttgcgaat atatgtgtag aaactgccgg aaatcgtcgt       4020
ggtattcact ccagagcgat gaaaacgttt cagtttgctc atggaaaacg gtgtaacaag       4080
ggtgaacact atcccatatc accagctcac cgtctttcat tgccatacg                    4129
```

<210> SEQ ID NO 4

-continued

```
<211> LENGTH: 5621
<212> TYPE: DNA
<213> ORGANISM: Artificial
<220> FEATURE:
<223> OTHER INFORMATION: ptRNAsup plasmid

<400> SEQUENCE: 4
tcattagtct tcaatgacgt gtaaaccacg gcgctttaag tcctctaacg aatccaacat      60
tccccttatt aattcaacag gatgcccctc ccagtcttca acaacgccaa caattctcaa     120
gggttcgcag gttctatagg actgtgttgg attaccggga aattttttgt tcgtaagatt     180
cggatcgtct tcgaacggtc ctgttggctc aactatgtat atgtagccgc gaccctcgag     240
gccagacagt gacatagcaa gttcagctcc ccaaactgct ggctccatca aggctgaaaa     300
gtagatgtgc ttaagaatac gaccgtcctc gaaatgagag atgaaccctg tggttagcaa     360
gtcaccaatc gccaaattgg ctttggttcc atgatagaac ggtccttgca cctgcttgta     420
attatcatga gagatgggaa tccaatcttt taccatataa cgaacctcct cttgcttatt     480
acagcaacgc cgcgtctgaa ttatttctag agaagcattt atcagggtta ttgtctcatg     540
agcggataca tatttgaatg tatttagaaa aataaacaaa tagggggttcc gcgcacattt     600 ccccgaaaag tgcgagtatt tacaacgaag acgcaatcac tttcttgatc agtgatcgtt     660
tcggcgtaat tttcagcaaa cgatcaaaag tggtgaaaaa tatcgttgac tcatcgcgcc     720
aggtaagtag aatgcaacgc atcgaacggc ggcactgatt gccagacgat aataaaatca     780
agtgattaac tgattgcttg atgaatcttt cttcccgagc ccggatggtg gaatcggtag     840
acacaaggga tttaaaatcc ctcggcgttc gcgctgtgcg ggttcaagtc ccgctccggg     900
taccatggga aagataagaa taaaatcaaa gcaataagca gtgtcctcgg taccaaattt     960
tcgaaaaaag acgctgaaaa gcgtcttttt tcgttttggt ccttacaatc agcagtcaga    1020
acttttacga agaatagtgg tcgctcaacc ttttctgttg ataaaacact cttttttgacg    1080 tttttacaga ctaattgaac gtgaagtgtg caaacgataa aagtgtagga aaaattgttt    1140
gacttataag tctcagaaag taatatgtgc gcgacgcagc gacgatgagc gataaacaag    1200
ttcttcgaag cactcgtaag aggcgtgtgg tgaggtggcc gagaggctga aggcgctccc    1260
ctgctaaggg agtatgcggt caaaagctgc atccggggtt cgaatccccg cctcaccgcc    1320
atttgcatct aaaaaaaaac cccgcccctg acagggcggg gttttttttt taattatagg    1380
gataacaggg taatatattc acttccctca cagattcgtt cagagataaa agcgttggta    1440
acagttgcct ggagtgtgac aaagcgttac acatcgctgt atgcaatgct gaaaatttca    1500
gcacttagcg aggtgcgagc aagctggcgc ttgcatggtg gcgtgcgaca ggtataatcc    1560
acaacgtttt cgcgcatacc tcttcagtgc cgaagtggcg aaatcggtag acgcagttga    1620
ttcaaaatca accgtagaaa tacgtgccgg ttcgagtccg gccttcggca ccaaaagtat    1680
gtaaatagac ctcaactgag gtcttttttt atgccaatta ttgaaggccg ctaacgcggc    1740
ctttttttgt ttctggtctc cctgcggata aagttgatac ccttacctga gttcttctga    1800
aaataacgga ctaaaaagca gaacgtgcgc gaaaacatta agaaaaatta taaaaacccg    1860
gcataaatgg cgaggggttta agcaatcgag cggcagcgta cttaccccgc actcgattag    1920
cgggtatact catgccgcat tgtcctctta gttaaatgga tataacgagc ccctcctaag    1980
ggctaattgc aggttcgatt cctgcagggg acaccattta tcagttcgct cccatccgta    2040
ccagtccgca aaatccaacg catgagaaag ccccggaag atcaccttcc ggggggcttt    2100
ttattgcgct gaaaagcaat ccctcgtgaa gtaactcaat agtgttctct ggtatcgtag    2160
```

-continued

```
tgtgcgtttg tttgccgcta tagcgaaata aatcagaaaa tcagacgcgg tcgttcactt   2220
gttcagcaac cagatcaaaa gccattgact cagcaagcgt tgaccgtata attcacgcga   2280
ttacacgcgc attgcggtat caacgcgccc ttagctcagt tggatagagc aacgaccttc   2340
taagtcgtgg gccgcaggtt cgaatcctgc agggcgcgcc attacaattc aatcagttac   2400
gccttcttta tatcctccat aagaaaaaag cccgcacctg acagtgcggg cttttttttt   2460
cgatcacttc tggaagcttg agcacgtgtt gacaattaat catcggcata gtatatcggc   2520
atagtataat acgacaaggt gaggaactaa acccctataa cccactaaga agaatttatg   2580
tcacatctcg cagaactggt tgcctcagcg aaggcggcca tttcacaggc gtcagatgtt   2640
gccgcgcttg ataatgtgcg cgtcgaatat ctaggtaaaa aagggcacct aacccttcag   2700
atgacgaccc tgcgtgagct gccgccagaa gagcgtccgg cagctggtgc ggttatcaac   2760
gaagcgaaag agcaggttca gcaggcgctg aatgcgcgta aagcggaact ggaatccgct   2820
gcactgaatg cgcgtctggc ggcggaaacg attgatgtct ctctgccagg tcgtcgcatt   2880
gaaaacggcg gtctgcatcc ggttacccgt accatcgacc gtatcgaatc attcttcggt   2940
gagcttggct ttaccgtggc aaccgggccg gaaatcgaag acgattatca taacttcgat   3000
gctctgaaca ttcctggtca ccacccggcg cgagctgacc acgacacttt ctggtttgac   3060
actacccgcc tgctgcgtac ccagacctct ggcgtacaga tccgcaccat gaaagcccag   3120
cagccaccga ttcgtatcat cgcgcctggc cgtgtttatc gtaacgacta cgaccagact   3180
cacacgccga tgttccatca gatggaaggt ctgattgttg ataccaacat ctcctttacc   3240
aacctgaaag gcacgctgca cgacttcctg cgtaacttct ttgaggaaga tctccagatt   3300
cgcttccgtc cttcctactt cccgtttgcc gaaccttctg cagaagtgga cgtcatgggt   3360
aaaaacggta aatggctgga agtgctgggc tgcgggatgg tgcatccgaa cgtgcttcgt   3420
aacgttggca tcgacccgga agtttactct ggtttcggct tcgggatggg gatggagcgt   3480
ctgactatgc tacgttacgg cgtcaccgac ctgcgttcat tcttcgaaaa cgatctgcgt   3540
ttcctcaaac agtttaaata acattaccct gttatcccta aataagattt acggattact   3600
atcttttcga aaaaaggcct cccaaatcgg ggggcctttt ttattgataa caaaatccat   3660
gggtatggac agttttccct ttgatatgta acggtgaaca gttgttctac ttttgtttgt   3720
tagtcttgat gcttcactga tagatacaag agccataaga acctcagatc cttccgtatt   3780
tagccagtat gttctctagt gtggttcgtt gtttttgcgt gagccatgag aacgaaccat   3840
tgagatcata cttactttgc atgtcactca aaaattttgc ctcaaaactg gtgagctgaa   3900
tttttgcagt taaagcatcg tgtagtgttt ttcttagtcc gttacgtagg taggaatctg   3960
atgtaatggt tgttggtatt ttgtcaccat tcatttttat ctggttgttc tcaagttcgg   4020
ttacgagatc catttgtcta tctagttcaa cttggaaaat caacgtatca gtcgggcggc   4080
ctcgcttatc aaccaccaat ttcatattgc tgtaagtgtt taaatcttta cttattggtt   4140
tcaaaaccca ttggttaagc cttttaaact catggtagtt attttcaagc attaacatga   4200
acttaaattc atcaaggcta atctctatat ttgccttgtg agttttcttt tgtgttagtt   4260 ctttaataa ccactcataa atcctcatag agtatttgtt ttcaaaagac ttaacatgtt   4320
ccagattata ttttatgaat tttttaact ggaaaagata aggcaatatc tcttcactaa   4380
aaactaattc taattttcg cttgagaact tggcatagtt tgtccactgg aaaatctcaa   4440
agcctttaac caaaggattc ctgatttcca cagttctcgt catcagctct ctggttgctt   4500
```

```
tagctaatac accataagca ttttccctac tgatgttcat catctgagcg tattggttat    4560
aagtgaacga taccgtccgt tctttccttg tagggttttc aatcgtgggg ttgagtagtg    4620
ccacacagca taaaattagc ttggtttcat gctccgttaa gtcatagcga ctaatcgcta    4680
gttcatttgc tttgaaaaca actaattcag acatacatct caattggtct aggtgatttt    4740
aatcactata ccaattgaga tgggctagtc aatgataatt actagtcctt ttcctttgag    4800
ttgtgggtat ctgtaaattc tgctagacct ttgctggaaa acttgtaaat tctgctagac    4860
cctctgtaaa ttccgctaga cctttgtgtg ttttttttgt ttatattcaa gtggttataa    4920
tttatagaat aaagaaagaa taaaaaaaga taaaaagaat agatcccagc cctgtgtata    4980
actcactact ttagtcagtt ccgcagtatt acaaaaggat gtcgcaaacg ctgtttgctc    5040
ctctacaaaa cagaccttaa aaccctaaag gcttaagtag caccctcgca agctcggttg    5100
cggccgcaat cgggcaaatc gctgaatatt ccttttgtct ccgaccatca ggcacctgag    5160
tcgctgtctt tttcgtgaca ttcagttcgc tgcgctcacg gctctggcag tgaatggggg    5220
taaatggcac tacaggcgcc ttttatggat tcatgcaagg aaactaccca taatacaaga    5280
aaagcccgtc acgggcttct cagggcgttt tatggcgggt ctgctatgtg gtgctatctg    5340 acttttttgct gttcagcagt tcctgccctc tgattttcca gtctgaccac ttcggattat    5400
cccgtgacag gtcattcaga ctggctaatg cacccagtaa ggcagcggta tcatcaacgg    5460
ggtctgacgc tcagtggaac gaaaactcac gttaagggat tttggtcatg agattatcaa    5520
aaaggatctt cacctagatc cttttaaatt aaaaatgaag ttttaaatca atctaaagta    5580
tatatgagta aacttggtct gactagggat aacagggtaa t                         5621
```

```
<210> SEQ ID NO 5
<211> LENGTH: 717
<212> TYPE: DNA
<213> ORGANISM: Artificial
<220> FEATURE:
<223> OTHER INFORMATION: chimeric construct CTXVP60 or f238

<400> SEQUENCE: 5
atgctattgc tgctatttct atggctaatg gaccaggacc catggaagga aaggctagaa      60
ctgctccaca agctggagct gctggaactg ctactactgc ttctgttcca ggaactacta     120
ctgatggaat ggaccaggga gttgttgcta ctacttctgt tgttactgct gaaaattctt     180
ctgcttctat tgctactgct ggaattggag gaccaccaca caagttgat caacaagaaa      240 cttggagaac taatttttat tataatgatg ttttttacttg gtctgttgct gatgctccag     300
gatctattct ttatactgtt caacattctc cacaaaataa tccattcact gctgttcttt     360
ctcaaatgta tgctggatgg gctggaggaa tgcaattcag attcattgtt gctggatctg     420 gagttttttgg aggaagactt gttgctgctg ttattccacc aggaattgaa attggaccag     480
gtcttgaagt tagacaattt ccacatgttg ttattgatgc taggtctctt gaaccagtta     540
ctattactat gccagacctt agaccaaata tgtatcatcc aactggagat ccaggacttg     600
ttccaactct tgttctttct gtttataata atcttattaa tccatttgga ggatctactt     660
ctgctattca agttactgtt gaaactagac catctgaaga ttttgaattt gttatga         717
```

```
<210> SEQ ID NO 6
<211> LENGTH: 1917
<212> TYPE: DNA
<213> ORGANISM: Artificial
<220> FEATURE:
<223> OTHER INFORMATION: human growth hormone plasmid
```

<400> SEQUENCE: 6

```
atggatctct ggcagctgct gttgaccttg gcactggcag gatcaagtga tgctttttct        60
ggaagtgagg ccacagcagc tatccttagc agagcaccct ggagtctgca aagtgttaat       120
ccaggcctaa agacaaattc ttctaaggag cctaaattca ccaagtgccg ttcacctgag       180
cgagagactt tttcatgcca ctggacagat gaggttcatc atggtacaaa gaacctagga       240
cccatacagc tgttctatac cagaaggaac actcaagaat ggactcaaga atggaaagaa       300
tgccctgatt atgtttctgc tggggaaaac agctgttact ttaattcatc gtttacctcc       360
atctggatac cttattgtat caagctaact agcaatggtg gtacagtgga tgaaaagtgt       420
ttctctgttg atgaaatagt gcaaccagat ccacccattg ccctcaactg gactttactg       480
aacgtcagtt taactgggat tcatgcagat atccaagtga gatgggaagc accacgcaat       540
gcagatattc agaaaggatg gatggttctg gagtatgaac ttcaatacaa agaagtaaat       600
gaaactaaat ggaaaatgat ggaccctata ttgacaacat cagttccagt gtactcattg       660
aaagtggata aggaatatga agtgcgtgtg agatccaaac aacgaaactc tggaaattat       720
ggcgagttca gtgaggtgct ctatgtaaca cttcctcaga tgagccaatt tacatgtgaa       780
gaagatttct actttccatg gctcttaatt attatctttg gaatatttgg gctaacagtg       840
atgctatttg tattcttatt ttctaaacag caaaggatta aaatgctgat tctgccccca       900
gttccagttc aaagattaa aggaatcgat ccagatctcc tcaaggaagg aaaattagag       960
gaggtgaaca caatcttagc cattcatgat agctataaac ccgaattcca cagtgatgac      1020
tcttgggttg aatttattga ctagatatt gatgagccag atgaaaagac tgaggaatca      1080
gacacagaca gacttctaag cagtgaccat gagaaatcac atagtaacct aggggtgaag      1140
gatggcgact ctggacgtac cagctgttgt gaacctgaca ttctggagac tgatttcaat      1200
gccaatgaca tacatgaggg tacctcagag gttgctcagc cacagaggtt aaaagggggaa      1260 gcagatctct tatgccttga ccagaagaat caaaataact caccttatca tgatgcttgc      1320
cctgctactc agcagcccag tgttatccaa gcagagaaaa caaaccaca accacttcct      1380 actgaaggag ctgagtcaac tcaccaagct gcccatattc agctaagcaa tccaagttca      1440
ctgtcaaaca tcgactttta tgcccaggtg agcgacatta caccagcagg tagtgtggtc      1500
ctttccccgg gccaaaagaa taaggcaggg atgtcccaat gtgacatgca cccggaaatg      1560
gtctcactct gccaagaaaa cttccttatg gacaatgcct acttctgtga ggcagatgcc      1620
aaaaagtgca tccctgtggc tcctcacatc aaggttgaat cacacataca gccaagctta      1680
aaccaagagg acatttacat caccacagaa agccttacca ctgctgctgg gaggcctggg      1740
acaggagaac atgttccagg ttctgagatg cctgtcccag actatacctc cattcatata      1800
gtacagtccc cacagggcct catactcaat gcgactgcct tgcccttgcc tgacaaagag      1860
tttctctcat catgtggcta tgtgagcaca gaccaactga acaaaatcat gccttag        1917
```

<210> SEQ ID NO 7
<211> LENGTH: 4814
<212> TYPE: DNA
<213> ORGANISM: Artificial
<220> FEATURE:
<223> OTHER INFORMATION: pUC-hGHR wt-RC55 plasmid

<400> SEQUENCE: 7

```
ttatattatt tttgccaaat aatttttaac aaaagctctg aagtcttctt catttaaatt        60
```

```
cttagatgat acttcatctg gaaaattgtc ccaattagta gcatcacgct gtgagtaagt      120
tctaaaccat tttttattg ttgtattatc tctaatctta ctactcgatg agttttcggt      180
attatctcta tttttaactt ggagcaggtt ccattcattg ttttttttcat catagtgaat     240 aaaatcaact gctttaacac ttgtgcctga acaccatatc catccggcgt aatacgactc      300
actataggga gagcggccgc cagatcttcc ggatggctcg agttttttcag caagatatgg      360 atctctggca gctgctgttg accttggcac tggcaggatc aagtgatgct ttttctggaa      420
gtgaggccac agcagctatc cttagcagag caccctggag tctgcaaagt gttaatccag      480
gcctaaagac aaattcttct aaggagccta aattcaccaa gtgccgttca cctgagcgag      540
agactttttc atgccactgg acagatgagg ttcatcatgg tacaaagaac ctaggaccca      600
tacagctgtt ctataccaga aggaacactc aagaatggac tcaagaatgg aaagaatgcc      660
ctgattatgt ttctgctggg gaaaacagct gttactttaa ttcatcgttt acctccatct      720 ggataccta ttgtatcaag ctaactagca atggtggtac agtggatgaa aagtgtttct       780
ctgttgatga aatagtgcaa ccagatccac ccattgccct caactggact ttactgaacg      840
tcagtttaac tgggattcat gcagatatcc aagtgagatg ggaagcacca cgcaatgcag      900
atattcagaa aggatggatg gttctggagt atgaacttca atacaaagaa gtaaatgaaa      960
ctaaatggaa aatgatggac cctatattga caacatcagt tccagtgtac tcattgaaag    1020
tggataagga atatgaagtg cgtgtgagat ccaaacaacg aaactctgga aattatggcg     1080
agttcagtga ggtgctctat gtaacacttc ctcagatgag ccaatttaca tgtgaagaag     1140
atttctactt tccatggctc ttaattatta tctttggaat atttgggcta acagtgatgc     1200
tatttgtatt cttattttct aaacagcaaa ggattaaaat gctgattctg cccccagttc     1260
cagttccaaa gattaaagga atcgatccag atctcctcaa ggaaggaaaa ttagaggagg     1320
tgaacacaat cttagccatt catgatagct ataaacccga attccacagt gatgactctt     1380
gggttgaatt tattgagcta gatattgatg agccagatga aaagactgag gaatcagaca     1440
cagacagact tctaagcagt gaccatgaga atcacatag taacctaggg gtgaaggatg      1500
gcgactctgg acgtaccagc tgttgtgaac ctgacattct ggagactgat ttcaatgcca     1560
atgacataca tgagggtacc tcagaggttg ctcagccaca gaggttaaaa ggggaagcag     1620
atctcttatg ccttgaccag aagaatcaaa ataactcacc ttatcatgat gcttgccctg     1680
ctactcagca gcccagtgtt atccaagcag agaaaaacaa accacaacca cttcctactg     1740
aaggagctga gtcaactcac caagctgccc atattcagct aagcaatcca agttcactgt     1800
caaacatcga ctttttatgcc caggtgagcg acattacacc agcaggtagt gtggtccttt     1860
ccccgggcca aaagaataag gcaggggatgt cccaatgtga catgcacccg gaaatggtct    1920
cactctgcca agaaaacttc cttatggaca atgcctactt ctgtgaggca gatgccaaaa     1980
agtgcatccc tgtggctcct cacatcaagg ttgaatcaca catacagcca agcttaaacc     2040
aagaggacat ttacatcacc acagaaagcc ttaccactgc tgctgggagg cctgggacag     2100
gagaacatgt tccaggttct gagatgcctg tcccagacta tacctccatt catatagtac     2160
agtccccaca gggcctcata ctcaatgcga ctgccttgcc cttgcctgac aaaagagtttc     2220 tctcatcatg tggctatgtg agcacagacc aactgaacaa aatcatgcct tagatctttc     2280
tagaagatct cctacaatat tctcagctgc catggaaaat cgatgttctt cttttattct     2340
ctcaagattt tcaggctgta tattaaaact tatattaaga actatgctaa ccacctcatc     2400
aggaaccgtt gtaggtggcg tgggttttct tggcaatcga ctctcatgaa aactacgagc     2460
```

```
taaatattca atatgttcct cttgaccaac tttattctgc attttttttg aacgaggttt    2520
agagcaagct tcaggaaact gagacaggaa ttttattaaa aatttaaatt ttgaagaaag    2580
ttcagggtta atagcatcca tttttttgctt tgcaagttcc tcagcattct taacaaaaga    2640
cgtctctttt gacatgttta aagtttaaac ctcctgtgtg aaattgttat ccgctcacaa    2700
ttccacacat tatacgagcc ggaagcataa agtgtaaagc ctggggtgcc taatgagtga    2760
gctaactcac attaattgcg ttgcgctcac tgccaattgc tttccagtcg ggaaacctgt    2820
cgtgccagct gcattaatga atcggccaac gcgcggggag aggcggtttg cgtattgggc    2880
gctcttccgc ttcctcgctc actgactcgc tgcgctcggt cgttcggctg cggcgagcgg    2940
tatcagctca ctcaaaggcg gtaatacggt tatccacaga atcaggggat aacgcaggaa    3000
agaacatgtg agcaaaaggc cagcaaaagg ccaggaaccg taaaaaggcc gcgttgctgg    3060 cgttttttcca taggctccgc cccccctgacg agcatcacaa aaatcgacgc tcaagtcaga    3120
ggtggcgaaa cccgacagga ctataaagat accaggcgtt tcccccctgga agctccctcg    3180 tgcgctctcc tgttccgacc ctgccgctta ccggatacct gtccgccttt ctcccttcgg    3240
gaagcgtggc gctttctcat agctcacgct gtaggtatct cagttcggtg taggtcgttc    3300
gctccaagct gggctgtgtg cacgaacccc ccgttcagcc cgaccgctgc gccttatccg    3360
gtaactatcg tcttgagtcc aacccggtaa gacacgactt atcgccactg gcagcagcca    3420
ctggtaacag gattagcaga gcgaggtatg taggcggtgc tacagagttc ttgaagtggt    3480
ggcctaacta cggctacact agaaggacag tatttggtat ctgcgctctg ctgaagccag    3540
ttaccttcgg aaaaagagtt ggtagctctt gatccggcaa acaaaccacc gctggtagcg    3600
gtggtttttt tgtttgcaag cagcagatta cgcgcagaaa aaaaggatct caagaagatc    3660
ctttgatctt ttctacgggg tctgacgctc agtggaacga aaactcacgt taagggattt    3720
tggtcatgag attatcaaaa aggatcttca cctagatcct tttaaattaa aaatgaagtt    3780
ttaaatcaat ctaaagtata tatgagtaaa cttggtctga cagttaccaa tgcttaatca    3840
gagaggcacc tatctcagcg atctggcgat ttcgttcatc catagttgcc tgggaccccg    3900
tcgtgtagat aactacgata cgggagggct taccatctgg ccccagtgct gcaatgatac    3960
cgcgagaccc acgctcaccg gctccagatt tatcagcaat aaaccagcca gccggaaggg    4020
cggagcgcag aagtggtcct gcaactttat ccgcctccat ccagtctatc agttgttgcc    4080
gggaagctag agtaagtagt tcgccagtta gtagtttgcg cagcgttgtt gccattgcta    4140
caggcatcgt ggtgtcacgc tcgtcgtttg gtatggcttc attcagctcc ggttcccaac    4200
gatcaaggcg agttacatga tcccccatgt tgtgcagaaa agcggttagc tccttcggtc    4260
ctccgatcgt tgtcagaagc aggttggccg cagtgttatc agacatggtt atggcagcag    4320
agcacagttc gcgtactgtc atgccatccg taagatgctt ttctgtgact ggggagtact    4380
caacgaggtc attctgagaa tagtgtatgc ggcgaccgag ttgctcttgc ccggcgtcaa    4440
tacgggacag taccgcgcca catagcagaa ctttaaaagt ggacatcatt ggaaaacgtt    4500
cttcggggcg aaaggactca aggatcttac cagagttgag atccagttcg atgtaaccca    4560
ctcgtgcacc tagctgatct tcagcatctt ttactttcac cagcgtttct gggtgagcaa    4620
aaacaggaag gcaaaatgcc gcaaaaaagg gaataagggc gacacggaaa tgttgaatgg    4680
acatcgtagg gtaacctgaa tattattgaa gcatttatca gggttattgt ctcatgagcg    4740
gatacatatt tgaatgtatt tagaaaaata aacaaatagg ggttccgcgc acatttcccc    4800
```

```
gaaaagtgcc acct                                                                    4814

<210> SEQ ID NO 8
<211> LENGTH: 374
<212> TYPE: DNA
<213> ORGANISM: Artificial
<220> FEATURE:
<223> OTHER INFORMATION: Hok expression construct

<400> SEQUENCE: 8
cacagctaac accacgtcgt ccctatctgc tgccctaggt ctatgagtgg ttgctggata      60
actttacggg catgcataag gctcgtatga tatattcagg gagaccacaa cggtttccct     120
ctacaaataa ttttgtttaa ctttcgggta tcccgattaa ggaggtttcg ttatgaaatt     180
acccaggtca agtctagtat agtgcgttct gatcgtgtgc ttgaccttgc tgatcttcac     240
ctatctgacg cgtaagtccc tgtgtgaaat tcgttaccgc gacggccacc gtgaggtcgc     300
tgcgtttatg gcatacgaga gcggtaaata acagaaaaaa gcccgcacct gacagtgcgg     360
gctttttttt tcga                                                       374

<210> SEQ ID NO 9
<211> LENGTH: 4780
<212> TYPE: DNA
<213> ORGANISM: Artificial
<220> FEATURE:
<223> OTHER INFORMATION: Hok expression construct

<400> SEQUENCE: 9
atgccatagc atttttatcc ataagattag cggatcctac ctgacgcttt ttatcgcaac      60
tctctactgt ttctccatac ccgttttttt gggctaacag gaggaattag atctatggat     120
gaattcgaaa tgatcaagcg caatacgtcg gagatcatct ctgaagaaga attacgtgag     180
gttttaaaaa aagacgaaaa atcggcctat attggctttg aaccatcagg aaaaatccac     240
cttggtcact accttcagat taagaaaatg attgacctgc aaaatgcagg tttcgacatt     300
attatcctgc tggccgacct gcatgcgtat cttaatcaaa aaggcgaatt ggatgagatc     360
cgcaagatcg gagattataa caagaaagta ttcgaggcta tgggtctgaa agcaaagtat     420
gtgtatgggt cggagttcca gcttgacaag gactataccc ttaacgtcta ccgtcttgct     480
ttgaaaacca ccttaaagcg tgcgcgtcgc agcatggagc tgatcgctcg tgaggacgag     540
aacccgaaag tcgctgaggt aatctatccc attatgcaag tcaatgacat tcactacctt     600
ggggtggatg tcgcagtggg cgggatggaa caacgtaaga ttcacatgct ggcacgcgaa     660
ctgcttccca agaaggtcgt gtgcatccac aatccggtat tgactggcct tgacggggag     720
ggaaaaatgt ccagctcgaa gggaaatttt atcgcagttg atgactcccc tgaggagatt     780
cgtgctaaaa tcaagaaggc gtattgtcca gcaggcgtag ttgagggcaa tcccatcatg     840
gaaattgcga atatttttct tgaataccc cttacgatta agcgtccaga gaagtttggt     900
ggcgatctga cggtcaactc ttacgaggag ctggaatcct tatttaagaa taaggaactg     960
cacccaatgg accttaaaaa cgcggttgcg gaagagttga ttaaaatctt agagcccatc    1020
cgtaagcgtc tttaactgca gtttcaaacg ctaaattgcc tgatgcgcta cgcttatcag    1080
gcctacatga tctctgcaat atattgagtt tgcgtgcttt tgtaggccgg ataaggcgtt    1140
cacgccgcat ccggcaagaa acagcaaaca atccaaaacg ccgcgttcag cggcgttttt    1200
tctgcttttc ttcgcgaatt aattccgctt cgcaacatgt gagcaccggt ttattgacta    1260
ccggaagcag tgtgaccgtg tgcttctcaa atgcctgagg ccagtttgct caggctctcc    1320
```

-continued

```
ccgtggaggt aataattgac gatatgatca gtgcacggct aactaagcgg cctgctgact    1380
ttctcgccga tcaaaaggca ttttgctatt aagggattga cgagggcgta tctgcgcagt    1440
aagatgcgcc ccgcattccg gcggtagttc agcagggcag aacggcggac tctaaatccg    1500
catggcaggg gttcaaatcc cctccgccgg accaaattcg aaaagcctgc tcaacgagca    1560
ggcttttttg catgctcgag cagctcaggg tcgaatttgc tttcgaattt ctgccattca    1620
tccgcttatt atcacttatt caggcgtagc accaggcgtt taagggcacc aataactgcc    1680
ttaaaaaaat tacgccccgc cctgccactc atcgcagtac tgttgtaatt cattaagcat    1740
tctgccgaca tggaagccat cacagacggc atgatgaacc tgaatcgcca gcggcatcag    1800
caccttgtcg ccttgcgtat aatatttgcc catggtgaaa acgggggcga gaagttgtc    1860 catattggcc acgtttaaat caaaactggt gaaactcacc cagggattgg ctgagacgaa    1920
aaacatattc tcaataaacc ctttagggaa ataggccagg ttttcaccgt aacacgccac    1980
atcttgcgaa tatatgtgta gaaactgccg gaaatcgtcg tggtattcac tccagagcga    2040
tgaaaacgtt tcagtttgct catggaaaac ggtgtaacaa gggtgaacac tatcccatat    2100
caccagctca ccgtctttca ttgccatacg gaattccgga tgagcattca tcaggcgggc    2160
aagaatgtga ataaaggccg gataaaactt gtgcttattt ttctttacgg tctttaaaaa    2220
ggccgtaata tccagctgaa cggtctggtt ataggtacat tgagcaactg actgaaatgc    2280
ctcaaaatgt tctttacgat gccattggga tatatcaacg gtggtatatc cagtgatttt    2340
tttctccatt ttagcttcct tagctcctga aaatctcgat aactcaaaaa atacgcccgg    2400
tagtgatctt atttcattat ggtgaaagtt ggaacctctt acgtgccgat caacgtctca    2460
ttttcgccaa aagttggccc agggcttccc ggtatcaaca gggacaccag gatttattta    2520
ttctgcgaag tgatcttccg tcacaggtat ttattcggcg caaagtgcgt cgggtgatgc    2580
tgccaactta ctgatttagt gtatgatggt gtttttgagg tgctccagtg cttctgtt     2640 ctatcagctg tccctcctgt tcagctactg acggggtggt gcgtaacggc aaaagcaccg    2700
ccggacatca gcgctagcgg agtgtatact ggcttactat gttggcactg atgagggtgt    2760
cagtgaagtg cttcatgtgg caggagaaaa aaggctgcac cggtgcgtca gcagaatatg    2820
tgatacagga tatattccgc ttcctcgctc actgactcgc tacgctcggt cgttcgactg    2880
cggcgagcgg aaatggctta cgaacggggc ggagatttcc tggaagatgc caggaagata    2940
cttaacaggg aagtgagagg gccgcggcaa agccgttttt ccataggctc cgcccccctg    3000
acaagcatca cgaaatctga cgctcaaatc agtggtggcg aaacccgaca ggactataaa    3060
gataccaggc gtttccccct ggcggctccc tcgtgcgctc tcctgttcct gcctttcggt    3120
ttaccggtgt cattccgctg ttatggccgc gtttgtctca ttccacgcct gacactcagt    3180
tccgggtagg cagttcgctc caagctggac tgtatgcacg aacccccgt tcagtccgac    3240 cgctgcgcct tatccggtaa ctatcgtctt gagtccaacc cggaaagaca tgcaaaagca    3300
ccactggcag cagccactgg taattgattt agaggagtta gtcttgaagt catgcgccgg    3360
ttaaggctaa actgaaagga caagttttgg tgactgcgct cctccaagcc agttacctcg    3420
gttcaaagag ttggtagctc agagaacctt cgaaaaaccg ccctgcaagg cggttttttc    3480
gttttcagag caagagatta cgcgcagacc aaaacgatct caagaagatc atcttattaa    3540
tcagataaaa tatttctaga tttcagtgca atttatctct tcaaatgtag cacctgaagt    3600
cagccccata cgatataagt tgtaattctc atgtttgaca gcttatcatc gataagcttg    3660
```

-continued

```
gtacccaatt atgacaactt gacggctaca tcattcactt tttcttcaca accggcacgg        3720
aactcgctcg ggctggcccc ggtgcatttt ttaaatacccc gcgagaaata gagttgatcg       3780
tcaaaaccaa cattgcgacc gacggtggcg ataggcatcc gggtggtgct caaaagcagc       3840
ttcgcctggc tgatacgttg gtcctcgcgc cagcttaaga cgctaatccc taactgctgg       3900
cggaaaagat gtgacagacg cgacggcgac aagcaaacat gctgtgcgac gctggcgata       3960
tcaaaattgc tgtctgccag gtgatcgctg atgtactgac aagcctcgcg tacccgatta       4020
tccatcggtg gatggagcga ctcgttaatc gcttccatgc gccgcagtaa caattgctca       4080
agcagattta tcgccagcag ctccgaatag cgcccttccc cttgcccggc gttaatgatt       4140
tgcccaaaca ggtcgctgaa atgcggctgg tgcgcttcat ccgggcgaaa gaaccccgta       4200
ttggcaaata ttgacggcca gttaagccat tcatgccagt aggcgcgcgg acgaaagtaa       4260
acccactggt gataccattc gcgagcctcc ggatgacgac cgtagtgatg aatctctcct       4320
ggcgggaaca gcaaaatatc actcggtcgg caaacaaatt ctcgtccctg atttttcacc       4380
accccctgac cgcgaatggt gagattgaga atataacctt tcattcccag cggtcggtcg       4440
ataaaaaaat cgagataacc gttggcctca atcggcgtta aacccgccac cagatgggca       4500
ttaaacgagt atcccggcag caggggatca ttttgcgctt cagccatact tttcatactc       4560
ccgccattca gagaagaaac caattgtcca tattgcatca gacattgccg tcactgcgtc       4620
ttttactggc tcttctcgct aaccaaaccg gtaaccccgc ttattaaaag cattctgtaa       4680
caaagcggga ccaaagccat gacaaaaacg cgtaacaaaa gtgtctataa tcacggcaga       4740
aaagtccaca ttgattattt gcacggcgtc acactttgct                            4780
```

```
<210> SEQ ID NO 10
<211> LENGTH: 3198
<212> TYPE: DNA
<213> ORGANISM: Artificial
<220> FEATURE:
<223> OTHER INFORMATION: pUC57-Kan-Kid plasmid

<400> SEQUENCE: 10
tgcagctctg ccccgtgtct caaaatctct gatgttacat tgcacaagat aaaaatatat         60
catcatgaac aataaaactg tctgcttaca taaacagtaa tacaaggggt gttatgagcc       120
atattcaacg ggaaacgtcg aggccgcgat taaattccaa catggatgct gatttatatg       180
ggtataaatg ggctcgcgat aatgtcgggc aatcaggtgc gacaatctat cgcttgtatg       240
ggaagcccga tgcgccagag ttgtttctga aacatggcaa aggtagcgtt gccaatgatg       300
ttacagatga gatggtcaga ctaaactggc tgacggaatt tatgcctctt ccgaccatca       360
agcattttat ccgtactcct gatgatgcat ggttactcac cactgcgatc cccggaaaaa       420
cagcattcca ggtattagaa gaatatcctg attcaggtga aaatattgtt gatgcgctgg       480
cagtgttcct gcgccggttg cattcgattc ctgtttgtaa ttgtcctttt aacagcgatc       540
gcgtatttcg tctcgctcag gcgcaatcac gaatgaataa cggtttggtt gatgcgagtg       600
attttgatga cgagcgtaat ggctggcctg ttgaacaagt ctggaaagaa atgcataaac       660
ttttgccatt ctcaccggat tcagtcgtca ctcatggtga tttctcactt gataaccttaa      720 tttttgacga ggggaaatta ataggttgta ttgatgttgg acgagtcgga atcgcagacc       780
gataccagga tcttgccatc ctatggaact gcctcggtga gttttctcct tcattacaga       840
aacggctttt tcaaaaatat ggtattgata atcctgatat gaataaattg cagtttcatt       900
tgatgctcga tgagtttttc taatcagaat tggttaattg gttgtaacat tattcagatt       960
```

```
gggcttgatt taaaacttca tttttaattt aaaaggatct aggtgaagat ccttttttgat      1020 aatctcatga ccaaaatccc ttaacgtgag ttttcgttcc actgagcgtc agaccccgta      1080
gaaaagatca aaggatcttc ttgagatcct ttttttctgc gcgtaatctg ctgcttgcaa      1140
acaaaaaaac caccgctacc agcggtggtt tgtttgccgg atcaagagct accaactctt      1200
tttccgaagg taactggctt cagcagagcg cagataccaa atactgttct tctagtgtag      1260
ccgtagttag gccaccactt caagaactct gtagcaccgc ctacatacct cgctctgcta      1320
atcctgttac cagtggctgc tgccagtggc gataagtcgt gtcttaccgg gttggactca      1380
agacgatagt taccggataa ggcgcagcgg tcgggctgaa cggggggttc gtgcacacag      1440
cccagcttgg agcgaacgac ctacaccgaa ctgagatacc tacagcgtga gctatgagaa      1500
agcgccacgc ttcccgaagg gagaaaggcg gacaggtatc cggtaagcgg cagggtcgga      1560
acaggagagc gcacgaggga gcttccaggg ggaaacgcct ggtatcttta tagtcctgtc      1620
gggtttcgcc acctctgact tgagcgtcga ttttgtgat gctcgtcagg ggggcggagc       1680
ctatggaaaa acgccagcaa cgcggccttt ttacggttcc tggccttttg ctggcctttt      1740
gctcacatgt tctttcctgc gttatcccct gattctgtgg ataaccgtat taccgccttt      1800
gagtgagctg ataccgctcg ccgcagccga acgaccgagc gcagcgagtc agtgagcgag      1860
gaagcggaag agcgcccaat acgcaaaccg cctctccccg cgcgttggcc gattcattaa      1920
tgcagctggc acgacaggtt tcccgactgg aaagcgggca gtgagcgcaa cgcaattaat      1980
gtgagttagc tcactcatta ggcaccccag gctttacact ttatgcttcc ggctcgtatg      2040
ttgtgtggaa ttgtgagcgg ataacaattt cacacaggaa acagctatga ccatgattac      2100
accaagcttg catgcaggcc tctgcagtcg acgggcccgg gatccgatca cagctaacac      2160
cacgtcgtcc ctatctgctg ccctaggtct atgagtggtt gctggataac tttacgggca      2220
tgcataaggc tcgtatgata tattcaggga gaccacaacg gtttccctct acaaataatt      2280
ttgtttaact ttataaacac atctaaggag gtaaagacct gtatgttaaa atagcaacta      2340
aagaacgaaa atggctggat gcatcgtcgc ttggtgcgtc gtaaaagcga tatggaacgt      2400
ggcgaaattt agctggtctc cctggacccg accgcgggcc acgagcagca gggcacccgc      2460
ccagttttga tcgtgacccc ggctgcgttc aaccgtgtta cccgtctgcc ggtcgtggtg      2520
ccggtgacga gcggtggtaa tttcgccaga actgcgggtt ttgcagtttc tctggacggc      2580
gttggtattc gtactacggg tgttgtacgc tgcgatcaac cgcgtaccat cgacatgaaa      2640
gctcgtggtg gcaagcgcct tgagcgcgtg ccggaaacca ttatgaacga ggttctgggt      2700
cgtttaagca ccatcctgac ctaacagaaa aaagcccgca cctgacagtg cgggcttttt      2760
ttttcgaatc tagatgtatt cgcgaggtac cgagctcgaa ttctctggcc gtcgttttac      2820
aacgtcgtga ctgggaaaac cctggcgtta cccaacttaa tcgccttgca gcacatcccc      2880
ctttcgccag ctggcgtaat agcgaagagg cccgcaccga tcgcccttcc caacagttgc      2940
gcagcctgaa tggcgaatgg cgcctgatgc ggtattttct ccttacgcat ctgtgcggta      3000
tttcacaccg catatggtgc actctcagta caatctgctc tgatgccgca tagttaagcc      3060
agccccgaca cccgccaaca cccgctgacg cgccctgacg ggcttgtctg ctcccggcat      3120
ccgcttacag acaagctgtg accgtctccg ggagctgcat gtgtcagagg ttttcaccgt      3180
catcaccgaa acgcgcga                                                    3198
```

<210> SEQ ID NO 11

<211> LENGTH: 3132
<212> TYPE: DNA
<213> ORGANISM: Artificial
<220> FEATURE:
<223> OTHER INFORMATION: pUC57-Kan-mazF plasmid

<400> SEQUENCE: 11

```
tgcagctctg gcccgtgtct caaaatctct gatgttacat tgcacaagat aaaaatatat      60
catcatgaac aataaaactg tctgcttaca taaacagtaa tacaaggggt gttatgagcc     120
atattcaacg ggaaacgtcg aggccgcgat taaattccaa catggatgct gatttatatg     180
ggtataaatg ggctcgcgat aatgtcgggc aatcaggtgc gacaatctat cgcttgtatg     240
ggaagcccga tgcgccagag ttgtttctga acatggcaa aggtagcgtt gccaatgatg     300
ttacagatga gatggtcaga ctaaactggc tgacggaatt tatgcctctt ccgaccatca     360
agcattttat ccgtactcct gatgatgcat ggttactcac cactgcgatc cccggaaaaa     420
cagcattcca ggtattagaa gaatatcctg attcaggtga aaatattgtt gatgcgctgg     480
cagtgttcct gcgccggttg cattcgattc ctgtttgtaa ttgtcctttt aacagcgatc     540
gcgtatttcg tctcgctcag gcgcaatcac gaatgaataa cggtttggtt gatgcgagtg     600
attttgatga cgagcgtaat ggctggcctg ttgaacaagt ctggaaagaa atgcataaac     660
ttttgccatt ctcaccggat tcagtcgtca ctcatggtga tttctcactt gataacctta     720
tttttgacga ggggaaatta ataggttgta ttgatgttgg acgagtcgga atcgcagacc     780
gataccagga tcttgccatc ctatggaact gcctcggtga gttttctcct tcattacaga     840
aacggctttt tcaaaaatat ggtattgata atcctgatat gaataaattg cagtttcatt     900
tgatgctcga tgagtttttc taatcagaat ggttaattg gttgtaacat tattcagatt     960
gggcttgatt taaaacttca tttttaattt aaaaggatct aggtgaagat ccttttttgat    1020 aatctcatga ccaaaatccc ttaacgtgag ttttcgttcc actgagcgtc agaccccgta    1080
gaaaagatca aaggatcttc ttgagatcct tttttttctgc cgcgtaatctg ctgcttgcaa    1140 acaaaaaaac caccgctacc agcggtggtt tgtttgccgg atcaagagct accaactctt    1200
tttccgaagg taactggctt cagcagagcg cagataccaa atactgttct ctagtgtag     1260 ccgtagttag gccaccactt caagaactct gtagcaccgc ctacatacct cgctctgcta    1320
atcctgttac cagtggctgc tgccagtggc gataagtcgt gtcttaccgg gttggactca    1380
agacgatagt taccggataa ggcgcagcgg tcgggctgaa cggggggttc gtgcacacag    1440
cccagcttgg agcgaacgac ctacaccgaa ctgagatacc tacagcgtga gctatgagaa    1500
agcgccacgc ttcccgaagg gagaaaggcg acaggtatc cggtaagcgg cagggtcgga    1560
acaggagagc gcacgaggga gcttccaggg ggaaacgcct ggtatcttta tagtcctgtc    1620
gggtttcgcc acctctgact tgagcgtcga ttttgtgat gctcgtcagg ggggcggagc    1680
ctatggaaaa acgccagcaa cgcggccttt ttacggttcc tggccttttg ctggcctttt    1740
gctcacatgt tctttcctgc gttatcccct gattctgtgg ataaccgtat taccgccttt    1800
gagtgagctg ataccgctcg ccgcagccga acgaccgagc gcagcgagtc agtgagcgag    1860
gaagcggaag agcgcccaat acgcaaaccg cctctccccg cgcgttggcc gattcattaa    1920
tgcagctggc acgacaggtt tcccgactgg aaagcgggca gtgagcgcaa cgcaattaat    1980
gtgagttagc tcactcatta ggcacccag gctttacact ttatgcttcc ggctcgtatg    2040
ttgtgtggaa ttgtgagcgg ataacaattt cacacaggaa acagctatga ccatgattac    2100
accaagcttg catgcaggcc tctgcagtcg acgggcccgg gatccgatca cagctaacac    2160
```

-continued

```
cacgtcgtcc ctatctgctg ccctaggtct atgagtggtt gctggataac tttacgggca    2220
tgcataaggc tcgtatgata tattcaggga gaccacaacg gtttccctct acaaataatt    2280
ttgtttaact ttactacgac gttactttaa ggaggatttt taatggtttc aaggtatgta    2340
cccgatatgg gagacctgat ctgggttgac ttcgacccga ccaagggcag cgagcaggcg    2400
ggtcaccgtc cagcagttgt gttgtccccg ttcatgtaga ataacaagac tggtatgtgc    2460
ctgtgcgttc cgtgtaccac gcagagcaaa ggctagccgt ttgaagtggt gttgtctggt    2520
caagagcgcg atggtgtagc cctggcggat caggttaaaa gcattgcatg gcgtgcgcgt    2580
ggcgctacca agaaaggaac cgtcgctccg aagagctgc aactgatcaa agcgaagatc    2640
aacgtgttaa ttggctaaca gaaaaaagcc cgcacctgac agtgcgggct ttttttttcg    2700
aatctagatg tattcgcgag gtaccgagct cgaattctct ggccgtcgtt ttacaacgtc    2760
gtgactggga aaaccctggc gttacccaac ttaatcgcct tgcagcacat ccccctttcg    2820
ccagctggcg taatagcgaa gaggcccgca ccgatcgccc ttcccaacag ttgcgcagcc    2880
tgaatggcga atggcgcctg atgcggtatt ttctccttac gcatctgtgc ggtatttcac    2940
accgcatatg gtgcactctc agtacaatct gctctgatgc cgcatagtta agccagcccc    3000
gacacccgcc aacacccgct gacgcgccct gacgggcttg tctgctcccg gcatccgctt    3060
acagacaagc tgtgaccgtc tccgggagct gcatgtgtca gaggttttca ccgtcatcac    3120
cgaaacgcgc ga                                                        3132
```

```
<210> SEQ ID NO 12
<211> LENGTH: 2922
<212> TYPE: DNA
<213> ORGANISM: Artificial
<220> FEATURE:
<223> OTHER INFORMATION: pUC57-Kan-timP plasmid

<400> SEQUENCE: 12
tgcagctctg gcccgtgtct caaaatctct gatgttacat tgcacaagat aaaaatatat      60
catcatgaac aataaaactg tctgcttaca taaacagtaa tacaaggggt gttatgagcc     120
atattcaacg ggaaacgtcg aggccgcgat taaattccaa catggatgct gatttatatg     180
ggtataaatg ggctcgcgat aatgtcgggc aatcaggtgc gacaatctat cgcttgtatg     240
ggaagcccga tgcgccagag ttgtttctga aacatggcaa aggtagcgtt gccaatgatg     300
ttacagatga gatggtcaga ctaaactggc tgacggaatt tatgcctctt ccgaccatca     360
agcattttat ccgtactcct gatgatgcat ggttactcac cactgcgatc cccggaaaaa     420
cagcattcca ggtattagaa gaatatcctg attcaggtga aaatattgtt gatgcgctgg     480
cagtgttcct cgccggttg cattcgattc ctgtttgtaa ttgtcctttt aacagcgatc     540
gcgtatttcg tctcgctcag gcgcaatcac gaatgaataa cggtttggtt gatgcgagtg     600
attttgatga cgagcgtaat ggctggcctg ttgaacaagt ctggaaagaa atgcataaac     660
ttttgccatt ctcaccggat tcagtcgtca ctcatggtga tttctcactt gataacctta     720
tttttgacga ggggaaatta ataggttgta ttgatgttgg acgagtcgga atcgcagacc     780
gataccagga tcttgccatc ctatggaact gcctcggtga gttttctcct tcattacaga     840
aacggctttt tcaaaaatat ggtattgata atcctgatat gaataaattg cagtttcatt     900
tgatgctcga tgagtttttc taatcagaat tggttaattg gttgtaacat tattcagatt     960
gggcttgatt taaaacttca ttttttaattt aaaaggatct aggtgaagat cctttttgat    1020
```

```
aatctcatga ccaaaatccc ttaacgtgag ttttcgttcc actgagcgtc agaccccgta    1080
gaaaagatca aaggatcttc ttgagatcct ttttttctgc gcgtaatctg ctgcttgcaa    1140
acaaaaaaac caccgctacc agcggtggtt tgtttgccgg atcaagagct accaactctt    1200
tttccgaagg taactggctt cagcagagcg cagataccaa atactgttct tctagtgtag    1260
ccgtagttag gccaccactt caagaactct gtagcaccgc ctacatacct cgctctgcta    1320
atcctgttac cagtggctgc tgccagtggc gataagtcgt gtcttaccgg gttggactca    1380
agacgatagt taccggataa ggcgcagcgg tcgggctgaa cggggggttc gtgcacacag    1440
cccagcttgg agcgaacgac ctacaccgaa ctgagatacc tacagcgtga gctatgagaa    1500
agcgccacgc ttcccgaagg gagaaaggcg gacaggtatc cggtaagcgg cagggtcgga    1560
acaggagagc gcacgaggga gcttccaggg ggaaacgcct ggtatcttta tagtcctgtc    1620
gggtttcgcc acctctgact tgagcgtcga tttttgtgat gctcgtcagg gggcggagc    1680 ctatggaaaa acgccagcaa cgcggccttt ttacggttcc tggccttttg ctggcctttt    1740
gctcacatgt tctttcctgc gttatcccct gattctgtgg ataaccgtat taccgccttt    1800
gagtgagctg ataccgctcg ccgcagccga cgaccgagc gcagcgagtc agtgagcgag    1860
gaagcggaag agcgcccaat acgcaaaccg cctctccccg cgcgttggcc gattcattaa    1920
tgcagctggc acgacaggtt tcccgactgg aaagcgggca gtgagcgcaa cgcaattaat    1980
gtgagttagc tcactcatta ggcacccag gctttacact ttatgcttcc ggctcgtatg    2040
ttgtgtggaa ttgtgagcgg ataacaattt cacacaggaa acagctatga ccatgattac    2100
accaagcttg catgcaggcc tctgcagtcg acgggcccgg gatccgatca cagctaacac    2160
cacgtcgtcc ctatctgctg ccctaggtct atgagtggtt gctggataac tttacgggca    2220
tgcataaggc tcgtatgata tattcaggga accacaacg gtttccctct acaaataatt    2280
ttgtttaact ttataaaata atcaaaataa ggaggagacg tcatgaaaat aaggtgcttt    2340
tgtattgtac taatcgtgag cggtcgctg tagaccgagg ttaataacaa tcgtagctag    2400
tccggcgaca acctgttggt tgtgaacaac ctgcagtcta gcaagtaaca gaaaaaagcc    2460
cgcacctgac agtgcgggct ttttttttcg aatctagatg tattcgcgag gtaccgagct    2520
cgaattctct ggccgtcgtt ttacaacgtc gtgactggga aaaccctggc gttacccaac    2580
ttaatcgcct tgcagcacat cccccttcg ccagctggcg taatagcgaa gaggcccgca    2640
ccgatcgccc ttcccaacag ttgcgcagcc tgaatggcga atggcgcctg atgcggtatt    2700
ttctccttac gcatctgtgc ggtatttcac accgcatatg gtgcactctc agtacaatct    2760
gctctgatgc cgcatagtta agccagcccc gacacccgcc aacacccgct gacgcgccct    2820
gacgggcttg tctgctcccg gcatccgctt acagacaagc tgtgaccgtc tccgggagct    2880
gcatgtgtca gaggttttca ccgtcatcac cgaaacgcgc ga                       2922
```

```
<210> SEQ ID NO 13
<211> LENGTH: 5042
<212> TYPE: DNA
<213> ORGANISM: Artificial
<220> FEATURE:
<223> OTHER INFORMATION: p15A-hGHR wt-RC55 plasmid

<400> SEQUENCE: 13
ccaattattg aaggccgcta acgcggcctt tttttgtttc tggtctccct ctatcagctg      60
tccctcctgt tcagctactg acggggtggt gcgtaacggc aaaagcaccg ccggacatca    120
gcgctagcgg agtgtatact ggcttactat gttggcactg atgagggtgt cagtgaagtg    180
```

```
cttcatgtgg caggagaaaa aaggctgcac cggtgcgtca gcagaatatg tgatacagga      240
tatattccgc ttcctcgctc actgactcgc tacgctcggt cgttcgactg cggcgagcgg      300
aaatggctta cgaacggggc ggagatttcc tggaagatgc caggaagata cttaacaggg      360
aagtgagagg gccgcggcaa agccgttttt ccataggctc cgccccctg acaagcatca       420 cgaaatctga cgctcaaatc agtggtggcg aaacccgaca ggactataaa gataccaggc      480
gtttccccct ggcggctccc tcgtgcgctc tcctgttcct gcctttcggt ttaccggtgt      540
cattccgctg ttatggccgc gtttgtctca ttccacgcct gacactcagt tccgggtagg      600
cagttcgctc caagctggac tgtatgcacg aaccccccgt tcagtccgac cgctgcgcct      660
tatccggtaa ctatcgtctt gagtccaacc cggaaagaca tgcaaaagca ccactggcag      720
cagccactgg taattgattt agaggagtta gtcttgaagt catgcgccgg ttaaggctaa      780
actgaaagga caagttttgg tgactgcgct cctccaagcc agttacctcg gttcaaagag      840
ttggtagctc agagaacctt cgaaaaaccg ccctgcaagg cggttttttc gttttcagag      900
caagagatta cgcgcagacc aaaacgatct caagaagatc atcttattaa tcagataaaa      960
tatttctaga tttcagtgca atttatctct tcaaatgtag cacctgaagt cagccccata      1020
cgatataagt tgtaccaccg tcaaaaaaaa cggcgctttt tagcgccgtt tttatttttc      1080
aaccttttag gacagcttga cggctacatc attcactttt tcttcacaac cggcacggaa      1140
ctcggacgga gaggcccggg tgcatttttt aaatacccga gagaaataga gttgatcgtc      1200
aaaaccaaca ttgcgaccga cggtggcgat aggcatccgg gtggtggaca gaagcagctt      1260
cgcctgagag atacgttggt cctcgcgcca ggacaggaca gaaatcccga gctgctggcg      1320
gaaaagatga gacagacgag acggagagag gcaaacatgc tgtgcgacag aggcgatatc      1380
aaaattagag tctgccaggt gatcagagat gtactgacaa gcctcgcgta cccgattatc      1440
catcggtgga tggagggact cgttaatcgc ttccatgcgc cgcagaagta gttgctcaag      1500
cagatttatc gccagcagct cagaatagcg cccttcccct tgcccggcgt taatgatttg      1560
cccaaacagg tcggagaaat gcggctggtg cgcttcatcc gggcgaaaga accccgtatt      1620
ggcaaatata gacggccagt taagccattc atgccagtag gcgcgcggac gaaagtaaac      1680
ccactggtga taccattcgc gagcctccgg atgacgaccg tagtgatgaa tctctcctgg      1740
cgggaacaga agaatatcac ccggtcggca aacaaattct cgtccctgat ttttcaccac      1800
cccctgaccg cgaatggtga gattgagaat ataacctttc attcccagcg gtcggtcgat      1860
aaaaaaatcg agataaccgt tggcctcaat cggcgtaaga cccgccacca gatgggcatt      1920
aaaagagtat cccggcagca ggggatcatt ttgcgcttca gccatacttt tcatactccc      1980
gccattcaga agaaaacca attgtccata ttgcatcaga cattgccgtc actgcgtctt      2040
ttactggctc ttctcgctaa ccaaaccggt aaccccgctt attaaaagca ttctgtaaca      2100
aagcgggacc aaagccatga caaaaacgcg taacaaaagt gtctataatc acggcagaaa      2160
agtccacatt gattatttgc acggcgtcac actttgctat gccatagcat ttttatccat      2220
aagattagcg gatcctacct gacgctttt atcgcaactc tctactgttt ctccataccc      2280
atggatctct ggcagctgct gttgacctg gcactggcag gatcaagtga tgctttttct      2340
ggaagtgagg ccacagcagc tatccttagc agagcaccct ggagtctgca aagtgttaat      2400
ccaggcctaa agacaaattc ttctaaggag cctaaattca ccaagtgccg ttcacctgag      2460
cgagagactt tttcatgcca ctggacagat gaggttcatc atggtacaaa gaacctagga      2520
```

-continued

```
cccatacagc tgttctatac cagaaggaac actcaagaat ggactcaaga atggaaagaa    2580
tgccctgatt atgtttctgc tggggaaaac agctgttact ttaattcatc gtttacctcc    2640
atctggatac cttattgtat caagctaact agcaatggtg gtacagtgga tgaaaagtgt    2700
ttctctgttg atgaaatagt gcaaccagat ccacccattg ccctcaactg gactttactg    2760
aacgtcagtt taactgggat tcatgcagat atccaagtga gatgggaagc accacgcaat    2820
gcagatattc agaaaggatg gatggttctg gagtatgaac ttcaatacaa agaagtaaat    2880
gaaactaaat ggaaaatgat ggaccctata ttgacaacat cagttccagt gtactcattg    2940
aaagtggata aggaatatga agtgcgtgtg agatccaaac aacgaaactc tggaaattat    3000
ggcgagttca gtgaggtgct ctatgtaaca cttcctcaga tgagccaatt tacatgtgaa    3060
gaagatttct actttccatg gctcttaatt attatctttg gaatatttgg gctaacagtg    3120
atgctatttg tattcttatt ttctaaacag caaaggatta aaatgctgat tctgcccca    3180 gttccagttc caaagattaa aggaatcgat ccagatctcc tcaaggaagg aaaattagag    3240
gaggtgaaca caatcttagc cattcatgat agctataaac ccgaattcca cagtgatgac    3300
tcttgggttg aatttattga ctagatatt gatgagccag atgaaaagac tgaggaatca    3360
gacacagaca gacttctaag cagtgaccat gagaaatcac atagtaacct aggggtgaag    3420
gatggcgact ctggacgtac cagctgttgt gaacctgaca ttctggagac tgatttcaat    3480
gccaatgaca tacatgaggg tacctcagag gttgctcagc cacagaggtt aaaaggggaa    3540
gcagatctct tatgccttga ccagaagaat caaaataact caccttatca tgatgcttgc    3600
cctgctactc agcagcccag tgttatccaa gcagagaaaa caaaccaca accacttcct    3660 actgaaggag ctgagtcaac tcaccaagct gcccatattc agctaagcaa tccaagttca    3720
ctgtcaaaca tcgactttta tgcccaggtg agcgacatta caccagcagg tagtgtggtc    3780 ctttcccgg gccaaaagaa taaggcaggg atgtcccaat gtgacatgca cccggaaatg    3840
gtctcactct gccaagaaaa cttccttatg gacaatgcct acttctgtga ggcagatgcc    3900
aaaaagtgca tccctgtggc tcctcacatc aaggttgaat cacacataca gccaagctta    3960
aaccaagagg acatttacat caccacagaa agccttacca ctgctgctgg gaggcctggg    4020
acaggagaac atgttccagg ttctgagatg cctgtcccag actataccte cattcatata    4080 gtacagtccc cacagggcct catactcaat gcgactgcct tgcccttgcc tgacaaagag    4140
tttctctcat catgtggcta tgtgagcaca gaccaactga acaaaatcat gccttagagt    4200
caaaagcctc cgaccggagg cttttgactc ctgttgatac cgggaagccc tgggccaact    4260
tttggcgaaa atgagacgtt gatcggcacg taagaggttc caactttcac cataatgaaa    4320
taagatcact accgggcgta ttttttgagt tatcgagatt ttcaggagct aaggaagcta    4380
aaatggagaa aaaaatcact ggatatacca ccgttgatat atcccaatgg catcgtaaag    4440
aacattttga ggcatttcag tccgttgctc aatgtaccta taaccagacc gttcagctgg    4500
atattacggc ctttctgaag accgtaaaga aaaataagca caagttttat ccggccttta    4560
ttcacattct tgcccgcctg atgaatgctc atccggaatt tcgtatggca atgaaagacg    4620
gtgagctggt gatatgggat tctgttcacc cttgttacac cgttttccat gagcaaactg    4680
aaacgttttc ctctctctgg tccgaatacc acgacgattt ccggcagttt ctacacatat    4740
attcccaaga tgtggcgtgt tacggtgaaa acctggccta tttccctaaa gggtttattg    4800
agaatatgtt ttcgtctcc gccaatccct gggtgtcctt cacctccttt gatctcaacg    4860
tggccaatat ggacaacttc ttcgcccccg ttttcaccat gggcaaatat tatacgcaag    4920
```

-continued

```
gcgacaaggt gctgatgccg ctggcgattc aggttcatca tgccgtttgt gatggcttcc    4980
atgtcggccg catgcttaat gaactgcaac agtactgcga tgagtggcag ggcggggcgt    5040
aa                                                                    5042
```

<210> SEQ ID NO 14
<211> LENGTH: 52
<212> TYPE: PRT
<213> ORGANISM: Artificial
<220> FEATURE:
<223> OTHER INFORMATION: Hok protein

<400> SEQUENCE: 14

```
Met Lys Leu Pro Arg Ser Ser Leu Val Trp Cys Val Leu Ile Val Cys
1               5                   10                  15

Leu Thr Leu Leu Ile Phe Thr Tyr Leu Thr Arg Lys Ser Leu Cys Glu
            20                  25                  30

Ile Arg Tyr Arg Asp Gly His Arg Glu Val Ala Ala Phe Met Ala Tyr
        35                  40                  45

Glu Ser Gly Lys
    50
```

<210> SEQ ID NO 15
<211> LENGTH: 133
<212> TYPE: PRT
<213> ORGANISM: Artificial
<220> FEATURE:
<223> OTHER INFORMATION: Kid protein

<400> SEQUENCE: 15

```
Met Leu Lys Tyr Gln Leu Lys Asn Glu Asn Gly Trp Met His Arg Arg
1               5                   10                  15

Leu Val Arg Arg Lys Ser Asp Met Glu Arg Gly Glu Ile Trp Leu Val
            20                  25                  30

Ser Leu Asp Pro Thr Ala Gly His Glu Gln Gln Gly Thr Arg Pro Val
            35                  40                  45

Leu Ile Val Thr Pro Ala Ala Phe Asn Arg Val Thr Arg Leu Pro Val
    50                  55                  60

Val Val Pro Val Thr Ser Gly Gly Asn Phe Ala Arg Thr Ala Gly Phe
65                  70                  75                  80

Ala Val Ser Leu Asp Gly Val Gly Ile Arg Thr Thr Gly Val Val Arg
                85                  90                  95

Cys Asp Gln Pro Arg Thr Ile Asp Met Lys Ala Arg Gly Gly Lys Arg
            100                 105                 110

Leu Glu Arg Val Pro Glu Thr Ile Met Asn Glu Val Leu Gly Arg Leu
        115                 120                 125

Ser Thr Ile Leu Thr
    130
```

<210> SEQ ID NO 16
<211> LENGTH: 111
<212> TYPE: PRT
<213> ORGANISM: Artificial
<220> FEATURE:
<223> OTHER INFORMATION: mazF protein

<400> SEQUENCE: 16

```
Met Val Ser Arg Tyr Val Pro Asp Met Gly Asp Leu Ile Trp Val Asp
1               5                   10                  15
```

```
Phe Asp Pro Thr Lys Gly Ser Glu Gln Ala Gly His Arg Pro Ala Val
            20              25              30

Val Leu Ser Pro Phe Met Tyr Asn Asn Lys Thr Gly Met Cys Leu Cys
        35              40              45

Val Pro Cys Thr Thr Gln Ser Lys Gly Tyr Pro Phe Glu Val Val Leu
    50              55              60

Ser Gly Gln Glu Arg Asp Gly Val Ala Leu Ala Asp Gln Val Lys Ser
65              70              75              80

Ile Ala Trp Arg Ala Arg Gly Ala Thr Lys Lys Gly Thr Val Ala Pro
                85              90              95

Glu Glu Leu Gln Leu Ile Lys Ala Lys Ile Asn Val Leu Ile Gly
            100             105             110

<210> SEQ ID NO 17
<211> LENGTH: 41
<212> TYPE: PRT
<213> ORGANISM: Artificial
<220> FEATURE:
<223> OTHER INFORMATION: timP protein

<400> SEQUENCE: 17

Met Lys Ile Arg Cys Phe Cys Ile Val Leu Ile Val Ser Gly Ala Leu
1               5               10              15

Leu Thr Glu Val Asn Asn Asn Arg Ser Leu Ser Gly Asp Asn Leu Leu
            20              25              30

Val Val Asn Asn Leu Gln Ser Ser Lys
        35              40

<210> SEQ ID NO 18
<211> LENGTH: 717
<212> TYPE: DNA
<213> ORGANISM: Artificial
<220> FEATURE:
<223> OTHER INFORMATION: CTX-VP60 chimeric construct

<400> SEQUENCE: 18
atgctattgc tgctatttct atggctaatg gaccaggacc catggaagga aaggctagaa      60
ctgctccaca agctggagct gctggaactg ctactactgc ttctgttcca ggaactacta     120
ctgatggaat ggacccagga gttgttgcta ctacttctgt tgttactgct gaaaattctt     180
ctgcttctat tgctactgct ggaattggag gaccaccaca acaagttgat caacaagaaa     240
cttggagaac taattttat tataatgatg tttttacttg gtctgttgct gatgctccag     300
gatctattct ttatactgtt caacattctc cacaaaataa tccattcact gctgttcttt     360
ctcaaatgta tgctggatgg gctggaggaa tgcaattcag attcattgtt gctggatctg     420 gagttttttgg aggaagactt gttgctgctg ttattccacc aggaattgaa attggaccag     480
gtcttgaagt tagacaattt ccacatgttg ttattgatgc taggtctctt gaaccagtta     540
ctattactat gccagacctt agaccaaata tgtatcatcc aactggagat ccaggacttg     600
ttccaactct tgttctttct gtttataata atcttattaa tccatttgga ggatctactt     660
ctgctattca agttactgtt gaaactagac atctgaaga ttttgaattt gttatga        717

<210> SEQ ID NO 19
<211> LENGTH: 272
<212> TYPE: PRT
<213> ORGANISM: Artificial
<220> FEATURE:
<223> OTHER INFORMATION: CTX-VP60 chimeric construct
```

-continued

```
<400> SEQUENCE: 19

Met Leu Leu Leu Leu Phe Leu Trp Leu Met Asp Gln Asp Pro Trp Lys
1               5                   10                  15

Glu Arg Leu Glu Leu Leu His Lys Leu Glu Leu Leu Glu Leu Leu Leu
            20                  25                  30

Leu Leu Leu Phe Gln Glu Leu Leu Leu Met Glu Trp Thr Gln Glu Leu
        35                  40                  45

Leu Leu Leu Leu Leu Leu Leu Leu Leu Lys Leu Leu Glu Leu Leu Leu
    50                  55                  60

Leu Leu Leu Leu Leu Glu Leu Glu Asp His His Asn Lys Leu Ile Asn
65                  70                  75                  80

Lys Lys Leu Gly Glu Leu Leu Leu Glu Phe Leu Leu Glu Leu Leu Glu
            85                  90                  95

Met Met Phe Leu Leu Gly Leu Leu Leu Met Leu Gln Asp Leu Phe Phe
            100                 105                 110

Leu Leu Glu Leu Phe Asn Leu Leu Glu Leu His Lys Leu Leu Glu Leu
        115                 120                 125

Leu Glu His Ser Leu Leu Phe Phe Leu Lys Cys Met Leu Asp Gly Leu
    130                 135                 140

Glu Glu Cys Asn Ser Asp Ser Leu Leu Leu Asp Leu Glu Phe Leu Glu
145                 150                 155                 160

Glu Asp Leu Leu Leu Leu Leu Phe His Gln Glu Leu Lys Leu Asp Gln
            165                 170                 175

Val Leu Lys Leu Asp Asn Phe His Met Leu Leu Leu Met Leu Gly Leu
            180                 185                 190

Leu Asn Gln Leu Leu Leu Leu Cys Gln Thr Leu Asp Gln Leu Leu Glu
            195                 200                 205

Cys Leu Leu Glu Leu Leu Glu Gln Leu Glu Leu Leu Glu Gln Asp Leu
    210                 215                 220

Phe Gln Leu Leu Phe Phe Leu Phe Leu Leu Glu Leu Leu Glu Leu Leu
225                 230                 235                 240

Glu Leu Leu Leu Leu Glu His Leu Glu Asp Leu Leu Leu Leu Phe Lys
            245                 250                 255

Leu Leu Leu Lys Leu Asp His Leu Lys Leu Leu Glu Leu Asn Leu Leu
            260                 265                 270
```

What is claimed is:

1. A method for creating a population of prokaryotic cells comprising a DNA sequence of canonical codons encoding a polypeptide toxic to the prokaryotic cells comprising
introducing into an initial prokaryotic cell the DNA sequence of canonical codons encoding the polypeptide toxic to the initial prokaryotic cell,
wherein the initial prokaryotic cell is genomically recoded and lacks expression of one or more tRNAs cognate to one or more canonical codons thereby rendering the one or more canonical codons unassigned in the cell,
wherein lack of the initial prokaryotic cell to produce the one or more tRNAs cognate to the one or more canonical codons prevents translation and expression of the DNA sequence into the polypeptide toxic to the initial prokaryotic cell,
wherein the initial prokaryotic cell is grown to produce a population of prokaryotic cells in which the DNA sequence is stably maintained and propagated in the prokaryotic cells while translation and expression of the DNA sequence is prevented by the absence of a cognate tRNA.

2. The method of claim 1 wherein the cell is a bacterial cell.

3. The method of claim 1 wherein the polypeptide is a protein.

4. The method of claim 1, wherein toxicity is determined by a reduction in prokaryotic cell growth rate by at least 1% compared to growth rate of a corresponding wild type prokaryotic cell.

5. The method of claim 1 wherein the polypeptide is a protein that is toxic to the prokaryotic cell.

6. The method of claim 1 wherein the polypeptide is a protein that is toxic to the prokaryotic cell and wherein lack of the prokaryotic cell to produce the one or more tRNAs cognate to the one or more canonical codons prevents expression of the DNA sequence into the polypeptide, thereby reducing toxicity to the prokaryotic cell of the polypeptide compared to a non-recoded prokaryotic cell of the same strain.

7. The method of claim 1 wherein one or more tRNAs cognate to the one or more unassigned codons are provided within the prokaryotic cells of the population, and wherein the prokaryotic cells of the population express the DNA sequence into the polypeptide.

8. The method of claim 1 further comprising providing the prokaryotic cell with an expression plasmid or vector that is expressed to provide the one or more tRNAs cognate to the one or more canonical codons within the DNA sequence, wherein the prokaryotic cells within the population of prokaryotic cells transcribe and translate the DNA sequence to produce the polypeptide, or wherein the prokaryotic cells within the population of prokaryotic cells are genetically modified to encode one or more tRNAs cognate to one or more canonical codons within the DNA sequence under the influence of an inducible promoter and inducing the inducible promoter to begin transcription and translation of the DNA sequence to produce the polypeptide.

9. The method of claim 1, wherein toxicity is determined by a reduction in prokaryotic cell growth rate by at least 10% compared to growth rate of a corresponding wild type prokaryotic cell.

10. The method of claim 1, wherein toxicity is determined by a reduction in prokaryotic cell growth rate by at least 50% compared to growth rate of a corresponding wild type prokaryotic cell.

11. The method of claim 1, wherein toxicity is determined by a reduction in prokaryotic cell growth rate by at least 90% compared to growth rate of a corresponding wild type prokaryotic cell.

12. The method of claim 1 wherein the initial genomically recoded prokaryotic cell also lacks expression of one or more release factors cognate to one or more canonical codons.

13. A population of genomically recoded prokaryotic cells wherein the prokaryotic cells of the population lack expression of one or more tRNAs cognate to one or more canonical codons, wherein the prokaryotic cells within the population of prokaryotic cells comprise a DNA sequence of canonical codons encoding a polypeptide toxic to the prokaryotic cells, and wherein DNA sequence comprises the canonical codons whose recognition by the one or more cognate tRNAs is absent due to the lack of expression of the one or more cognate tRNAs, wherein the population of genomically recoded prokaryotic cells is grown from a genomically recoded prokaryotic cell including the DNA sequence of canonical codons encoding the polypeptide toxic to the prokaryotic cell, and wherein the DNA sequence is stably maintained and propagated in the prokaryotic cells while translation and expression of the DNA sequence is prevented by the absence of a cognate tRNA.

14. The population of genomically recoded prokaryotic cells of claim 13 wherein the prokaryotic cells of the population also lack expression of one or more release factors cognate to one or more canonical codons.

15. A population of altered prokaryotic cells lacking expression of one or more tRNAs cognate to one or more canonical codons within a DNA sequence encoding a polypeptide toxic to the prokaryotic cells comprising the DNA sequence, an expression plasmid or vector encoding the one or more tRNAs cognate to the one or more canonical codons within the DNA sequence, wherein the DNA sequence comprises the canonical codons whose recognition by the one or more cognate tRNAs is absent due to the lack of expression of the one or more cognate tRNAs, and wherein the prokaryotic cell is genomically recoded, and wherein the DNA sequence is stably maintained and propagated in the prokaryotic cells while translation and expression of the DNA sequence is prevented by the absence of a cognate tRNA.

16. The population of altered prokaryotic cells of claim 15 further lacking expression of one or more release factors cognate to one or more canonical codons.

* * * * *